United States Patent
Smith et al.

(10) Patent No.: US 10,907,202 B2
(45) Date of Patent: *Feb. 2, 2021

(54) METHODS AND APPARATUS FOR SEQUENTIAL AMPLIFICATION REACTIONS

(71) Applicant: Cepheid, Sunnyvale, CA (US)

(72) Inventors: Joseph H. Smith, Henderson, NV (US); David H. Persing, San Martin, CA (US); Alan Wortman, Redwood City, CA (US); Ronald Chang, Redwood City, CA (US); David Swenson, Santa Clara, CA (US)

(73) Assignee: Cepheid, Sunnyvale, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 15/849,125

(22) Filed: Dec. 20, 2017

(65) Prior Publication Data

US 2018/0187243 A1 Jul. 5, 2018

Related U.S. Application Data

(63) Continuation of application No. 14/553,622, filed on Nov. 25, 2014, now Pat. No. 9,873,909, which is a continuation of application No. 11/742,028, filed on Apr. 30, 2007, now Pat. No. 8,900,828.

(60) Provisional application No. 60/796,804, filed on May 1, 2006.

(51) Int. Cl.
| | |
|---|---|
| *C12Q 1/686* | (2018.01) |
| *C12Q 1/6851* | (2018.01) |
| *C12Q 1/6848* | (2018.01) |
| *B01L 3/00* | (2006.01) |
| *B01L 7/00* | (2006.01) |
| *C12Q 1/689* | (2018.01) |

(52) U.S. Cl.
CPC ........ *C12Q 1/686* (2013.01); *B01L 3/502738* (2013.01); *B01L 7/52* (2013.01); *C12Q 1/689* (2013.01); *C12Q 1/6848* (2013.01); *C12Q 1/6851* (2013.01); *B01L 2300/0654* (2013.01); *B01L 2300/0816* (2013.01); *B01L 2300/0864* (2013.01); *B01L 2400/0644* (2013.01)

(58) Field of Classification Search
CPC ........ C12Q 2537/149; C12Q 2565/629; C12Q 2537/143; C12Q 1/6848; C12Q 1/6851; C12Q 1/686; C12Q 2547/101; C12Q 1/689; B01L 2300/0654; B01L 2300/0816; B01L 2300/0864; B01L 2400/0644; B01L 3/502738; B01L 7/52
See application file for complete search history.

(56) References Cited

U.S. PATENT DOCUMENTS

| | | |
|---|---|---|
| 4,230,558 A | 10/1980 | Fulwyler |
| 4,683,195 A | 7/1987 | Mullis et al. |
| 4,683,202 A | 7/1987 | Mullis et al. |
| 4,800,159 A | 1/1989 | Mullis et al. |
| 4,811,218 A | 3/1989 | Hunkapiller et al. |
| 4,883,750 A | 11/1989 | Whitely et al. |
| 4,965,188 A | 10/1990 | Mullis et al. |
| 4,988,617 A | 1/1991 | Landegren et al. |
| 5,126,022 A | 6/1992 | Soane et al. |
| 5,210,015 A | 5/1993 | Gelfand et al. |
| 5,229,297 A | 7/1993 | Schnipelsky et al. |
| 5,399,491 A | 3/1995 | Kacian et al. |
| 5,427,930 A | 6/1995 | Birkenmeyer et al. |
| 5,476,930 A | 12/1995 | Letsinger et al. |
| 5,498,392 A | 3/1996 | Wilding et al. |
| 5,556,773 A | 9/1996 | Yourno |
| 5,582,989 A | 12/1996 | Caskey et al. |
| 5,587,128 A | 12/1996 | Wilding et al. |
| 5,589,136 A | 12/1996 | Northrup et al. |
| 5,593,826 A | 1/1997 | Fung et al. |
| 5,646,001 A | 7/1997 | Terstappen et al. |
| 5,648,211 A | 7/1997 | Walker |
| 5,665,582 A | 9/1997 | Kausch |
| 5,712,124 A | 1/1998 | Walker |
| 5,714,380 A | 2/1998 | Neri et al. |
| 5,720,923 A | 2/1998 | Haff et al. |

(Continued)

FOREIGN PATENT DOCUMENTS

| | | |
|---|---|---|
| EP | 0687502 | 12/1995 |
| JP | 04-262799 A | 9/1992 |

(Continued)

OTHER PUBLICATIONS

Bernard, Philip S. et al.; "Color Multiplexing Hybridization Probes Using the Apolipoprotein E Locus as a Model System for Genotyping"; 1999, *Analytical Biochemistry*, vol. 273, pp. 221-228.

Bernard, Philip S. et al.; "Real-Time PCR Technology for Cancer Diagnostics"; 2002, *Clinical Chemistry*, vol. 48, No. 8, pp. 1178-1185.

Cheng, Jing et al.; "Sample Preparation in Microstructured Devices"; 1998, *Topics in Current Chemistry*, vol. 194, pp. 215-231.

Elnifro, Elfath M. et al.; "Multiplex PCR: Optimization and Application in Diagnostic Virology"; 2000, *Clinical Microbiology Reviews*, vol. 13, No. 4, pp. 559-570.

Freeman, Willard M. et al.; "Quantitative RT-PCR: Pitfalls and Potential"; 1999, *BioTechniques*, vol. 26, No. 1, pp. 112-125.

(Continued)

*Primary Examiner* — Cynthia B Wilder

(74) *Attorney, Agent, or Firm* — Kilpatrick Townsend & Stockton LLP

(57) ABSTRACT

The invention provides methods and apparatus for carrying out multiple amplification reactions in a single reaction chamber by successive cycles of loading reaction mixture, amplifying, and removing spent reaction mixture in a fluidly closed reaction system. In particular, the present invention allows amplification of a plurality of target polynucleotides from a single sample by carrying out under closed-loop control successive amplifications of different target polynucleotides from different portions of the sample.

18 Claims, 28 Drawing Sheets

(56) References Cited

U.S. PATENT DOCUMENTS

| | | |
|---|---|---|
| 5,746,978 A | 5/1998 | Bienhaus et al. |
| 5,779,977 A | 7/1998 | Haff et al. |
| 5,827,480 A | 10/1998 | Haff et al. |
| 5,854,033 A | 12/1998 | Lizardi |
| 5,858,195 A | 1/1999 | Ramsey |
| 5,925,517 A | 7/1999 | Tyagi et al. |
| 5,948,673 A | 9/1999 | Cottingham |
| 5,998,224 A | 12/1999 | Rohr et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,126,899 A | 10/2000 | Woudenberg et al. |
| 6,168,948 B1 | 1/2001 | Anderson et al. |
| 6,171,785 B1 | 1/2001 | Higuchi et al. |
| 6,174,670 B1 | 1/2001 | Wittwer et al. |
| 6,365,362 B1 | 4/2002 | Terstappen et al. |
| 6,369,893 B1 | 4/2002 | Christel et al. |
| 6,374,684 B1 | 4/2002 | Dority |
| 6,399,952 B1 | 6/2002 | Maher et al. |
| 6,403,037 B1 | 6/2002 | Chang et al. |
| 6,569,627 B2 | 5/2003 | Wittwer et al. |
| 6,605,451 B1 | 8/2003 | Mamaro et al. |
| 6,613,525 B2 | 9/2003 | Nelson et al. |
| 6,663,833 B1 | 12/2003 | Stave et al. |
| 6,713,297 B2 | 3/2004 | McMillan et al. |
| 6,818,185 B1 | 11/2004 | Peterson et al. |
| 6,960,437 B2 | 11/2005 | Enzelberger et al. |
| 7,542,652 B2 | 4/2009 | Ammann et al. |
| 8,133,703 B2 | 3/2012 | Ching et al. |
| 8,900,828 B2 * | 12/2014 | Smith .................... C12Q 1/686 435/6.1 |
| 2005/0233314 A1 | 10/2005 | Juang et al. |
| 2006/0177844 A1 * | 8/2006 | Ching .................... B01L 3/502 435/6.12 |
| 2006/0246493 A1 | 11/2006 | Jensen et al. |

FOREIGN PATENT DOCUMENTS

| | | |
|---|---|---|
| WO | 99/19717 A1 | 4/1999 |
| WO | 02/24322 A2 | 3/2002 |
| WO | 2006/047777 | 5/2006 |

OTHER PUBLICATIONS

Gulliksen, Anja et al.; "Real-Time Nucleic Acid Sequence-Based Amplification in Nanoliter Volumes"; 2004, *Anal. Chem.*, vol. 27, pp. 9-14.

Henegariu, O. et al.; "Multiplex PCR: Critical Parameters and Step-by-Step Protocol"; 1997, *BioTechniques*, vol. 23, No. 3, pp. 504-511.

Jekelis, Albert W.; "Increased Instrument Intelligence—Can it Reduce Laboratory Error?"; 2005, *Biomed Instrum Technol*, vol. 39, pp. 232-236.

Koch, Walter H.; "Technology Platforms for Pharmacogenomic Diagnostic Assays"; 2004, *Nature Reviews*, vol. 3, pp. 749-761.

Liu, Jian et al.; "Solving the "World-to-Chip" Interface Problem with a Microfluidic Matrix"; 2003, *Anal. Chem.*, vol. 75, pp. 4718-4723.

Mackay, I.M.; "Real-time PCR in the microbiology laboratory"; 2004, *European Society of Clinical Microbiology and Infectious Diseases*, vol. 10, pp. 190-212.

Morrison, Tom B. et al.; "Quantification of Low-Copy Transcripts by Continuous SYBR® Green I Monitoring during Amplification"; 1998, *BioTechniques*, vol. 24, No. 6, pp. 954-962.

Radonic, Aleksandar et al.; "Guideline to reference gene selection for quantitative real-time PCR"; 2004, *Biochemical and Biophysical Research Communications*, vol. 313, pp. 856-862.

Raja, Siva et al.; "Temperature-controlled Primer Limit for Multiplexing of Rapid, Quantitative Reverse Transcription-PCR Assays: Applicatio to Intraoperative Cancer Diagnostics"; 2002, *Clinical Chemistry*, vol. 48, No. 8, pp. 1329-1337.

Schweitzer, Barry et al.; "Combining nucleic acid amplification and detection"; 2001, *Current Opinion in Biotechnology*, vol. 12, pp. 21-27.

Selvey, S. et al.; "β-Actin-an unsuitable internal control for RT-PCR"; 2001, *Molecular and Cellular Probes*, vol. 15, pp. 307-311.

* cited by examiner

Fig. 3A

| # | Command | Parameters | | |
|---|---|---|---|---|
| 1 | Log Pressure On | Log Pressure at 500 ms interval. | | |
| 2 | Aspirate | From Buffer TET | 250uL @ 60 uL/sec | Direct Path |
| 3 | Dispense | To Waste | 250 uL @ 30 uL/sec | Filter Path |
| 4 | Wait | 3.0 second(s) | | |
| 5 | Toggle | To Lysate | 3x Asp:150@20 Disp:150@20 | Direct Path |
| 6 | Aspirate Air | From Air | 20uL @ 20 uL/sec | Direct Path |
| 7 | Dispense Air | To Waste | 20 uL @ 20 uL/sec | Filter Path |
| 8 | Wait | 3.0 second(s) | | |
| 9 | Aspirate | From Lysate | 50uL @ 20 uL/sec | Direct Path |
| 10 | Dispense | To Lysate | 10 uL @ 20 uL/sec | Direct Path |
| 11 | Dispense | To Beads 1 | 40 uL @ 20 uL/sec | Direct Path |
| 12 | Aspirate | From Beads 1 | 80uL @ 20 uL/sec | Direct Path |
| 13 | Toggle | To Beads 1 | 12x Disp:80@20 Asp:80@20 | Direct Path |
| 14 | Dispense | To Master Mix | 80 uL @ 20 uL/sec | Direct Path |
| 15 | Wait | 10.0 second(s) | | |
| 16 | Aspirate Air | From Air | 50uL @ 40 uL/sec | Direct Path |
| 17 | Aspirate | Into Tube | 65uL @ 20 uL/sec | Direct Path |
| 18 | Dispense | To Tube | 5 uL @ 10 uL/sec | Direct Path |
| 19 | Wait | 3.0 second(s) | | |
| 20 | Pressurize Tube | 50 uL @ 40 uL/sec | No Valve Move After Pre... | |
| 21 | Log Pressure Off | | | |
| 22 | Protocol | 1: Hold, 2: 3-Temperature Cycle; | | |
| 23 | Depressurize Tube | 50 uL @ 40uL/sec | Filter Path | |
| 24 | Dispense Air | To Waste | 50 uL @ 40 uL/sec | Direct Path |
| 25 | Dispense | To Tube | 60 uL @ 20 uL/sec | Direct Path |
| 26 | Aspirate | From Master Mix | 80uL @ 20 uL/sec | Direct Path |
| 27 | Dispense | To Waste | 80 uL @ 40 uL/sec | Direct Path |
| 28 | Aspirate | From Buffer TET | 70uL @ 40 uL/sec | Direct Path |
| 29 | Dispense | To Master Mix | 70 uL @ 20 uL/sec | Direct Path |
| 30 | Aspirate | Into Tube | 60uL @ 20 uL/sec | Direct Path |
| 31 | Dispense | To Tube | 60 uL @ 20 uL/sec | Direct Path |
| 32 | Wait | 3.0 second(s) | | |
| 33 | Aspirate | From Master Mix | 70uL @ 20 uL/sec | Direct Path |
| 34 | Aspirate Air | From Master Mix | 100uL @ 40 uL/sec | Direct Path |
| 35 | Dispense | To Waste | 70 uL @ 40 uL/sec | Direct Path |
| 36 | Dispense Air | To Waste | 100 uL @ 40 uL/sec | Direct Path |
| 37 | Aspirate Air | From Air | 500uL @ 80 uL/sec | Direct Path |
| 38 | Dispense Air | To Tube | 500 uL @ 100 uL/sec | Direct Path |
| 39 | Protocol | 1: 2-Temperature Cycle; | | |
| 40 | Toggle | To Lysate | 3x Asp:100@20 Disp:100@20 | Direct Path |
| 41 | Aspirate Air | From Air | 20uL @ 20 uL/sec | Direct Path |
| 42 | Dispense Air | To Waste | 20 uL @ 20 uL/sec | Filter Path |
| 43 | Wait | 3.0 second(s) | | |
| 44 | Aspirate | From Lysate | 50uL @ 20 uL/sec | Direct Path |
| 45 | Dispense | To Lysate | 10 uL @ 20 uL/sec | Direct Path |
| 46 | Dispense | To Beads 2 | 40 uL @ 20 uL/sec | Direct Path |
| 47 | Aspirate | From Beads 2 | 80uL @ 20 uL/sec | Direct Path |
| 48 | Toggle | To Beads 2 | 12x Disp:80@20 Asp:80@20 | Direct Path |
| 49 | Dispense | To Master Mix | 80 uL @ 20 uL/sec | Direct Path |
| 50 | Wait | 10.0 second(s) | | |
| 51 | Aspirate Air | From Air | 50uL @ 40 uL/sec | Direct Path |
| 52 | Aspirate | Into Tube | 65uL @ 20 uL/sec | Direct Path |
| 53 | Dispense | To Tube | 5 uL @ 10 uL/sec | Direct Path |
| 54 | Wait | 3.0 second(s) | | |
| 55 | Pressurize Tube | 50 uL @ 40 uL/sec | No Valve Move After Pre... | |
| 56 | Log Pressure Off | | | |
| 57 | Protocol | 1: Hold, 2: 3-Temperature Cycle; | | |
| 58 | Depressurize Tube | 50 uL @ 40uL/sec | Filter Path | |

Fig. 4A

| # | Command | Parameters | | |
|---|---|---|---|---|
| | | Command Sequence | | |
| 1 | Log Pressure On | Log Pressure at 500ms interval. | | |
| 2 | Aspirate | From EtOH | 700 uL @ 80 uL/sec | Direct Path |
| 3 | Dispense | To Lysis | 700 uL @ 40 uL/sec | Direct Path |
| 4 | Toggle | To Lysis | 4x Asp:700@60 Disp:700@60 | Direct Path |
| 5 | Start Repeat | 2 time(s) | | |
| 6 | Aspirate | From Lysis | 675 uL @ 60 uL/sec | Direct Path |
| 7 | Dispense | To Waste | 675 uL @ 10 uL/sec | Filter Path |
| 8 | End Repeat | | | |
| 9 | Aspirate | From Wash Buffer | 350 uL @ 60 uL/sec | Direct Path |
| 10 | Start Repeat | 3 time(s) | | |
| 11 | Dispense | To Waste | 100 uL @ 10 uL/sec | Filter Path |
| 12 | Wait | 5.0 second(s) | | |
| 13 | End Repeat | | | |
| 14 | Dispense | To Waste | 50 uL @ 60 uL/sec | Direct Path |
| 15 | Aspirate Air | From Air | 200 uL @ 60 uL/sec | Direct Path |
| 16 | Dispense Air | To Waste | 200 uL @ 60 uL/sec | Filter Path |
| 17 | Aspirate | From Elution Buffer | 250 uL @ 40 uL/sec | Direct Path |
| 18 | Dispense | To Waste | 250 uL @ 40 uL/sec | Direct Path |
| 19 | Aspirate | From Elution Buffer | 120 uL @ 40 uL/sec | Direct Path |
| 20 | Dispense | To Elution Buffer | 10 uL @ 10 uL/sec | Direct Path |
| 21 | Dispense | To Waste | 30 uL @ 5 uL/sec | Filter Path |
| 22 | Dispense | To RT Beads | 60 uL @ 20 uL/sec | Filter Path |
| 23 | Dispense | To Waste | 20 uL @ 40 uL/sec | Direct Path |
| 24 | Wait | 5.0 second(s) | | |
| 25 | Toggle | To RT Beads | 3x Asp:45@10 Disp:45@10 | Direct Path |
| 26 | Aspirate | From RT Beads | 65 uL @ 20 uL/sec | Direct Path |
| 27 | Dispense | To Chamber 7 | 65 uL @ 20 uL/sec | Direct Path |
| 28 | Aspirate | Into Tube | 60 uL @ 15 uL/sec | Direct Path |
| 29 | Protocol | 1: 3-Temp Cycle; | | |
| 30 | Dispense | To Tube | 60 uL @ 40 uL/sec | Direct Path |
| 31 | Aspirate | Into Tube | 60 uL @ 15 uL/sec | Direct Path |
| 32 | Protocol | 1: 2-Temp Cycle; | | |
| 33 | Dispense | To Tube | 60 uL @ 40 uL/sec | Direct Path |
| 34 | Aspirate | From Elution Buffer | 20 uL @ 30 uL/sec | Direct Path |
| 35 | Aspirate | From Chamber 7 | 65 uL @ 40 uL/sec | Direct Path |
| 36 | Dispense | To PCR Beads | 85 uL @ 40 uL/sec | Direct Path |
| 37 | Toggle | To PCR Beads | 6x Asp:65@60 Disp:65@60 | Direct Path |
| 38 | Aspirate Air | Into Tube | 600 uL @ 100 uL/sec | Direct Path |
| 39 | Dispense Air | To Air | 600 uL @ 100 uL/sec | Direct Path |
| 40 | Aspirate | From PCR Beads | 85 uL @ 40 uL/sec | Direct Path |
| 41 | Dispense | To Chamber 7 | 85 uL @ 40 uL/sec | Direct Path |
| 42 | Aspirate Air | From Air | 35 uL @ 40 uL/sec | Direct Path |
| 43 | Aspirate | Into Tube | 65 uL @ 20 uL/sec | Direct Path |
| 44 | Pressurize Tube | 35 uL @ 40 uL/sec Direct Path | | |
| 45 | Log Pressure Off | | | |
| 46 | Protocol | 1 Hold; 2 3-Temp Cycle; 3: 2-Temp Cycle; | | |
| 47 | Depressurize T... | 35 uL @ 40 uL/sec Filter Path | | |

Fig. 6A

| # | Command | Parameters | | |
|---|---------|------------|---|---|
| 1 | Log Pressure On | Log Pressure at 500ms interval. | | |
| 2 | Aspirate | From EtOH | 700 uL @ 60 uL/sec | Direct Path |
| 3 | Dispense | To Lysis | 700 uL @ 40 uL/sec | Direct Path |
| 4 | Toggle | To Lysis | 4x Asp:700@60 Disp:700@60 | Direct Path |
| 5 | Start Repeat | 2 time(s) | | |
| 6 | Aspirate | From Lysis | 875 uL @ 60 uL/sec | Direct Path |
| 7 | Dispense | To Waste | 875 uL @ 10 uL/sec | Filter Path |
| 8 | End Repeat | | | |
| 9 | Aspirate | From Wash Buffer | 350 uL @ 60 uL/sec | Direct Path |
| 10 | Start Repeat | 3 time(s) | | |
| 11 | Dispense | To Waste | 100 uL @ 10 uL/sec | Filter Path |
| 12 | Wait | 5.0 second(s) | | |
| 13 | End Repeat | | | |
| 14 | Dispense | To Waste | 50 uL @ 60 uL/sec | Direct Path |
| 15 | Aspirate Air | From Air | 200 uL @ 60 uL/sec | Direct Path |
| 16 | Dispense Air | To Waste | 200 uL @ 60 uL/sec | Filter Path |
| 17 | Aspirate | From Elution Buffer | 250 uL @ 40 uL/sec | Direct Path |
| 18 | Dispense | To Waste | 250 uL @ 40 uL/sec | Direct Path |
| 19 | Aspirate | From Elution Buffer | 120 uL @ 40 uL/sec | Direct Path |
| 20 | Dispense | To Elution Buffer | 10 uL @ 10 uL/sec | Direct Path |
| 21 | Dispense | To Waste | 30 uL @ 5 uL/sec | Filter Path |
| 22 | Dispense | To RT Beads | 60 uL @ 20 uL/sec | Filter Path |
| 23 | Dispense | To Waste | 20 uL @ 40 uL/sec | Direct Path |
| 24 | Wait | 5.0 second(s) | | |
| 25 | Toggle | To RT Beads | 3x Asp:45@10 Disp:45@10 | Direct Path |
| 26 | Aspirate | From RT Beads | 65 uL @ 20 uL/sec | Direct Path |
| 27 | Dispense | To Chamber 7 | 65 uL @ 20 uL/sec | Direct Path |
| 28 | Aspirate | Into Tube | 60 uL @ 15 uL/sec | Direct Path |
| 29 | Protocol | 1: 3-Temp Cycle; | | |
| 30 | Dispense | To Tube | 60 uL @ 40 uL/sec | Direct Path |
| 31 | Aspirate | Into Tube | 60 uL @ 15 uL/sec | Direct Path |
| 32 | Protocol | 1: 2-Temp Cycle; | | |
| 33 | Dispense | To Tube | 60 uL @ 40 uL/sec | Direct Path |
| 34 | Aspirate | From Elution Buffer | 20 uL @ 30 uL/sec | Direct Path |
| 35 | Aspirate | From Chamber 7 | 65 uL @ 40 uL/sec | Direct Path |
| 36 | Dispense | To PCR Beads | 85 uL @ 40 uL/sec | Direct Path |
| 37 | Toggle | To PCR Beads | 8x Asp:65@60 Disp:65@60 | Direct Path |
| 38 | Aspirate | From PCR Beads | 95 uL @ 40 uL/sec | Direct Path |
| 39 | Dispense | To Chamber 7 | 85 uL @ 40 uL/sec | Direct Path |
| 40 | Aspirate Air | From Air | 35 uL @ 40 uL/sec | Direct Path |
| 41 | Protocol | 1: Hold; | | |
| 42 | Aspirate | Into Tube | 85 uL @ 20 uL/sec | Direct Path |
| 43 | Pressurize Tube | 35 uL @ 40 uL/sec Direct Path | | |
| 44 | Log Pressure Off | | | |
| 45 | Protocol | 1: Hold; 2: 3-Temp Cycle; 3: 2-Temp Cycle; | | |
| 46 | Depressurize T... | 35 uL @ 40 uL/sec Filter Path | | |

Fig. 6B

| # | Command | Parameters | | |
|---|---|---|---|---|
| 1 | Log Pressure On | Log Pressure at 500ms interval. | | |
| 2 | Aspirate | From EtOH | 700 uL @ 80 uL/sec | Direct Path |
| 3 | Dispense | To Lysis | 700 uL @ 40 uL/sec | Direct Path |
| 4 | Toggle | To Lysis | 4x Asp:700@60 Disp 700@60 | Direct Path |
| 5 | Start Repeat | 2 time(s) | | |
| 6 | Aspirate | From Lysis | 675 uL @ 80 uL/sec | Direct Path |
| 7 | Dispense | To Waste | 675 uL @ 10 uL/sec | Filter Path |
| 8 | End Repeat | | | |
| 9 | Aspirate | From Wash Buffer | 350 uL @ 80 uL/sec | Direct Path |
| 10 | Start Repeat | 3 time(s) | | |
| 11 | Dispense | To Waste | 100 uL @ 10 uL/sec | Filter Path |
| 12 | Wait | 5.0 second(s) | | |
| 13 | End Repeat | | | |
| 14 | Dispense | To Waste | 50 uL @ 60 uL/sec | Direct Path |
| 15 | Aspirate Air | From Air | 200 uL @ 80 uL/sec | Direct Path |
| 16 | Dispense Air | To Waste | 200 uL @ 80 uL/sec | Filter Path |
| 17 | Aspirate | From Elution Buffer | 250 uL @ 40 uL/sec | Direct Path |
| 18 | Dispense | To Waste | 250 uL @ 40 uL/sec | Direct Path |
| 19 | Aspirate | From Elution Buffer | 120 uL @ 40 uL/sec | Direct Path |
| 20 | Dispense | To Elution Buffer | 10 uL @ 10 uL/sec | Direct Path |
| 21 | Dispense | To Waste | 30 uL @ 5 uL/sec | Filter Path |
| 22 | Dispense | To RT Beads | 60 uL @ 20 uL/sec | Filter Path |
| 23 | Dispense | To Waste | 20 uL @ 40 uL/sec | Direct Path |
| 24 | Wait | 5.0 second(s) | | |
| 25 | Toggle | To RT Beads | 3x Asp:45@10 Disp:45@10 | Direct Path |
| 26 | Aspirate | From RT Beads | 65 uL @ 20 uL/sec | Direct Path |
| 27 | Dispense | To Chamber 7 | 65 uL @ 20 uL/sec | Direct Path |
| 28 | Aspirate | Into Tube | 60 uL @ 15 uL/sec | Direct Path |
| 29 | Protocol | 1: 3-Temp Cycle; | | |
| 30 | Dispense | To Tube | 60 uL @ 40 uL/sec | Direct Path |
| 31 | Aspirate | Into Tube | 60 uL @ 15 uL/sec | Direct Path |
| 32 | Protocol | 1: 2-Temp Cycle; | | |
| 33 | Dispense | To Tube | 60 uL @ 40 uL/sec | Direct Path |
| 34 | Aspirate | From Elution Buffer | 20 uL @ 30 uL/sec | Direct Path |
| 35 | Aspirate | From Chamber 7 | 65 uL @ 40 uL/sec | Direct Path |
| 36 | Dispense | To PCR Beads | 85 uL @ 40 uL/sec | Direct Path |
| 37 | Toggle | To PCR Beads | 6x Asp:65@60 Disp:65@60 | Direct Path |
| 38 | Aspirate | From PCR Beads | 85 uL @ 40 uL/sec | Direct Path |
| 39 | Dispense | To Chamber 7 | 85 uL @ 40 uL/sec | Direct Path |
| 40 | Aspirate Air | From Air | 35 uL @ 40 uL/sec | Direct Path |
| 41 | Protocol | 1: 2-Temp Cycle; | | |
| 42 | Aspirate | Into Tube | 65 uL @ 20 uL/sec | Direct Path |
| 43 | Pressurize Tube | 35 uL @ 40 uL/sec | Direct Path | |
| 44 | Log Pressure Off | | | |
| 45 | Protocol | 1: Hold; 2: 3-Temp Cycle; 3: 2-Temp Cycle; | | |
| 46 | Depressurize T | 35 uL @ 40 uL/sec | Filter Path | |

Fig. 6C

| # | Command | Parameters | | |
|---|---------|-----------|---|---|
| 1 | Log Pressure On | Log Pressure at 500ms interval. | | |
| 2 | Aspirate | From EtOH | 700 uL @ 60 uL/sec | Direct Path |
| 3 | Dispense | To Lysis | 700 uL @ 40 uL/sec | Direct Path |
| 4 | Toggle | To Lysis | 4x Asp:700@60 Disp:700@60 | Direct Path |
| 5 | Start Repeat | 2 time(s) | | |
| 6 | Aspirate | From Lysis | 675 uL @ 60 uL/sec | Direct Path |
| 7 | Dispense | To Waste | 675 uL @ 10 uL/sec | Filter Path |
| 8 | End Repeat | | | |
| 9 | Aspirate | From Wash Buffer | 350 uL @ 60 uL/sec | Direct Path |
| 10 | Start Repeat | 3 time(s) | | |
| 11 | Dispense | To Waste | 100 uL @ 10 uL/sec | Filter Path |
| 12 | Wait | 5.0 second(s) | | |
| 13 | End Repeat | | | |
| 14 | Dispense | To Waste | 50 uL @ 60 uL/sec | Direct Path |
| 15 | Aspirate Air | From Air | 200 uL @ 60 uL/sec | Direct Path |
| 16 | Dispense Air | To Waste | 200 uL @ 60 uL/sec | Filter Path |
| 17 | Aspirate | From Elution Buffer | 250 uL @ 40 uL/sec | Direct Path |
| 18 | Dispense | To Waste | 250 uL @ 40 uL/sec | Direct Path |
| 19 | Aspirate | From Elution Buffer | 120 uL @ 40 uL/sec | Direct Path |
| 20 | Dispense | To Elution Buffer | 10 uL @ 10 uL/sec | Direct Path |
| 21 | Dispense | To Waste | 30 uL @ 5 uL/sec | Filter Path |
| 22 | Dispense | To RT Beads | 60 uL @ 20 uL/sec | Filter Path |
| 23 | Dispense | To Waste | 20 uL @ 40 uL/sec | Direct Path |
| 24 | Wait | 5.0 second(s) | | |
| 25 | Toggle | To RT Beads | 3x Asp:45@10 Disp:45@10 | Direct Path |
| 26 | Aspirate | From RT Beads | 65 uL @ 20 uL/sec | Direct Path |
| 27 | Dispense | To Chamber 7 | 65 uL @ 20 uL/sec | Direct Path |
| 28 | Aspirate | Into Tube | 60 uL @ 15 uL/sec | Direct Path |
| 29 | Protocol | 1: 3-Temp Cycle; | | |
| 30 | Dispense | To Tube | 60 uL @ 40 uL/sec | Direct Path |
| 31 | Aspirate | Into Tube | 60 uL @ 15 uL/sec | Direct Path |
| 32 | Protocol | 1: 2-Temp Cycle; | | |
| 33 | Dispense | To Tube | 60 uL @ 40 uL/sec | Direct Path |
| 34 | Aspirate | From Elution Buffer | 20 uL @ 30 uL/sec | Direct Path |
| 35 | Aspirate | From Chamber 7 | 65 uL @ 40 uL/sec | Direct Path |
| 36 | Dispense | To PCR Beads | 85 uL @ 40 uL/sec | Direct Path |
| 37 | Toggle | To PCR Beads | 6x Asp:85@60 Disp:85@60 | Direct Path |
| 38 | Aspirate Air | From Air | 600 uL @ 100 uL/sec | Direct Path |
| 39 | Dispense Air | To Tube | 600 uL @ 100 uL/sec | Direct Path |
| 40 | Aspirate | From PCR Beads | 85 uL @ 40 uL/sec | Direct Path |
| 41 | Dispense | To Chamber 7 | 85 uL @ 40 uL/sec | Direct Path |
| 42 | Aspirate Air | From Air | 35 uL @ 40 uL/sec | Direct Path |
| 43 | Aspirate | Into Tube | 65 uL @ 20 uL/sec | Direct Path |
| 44 | Pressurize Tube | 35 uL @ 40 uL/sec | Direct Path | |
| 45 | Log Pressure Off | | | |
| 46 | Protocol | 1: Hold; 2: 3-Temp Cycle; 3: 2-Temp Cycle; | | |
| 47 | Depressurize T... | 35 uL @ 40 uL/sec | Filter Path | |

Fig. 6D

| # | Command | Parameters | | |
|---|---|---|---|---|
| 1 | Log Pressure On | Log Pressure at 500ms interval | | |
| 2 | Aspirate | From EtOH | 700 uL @ 60 uL/sec | Direct Path |
| 3 | Dispense | To Lysis | 700 uL @ 40 uL/sec | Direct Path |
| 4 | Toggle | To Lysis | 4x Asp:700@60 Disp:700@60 | Direct Path |
| 5 | Start Repeat | 2 time(s) | | |
| 6 | Aspirate | From Lysis | 675 uL @ 60 uL/sec | Direct Path |
| 7 | Dispense | To Waste | 675 uL @ 10 uL/sec | Filter Path |
| 8 | End Repeat | | | |
| 9 | Aspirate | From Wash Buffer | 350 uL @ 60 uL/sec | Direct Path |
| 10 | Start Repeat | 3 time(s) | | |
| 11 | Dispense | To Waste | 100 uL @ 10 uL/sec | Filter Path |
| 12 | Wait | 5.0 second(s) | | |
| 13 | End Repeat | | | |
| 14 | Dispense | To Waste | 50 uL @ 60 uL/sec | Direct Path |
| 15 | Aspirate Air | From Air | 200 uL @ 60 uL/sec | Direct Path |
| 16 | Dispense Air | To Waste | 200 uL @ 60 uL/sec | Filter Path |
| 17 | Aspirate | From Elution Buffer | 260 uL @ 40 uL/sec | Direct Path |
| 18 | Dispense | To Waste | 260 uL @ 40 uL/sec | Direct Path |
| 19 | Aspirate | From Elution Buffer | 120 uL @ 40 uL/sec | Direct Path |
| 20 | Dispense | To Elution Buffer | 10 uL @ 10 uL/sec | Direct Path |
| 21 | Dispense | To Waste | 30 uL @ 5 uL/sec | Filter Path |
| 22 | Dispense | To RT Beads | 60 uL @ 20 uL/sec | Filter Path |
| 23 | Dispense | To Waste | 20 uL @ 40 uL/sec | Direct Path |
| 24 | Wait | 5.0 second(s) | | |
| 25 | Toggle | To RT Beads | 3x Asp:45@10 Disp:45@10 | Direct Path |
| 26 | Aspirate | From RT Beads | 65 uL @ 20 uL/sec | Direct Path |
| 27 | Dispense | To Chamber 7 | 65 uL @ 20 uL/sec | Direct Path |
| 28 | Aspirate | Into Tube | 60 uL @ 15 uL/sec | Direct Path |
| 29 | *Protocol* | 1: 3-Temp Cycle; | | |
| 30 | Dispense | To Tube | 60 uL @ 40 uL/sec | Direct Path |
| 31 | Aspirate | Into Tube | 60 uL @ 15 uL/sec | Direct Path |
| 32 | *Protocol* | 1: 2-Temp Cycle; | | |
| 33 | Dispense | To Tube | 60 uL @ 40 uL/sec | Direct Path |
| 34 | Aspirate | From Elution Buffer | 20 uL @ 30 uL/sec | Direct Path |
| 35 | Aspirate | From Chamber 7 | 65 uL @ 40 uL/sec | Direct Path |
| 36 | Dispense | To PCR Beads | 85 uL @ 40 uL/sec | Direct Path |
| 37 | Toggle | To PCR Beads | 6x Asp:65@60 Disp:65@60 | Direct Path |
| 38 | Aspirate | From PCR Beads | 85 uL @ 40 uL/sec | Direct Path |
| 39 | Dispense | To Chamber 7 | 85 uL @ 40 uL/sec | Direct Path |
| 40 | Aspirate Air | From Air | 35 uL @ 40 uL/sec | Direct Path |
| 41 | *Protocol* | 1: 2-Temp Cycle; | | |
| 42 | Aspirate | Into Tube | 65 uL @ 20 uL/sec | Direct Path |
| 43 | Pressurize Tube | 35 uL @ 40 uL/sec Direct Path | | |
| 44 | Log Pressure Off | | | |
| 45 | *Protocol* | 1: Hold; 2: 3-Temp Cycle; 3: 2-Temp Cycle; | | |
| 46 | Depressurize T... | 35 uL @ 40 uL/sec Filter Path | | |

Fig. 6E

METHODS AND APPARATUS FOR SEQUENTIAL AMPLIFICATION REACTIONS

CROSS-REFERENCES TO RELATED APPLICATIONS

This application is a continuation of U.S. application Ser. No. 14/553,622, filed Nov. 25, 2014, which is a continuation of U.S. patent application Ser. No. 11/742,028, filed Apr. 30, 2007, now U.S. Pat. No. 8,900,828, which claims priority from U.S. Provisional Application No. 60/796,804 filed May 1, 2006, the entire contents of which are herein incorporated by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The invention relates generally to methods for analyzing a sample for the presence of one or more nucleic acids, and more particularly, to methods for conducting multi-stage nucleic acid amplification reactions, especially polymerase chain reactions (PCRs).

BACKGROUND OF THE INVENTION

Nucleic acid amplification is a crucial component of many techniques used in research, medicine, and industry. Such reactions are used in clinical and biological research, detection and monitoring of infectious diseases, detection of mutations, detection of cancer markers, environmental monitoring, genetic identification, detection of pathogens in biodefense applications, and the like, e.g. Schweitzer et al. *Current Opinion in Biotechnology*, 12:21-27 (2001); Koch, *Nature Reviews Drug Discovery*, 3:749-761 (2004). In particular, polymerase chain reactions (PCRs) have found applications in all of these areas, including applications for viral and bacterial detection, viral load monitoring, detection of rare and/or difficult-to-culture pathogens, rapid detection of bio-terror threats, detection of minimal residual disease in cancer patients, food pathogen testing, blood supply screening, and the like, e.g. Mackay, *Clin. Microbiol. Infect.*, 10:190-212 (2004); Bernard et al. *Clinical Chemistry*, 48:1178-1185 (2002). In regard to PCR, key reasons for such widespread use are its speed and ease of use (typically performed within a few hours using standardized kits and relatively simple and low cost instruments), its sensitivity (often a few tens of copies of a target sequence in a sample can be detected), and its robustness (poor quality samples or preserved samples, such as forensic samples or fixed tissue samples are readily analyzed), Strachan and Read, *Human Molecular Genetics 2nd Ed.* (John Wiley & Sons, New York, 1999).

Because of these advantages, there has been interest in extending amplification techniques to accommodate multiple target polynucleotides from the same biological sample. Several approaches have been taken including (i) simultaneously carrying out multiple amplifications in a single reaction, e.g. multiplex PCR, for example described in Caskey et al. U.S. Pat. No. 5,582,989; Elnifro et al. *Clinical Microbiology Reviews*, 13:559-570 (2000); Henegariu et al. *BioTechniques*, 23:504-511 (1997); (ii) sequentially carrying out multiple amplifications in a single reaction by mid-course adjustments in reaction conditions to favor different reactants, e.g. Raja et al. *Clinical Chemistry*, 48:1329-1337 (2002); and (iii) aliquoting portions of a sample into several reaction chambers for separate amplifications, often using a microfluidics device, e.g. described in Cottingham, U.S. Pat. No. 5,948,673; Mamaro et al. U.S. Pat. No. 6,605,451; Enzelberger et al. U.S. Pat. No. 6,960,437; Liu et al. *Anal. Chem.*, 75:4718-4723 (2003); Woudenberg et al. U.S. Pat. No. 6,126,899; Gulliksen et al. *Anal. Chem.*, 76:9-14 (2004); Anderson et al. U.S. Pat. No. 6,168,948; and the like. The first approach has proven difficult to implement routinely because of the difficulty in finding reaction conditions under which all reactants, such as different primers and target sequences, are amplified at approximately the same rates. The second approach has had some success particularly where rapid amplification of a few sequences of widely varying abundances is required; however, there are severe constraints on available reaction parameters to manipulate in order to obtain preferential amplification of different sequences. The third approach has the potential for permitting multiple amplification reactions to be run on single samples; however, microfluidic devices are generally difficult to manufacture and require complex valving and fluid distribution networks that have impeded their widespread application.

Moreover, in certain applications, such as intraoperation sample testing, and infectious agent and biodefense testing, it is important to employ fluidly closed reaction conditions in order to minimize the occurrence of false positive assessments. The above approaches to analyzing multiple target polynucleotides each introduce level of difficulty either by imposing compromises on the choice of reaction conditions, such that an optimal set of conditions for a reaction as a whole may not be optimal for individual targets, or by requiring access to a reaction after it has been initiated or by employing multiple ports for introducing sample, thereby multiplying chances for contamination, or like problems.

In view of these problems, it would be highly useful for applications requiring rapid amplification of multiple sequences if additional methods were available for such operations that did not have the drawbacks of the current technologies.

BRIEF SUMMARY OF THE INVENTION

The present invention provides methods and apparatus for carrying out multiple amplification reactions in a single reaction chamber by successive cycles of loading reaction mixture, amplifying, and removing spent reaction mixture in a fluidly closed reaction system. In particular, the present invention allows amplification of a plurality of target polynucleotides from a single sample by carrying out successive amplifications of different target polynucleotides from different portions of the sample.

In one aspect, the invention provides a method of controlling a plurality of sequential amplification reactions comprising the following steps: (a) amplifying a target polynucleotide in the presence of an indicator in a reaction mixture, the indicator being capable of generating an optical signal related to a quantity of an amplicon of the target polynucleotide in the amplification reaction, and the reaction mixture being disposed in a reaction chamber; (b) monitoring the optical signal of the indicator in the reaction mixture; (c) automatically removing the reaction mixture from the reaction chamber and loading the reaction chamber with a subsequent reaction mixture whenever the optical signal reaches or exceeds a predetermined level; and (d) repeating steps (a) through (c) until the plurality of amplification reactions has been carried out.

In another aspect, the invention provides a method of determining the presence or absence of a plurality of target polynucleotides in a sample comprising the following steps: (i) providing a reaction chamber selectably in fluid communication with a waste reservoir, a sample reservoir containing a sample, a first reactant reservoir containing first amplification reagents, and a second reactant reservoir containing second amplification reagents, each of the reservoirs being fluidly closed; (ii) combining a first portion of the sample and the first amplification reagents to form a first reaction mixture; (iii) subjecting the first reaction mixture to amplification reaction conditions in the reaction chamber to produce a first amplicon of one or more target polynucleotides whenever such polynucleotides are present in the sample; (iv) fluidly transferring the first reaction mixture to the waste reservoir; (v) combining a second portion of the sample and the second amplification reagents to form a second reaction mixture; and (vi) subjecting the second reaction mixture to amplification reaction conditions in the reaction chamber to produce a second amplicon of one or more target polynucleotides whenever such polynucleotides are present in the sample, wherein detection of the first and second amplicons determines the presence or absence of the plurality of target polynucleotides in the sample.

In still another aspect, the invention includes a fluidly closed reaction system for performing multiple sequential amplification reactions comprising: (i) a reaction chamber selectably in fluid communication with a sample reservoir, a waste reservoir, and a plurality of reactant reservoirs containing different amplification reagents, each of the reservoirs being fluidly closed; and (ii) a pump operationally associated with a rotary valve for performing repeated cycles of (a) fluidly transferring a portion of a sample from the waste reservoir and amplification reagents from at least one of the reactant reservoirs to the reaction chamber, wherein an amplification reaction occurs to form one or more amplicons in a reaction mixture; (b) removing the reaction mixture from the reaction chamber and fluidly transferring it to the waste reservoir after the one or more amplicons are detected.

In yet another aspect, the invention includes a computer-readable product embodying a computer executable program to control the performance of a plurality of sequential amplification reactions. The program comprising instructions for: (a) reading values of an optical signal from an amplification reaction chamber, where the signal is the most recent value of an optical signal monotonically related to a concentration of an amplicon in the amplification reaction; (b) determining a baseline signal level from the values of the optical signal; (c) computing a pre-determined value from the values of the optical signal; (d) comparing the predetermined value with the most recent value of the optical signal; and (e) repeating step (d) until the most recent value of the optical signal is equal to or greater than the predetermined level, whereupon a subsequent amplification reaction is initiated.

In still yet another aspect, the invention involves a method of determining the presence or absence of a microorganism by a plurality of amplification reactions carried out in sequence. The method comprising the steps of: (a) amplifying one or more target polynucleotides from a portion of a sample in the presence of an indicator capable of generating an optical signal related to a quantity of an amplicon of the target polynucleotide, in a reaction mixture disposed of in a reaction chamber; (b) monitoring the optical signal of the indicator in the reaction mixture; (c) automatically removing the reaction mixture from the reaction chamber and transferring a subsequent reaction mixture to the reaction chamber when the optical signal reaches or exceeds a predetermined level, otherwise automatically terminating the sequence of amplification reactions. Steps (a)-(c) are repeated until the sequence of amplification reactions are carried out or the sequence of the amplification reactions have been terminated.

In another aspect, the above methods and apparatus include embodiments the further comprising a step of, or means for, rinsing the reaction chamber after the step of fluidly transferring and/or, heating the empty reaction chamber to a DNA denaturation temperature and cooling the empty reaction chamber to a DNA annealing temperature between successive reactions.

BRIEF DESCRIPTION OF THE DRAWINGS

FIGS. 3A-3C show instrumentation protocol and results from sequential amplifications for detecting methicillin-resistant *Staphylococcus aureus* (MRSA) carried out in a Cepheid GENEXPERT™ amplification system.

FIGS. 4A-4H show instrumentation protocol and results from sequential amplifications for detecting methicillin-resistant *Staphylococcus aureus* (MRSA) carried out in a Cepheid GENEXPERT™ amplification system using non-lyophilized reagents.

FIGS. 6A-6H show instrumentation protocols and results from RT-PCRs with inter-reaction heating steps carried out in a Cepheid GENEXPERT™ amplification system.

DEFINITIONS

Figure 1A:
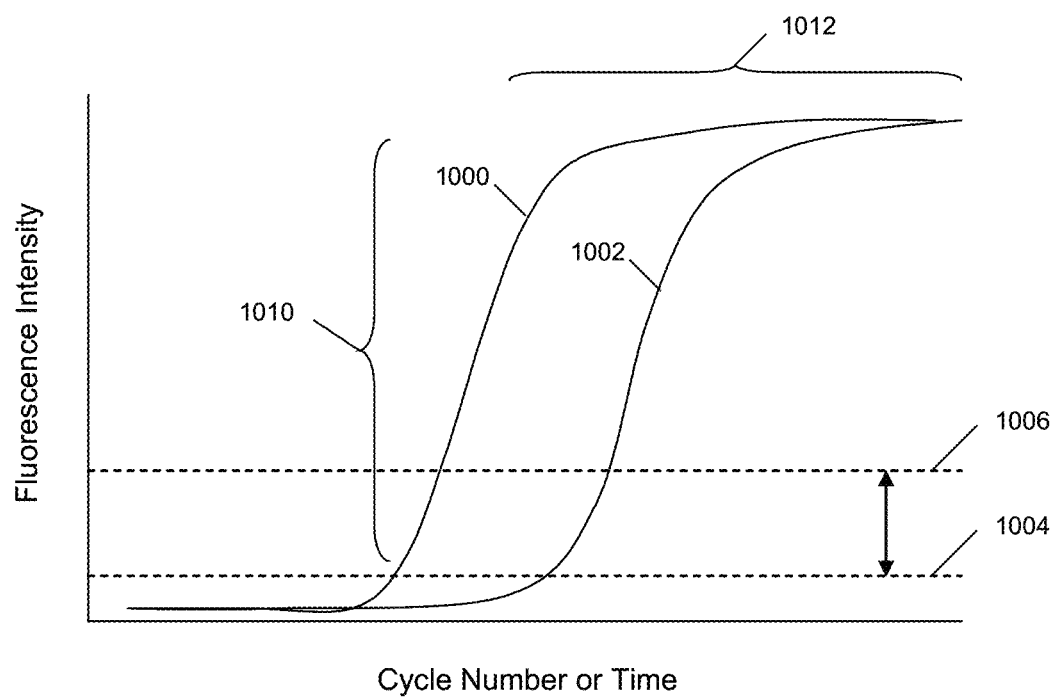
FIGS. 1A-1B illustrate signal v. cycle number (or reaction time) curves for amplification reactions, such as real-time PCRs.

Terms and symbols of nucleic acid chemistry, biochemistry, genetics, and molecular biology used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); Sambrook et al. *Molecular Cloning: A Laboratory Manual*, 2nd Edition (Cold Spring Harbor Laboratory, 1989); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, to a target sequence or its complement is required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, ligase chain reactions (LCRs), strand-displacement reactions (SDAs), nucleic acid sequence-based amplification (NASBAs), rolling circle amplifications, and the like, disclosed in the following references that are incorporated herein by reference: Mullis et al. U.S. Pat. Nos. 4,683,195; 4,965,188; 4,683,202; 4,800,159 (PCR); Gelfand et al. U.S. Pat. No. 5,210,015 (real-time PCR with "TAQMAN" probes); Wittwer et al. U.S. Pat. No. 6,174,670; Landegren et al. U.S. Pat. No. 4,988,617 ("LCR"); Birkenmeyer et al. U.S. Pat. No. 5,427,930 ("gap-LCR"); Kacian et al. U.S. Pat. No. 5,399,491 ("NASBA"); Walker, U.S. Pat. Nos. 5,648,211; 5,712,124 ("SDA"); Lizardi, U.S. Pat. No. 5,854,033; Aono et al. Japanese Patent Pub. No. JP 4-262799 (rolling circle amplification); and the like. In one aspect, amplicons of the invention are produced in a temperature-cycling amplification reaction that includes repeated steps of denaturing reaction products, usually double stranded DNA, at a first temperature, and annealing primers for polymerase extension at a second temperature. A temperature-cycling amplification reactions of special interest are PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al. *Nucleic Acids Research,* 26:2150-2155 (1998), and like references. As used herein, the term "amplifying" means performing an amplification reaction. A "reaction mixture" means a solution containing all the necessary reactants for performing a reaction, which may include, but be not limited to, buffering agents to maintain pH at a selected level during a reaction, salts, co-factors, scavengers, and the like.

"Closed" in reference to an amplification reaction means that such reaction takes place within a vessel or container or chamber that has no openings through which liquids may pass, in particular, liquids that contain non-sample materials, such as, non-sample biomolecules or organisms, including, but not limited to, nucleic acids, proteins, viruses, bacteria, or the like. In one aspect, a vessel, chamber, or container containing a closed amplification reaction may include a port or vent that is gas permeable but liquid impermeable, for example, a port that permits the venting of air through a filter membrane but not liquids under conventional reaction conditions. Suitable membranes for such ports or vents include woven polyolefin films, such as TYREK® film (DuPont), or the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

"Computer-readable product" means any tangible medium for storing information that can be read by or transmitted into a computer. Computer-readable products include, but are not limited to, magnetic diskettes, magnetic tapes, optical disks, CD-ROMs, punched tape or cards, read-only memory devices, direct access storage devices, gate arrays, electrostatic memory, and any other like medium.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Fluidly closed" means that, under conventional operating conditions, liquids within a system that comprises one or more vessels, chambers, valves, and/or passages, possibly interconnected and in communication with one another, cannot communicate with the exterior of such a system, and likewise liquids on the exterior of such a system cannot communicate with liquids contained within the interior of the system. In one aspect, conventional operating conditions means that vessels, chambers, valves, and passages of a fluidly closed system are pressurized to an extent less than 100 psi, or in another aspect, to an extent less than 50 psi, or to an extent less than 30 psi.

"Indicator" means a probe that is capable of generating an optical signal in the presence of a product of an amplification reaction (i.e. an "amplification product") such that as product accumulates in the reaction mixture the optical signal of the indicator increases, at least over a predetermined range of concentrations. The optical signals includes, but are not limited to, fluorescent signals, chemiluminescent signals, electrochemiluminescent signals, colorimetric signals, and the like. "Fluorescent indicator" means an indicator capable of generating a fluorescent signal in the presence of a product of an amplification reaction (i.e. an "amplification product") such that as product accumulates in the reaction mixture the signal of the fluorescent indicator increases, at least over a predetermined range of concentrations. Fluorescent indicators may be non-specific, such as intercalating dyes that bind to double stranded DNA products, e.g. YO-PRO-1, SYBR green 1, and the like, Ishiguro et al. *Anal. Biochem.*, 229: 207-213 (1995); Tseng et al. *Anal. Biochem.*, 245: 207-212 (1997); Morrison et al. *Biotechniques*, 24: 954-962 (1998); or such as primers having hairpin structures with a fluorescent molecule held in proximity to a fluorescent quencher until forced apart by primer extension, e.g. Whitecombe et al. *Nature Biotechnology*, 17: 804-807 (1999)("AMPLIFLUOR primers"). Fluorescent indicators also may be target sequence specific, usually comprising a fluorescent molecule in proximity to a fluorescent quencher until an oligonucleotide moiety to which they are attached specifically binds to an amplification product, e.g. Gelfand et al. U.S. Pat. No. 5,210,015 ("TAQMAN"); Nazarenko et al. *Nucleic Acids Research*, 25: 2516-2521 (1997)("scorpion probes"); Tyagi et al. *Nature Biotechnology*, 16:49-53 (1998) ("molecular beacons"). Fluorescent indicators may be used in connection with real-time PCR, or they may be used to measure the total amount of reaction product at the completion of a reaction.

"Internal standard" means a nucleic acid sequence that is amplified in the same amplification reaction as a target polynucleotide in order to permit absolute or relative quantification of the target polynucleotide in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al. *Mol. Cell Probes*, 15:307-311 (2001). Exemplary reference sequences include, but are not limited to, sequences from the following genes: GAPDH, β2-microglobulin, 18S ribosomal RNA, and β-actin (see also, Selvey et al., supra).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al. U.S. Pat. No. 4,883,750; Letsinger et al. U.S. Pat. No. 5,476,930; Fung et al. U.S. Pat. No. 5,593,826; Kool, U.S. Pat. No. 5,426,180; Landegren et al. U.S. Pat. No. 5,871,921; Xu and Kool, *Nucleic Acids Research*, 27:875-881 (1999); Higgins et al. *Methods in Enzymology*, 68:50-71 (1979); Engler et al. *The Enzymes*, 15:3-29 (1982); and Namsaraev, U.S. Patent Publication No. 2004/0110213.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, and a detection system. Microfluidics may further include valves, pumps, and specialized functional coatings on their interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al. U.S. Pat. Nos. 5,126,022 and 6,054,034; Nelson et al. U.S. Pat. No. 6,613,525; Maher et al. U.S. Pat. No. 6,399,952; Ricco et al. Int'l Patent Publication No. WO 02/24322; Bjornson et al. Int'l Patent Publication No. WO 99/19717; Wilding et al. U.S. Pat. Nos. 5,587,128; 5,498,392; Sia et al. *Electrophoresis*, 24:3563-3576 (2003); Unger et al. *Science*, 288:113-116 (2000); Enzelberger et al. U.S. Pat. No. 6,960,437.

"Nucleic acid sequence-based amplification" or "NASBA" is an amplification reaction based on the simultaneous activity of a reverse transcriptase (usually avian myeloblastosis virus (AMV) reverse transcriptase), an RNase H, and an RNA polymerase (usually T7 RNA polymerase) that uses two oligonucleotide primers, and which under conventional conditions can amplify a target sequence by a factor in the range of $10^9$ to $10^{12}$ in 90 to 120 minutes. In a NASBA reaction, nucleic acids are a template for the amplification reaction only if they are single stranded and contain a primer binding site. Because NASBA is isothermal (usually carried out at 41° C. with the above enzymes), specific amplification of single stranded RNA may be accomplished if denaturation of double stranded DNA is prevented in the sample preparation procedure. That is, it is possible to detect a single stranded RNA target in a double stranded DNA background without getting false positive results caused by complex genomic DNA, in contrast with other techniques, such as RT-PCR. By using fluorescent indicators compatible with the reaction, such as molecular beacons, NASBAs may be carried out with real-time detection of the amplicon. Molecular beacons are stem-and-loop-structured oligonucleotides with a fluorescent label at one end and a quencher at the other end, e.g. 5'-fluorescein and 3'-(4-(dimethylamino)phenyl)azo) benzoic acid (i.e., 3'-DABCYL), as disclosed by Tyagi and Kramer (cited above). An exemplary molecular beacon may have complementary stem strands of six nucleotides, e.g. 4 G's or C's and 2 A's or T's, and a target-specific loop of about 20 nucleotides, so that the molecular beacon can form a stable hybrid with a target sequence at reaction temperature, e.g. 41° C. A typical NASBA reaction mix is 80 mM Tris-HCl [pH 8.5], 24 mM $MgCl_2$, 140 mM KCl, 1.0 mM DTT, 2.0 mM of each dNTP, 4.0 mM each of ATP, UTP and CTP, 3.0 mM GTP, and 1.0 mM ITP in 30% DMSO. Primer concentration is 0.1 μM and molecular beacon concentration is 40 nM. Enzyme mix is 375 mM sorbitol, 2.1 μg BSA, 0.08 U RNase H, 32 U T7 RNA polymerase, and 6.4 U AMV reverse transcriptase. A reaction may comprise 5 μL sample, 10 μL NASBA reaction mix, and 5 μL enzyme mix, for a total reaction volume of 20 μL. Further guidance for carrying out real-time NASBA reactions is disclosed in the following references that are incorporated by reference: Polstra et al. *BMC Infectious Diseases,* 2:18 (2002); Leone et al. *Nucleic Acids Research,* 26:2150-2155 (1998); Gulliksen et al. *Anal. Chem.,* 76:9-14 (2004); Weusten et al. *Nucleic Acids Research,* 30(6) e26 (2002); Deiman et al. *Mol. Biotechnol.,* 20:163-179 (2002). Nested NASBA reactions are carried out similarly to nested PCRs; namely, the amplicon of a first NASBA reaction becomes the sample for a second NASBA reaction using a new set of primers, at least one of which binds to an interior location of the first amplicon.

"Nucleoside" as used herein includes the natural nucleosides, including 2'-deoxy and 2'-hydroxyl forms, e.g. as described in Kornberg and Baker, *DNA Replication,* 2nd Ed. (Freeman, San Francisco, 1992). "Analogs" in reference to nucleosides includes synthetic nucleosides having modified base moieties and/or modified sugar moieties, e.g. described by Scheit, *Nucleotide Analogs* (John Wiley, New York, 1980); Uhlman and Peyman, *Chemical Reviews,* 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al. *Exp. Opin. Ther. Patents,* 6:855-870 (1996); Mesmaeker et al. *Current Opinion in Structural Biology,* 5:343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al. editors, *PCR: A Practical Approach* and *PCR: A Practical Approach, 2nd Ed.* (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al. U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al. U.S. Pat. No. 5,210,015 ("TAQMAN"); Wittwer et al. U.S. Pat. Nos. 6,174,670 and 6,569,627 (intercalating dyes); Tyagi et al. U.S. Pat. No. 5,925,517 (molecular beacons); each of which is hereby incorporated by reference. Detection chemistries for real-time PCR are reviewed in Mackay et al. *Nucleic Acids Research,* 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. *Anal. Biochem.,* 273:221-228 (1999)(two-color real-time PCR). Usually, distinct sets of primers are employed for each sequence being amplified. Typically, the number of target sequences in a multiplex PCR is in the range of from 2 to 10, or from 2 to 6, or more typically, from 2 to 4.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β2-microglobulin, ribosomal RNA, and the like. Techniques for quantitative PCR are well-known to those of ordinary skill in the art, as exemplified in the following references that are incorporated by reference: Freeman et al, *Biotechniques,* 26:112-126 (1999); Becker-Andre et al.

*Nucleic Acids Research,* 17:9437-9447 (1989); Zimmerman et al. *Biotechniques,* 21:268-279 (1996); Diviacco et al. *Gene,* 122:3013-3020 (1992); Becker-Andre et al. *Nucleic Acids Research,* 17:9437-9446 (1989); and the like.

"Polynucleotide" and "oligonucleotide" are used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics,* 2nd Ed. (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al. *Molecular Cloning, Second Edition* (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, *PCR Primer: A Laboratory Manual,* 2nd Edition (Cold Spring Harbor Press, New York, 2003).

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like. Likewise, a readout of a real-time PCR can be one or more fluorescent intensity signals within specified frequency bands as functions of time, or other reaction parameter related to time.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Tm" or "melting temperature" means the temperature at which a population of double-stranded nucleic acid molecules becomes half dissociated into single strands. Several equations for calculating the Tm of nucleic acids are well known in the art. For example, a simple estimate of the Tm value may be calculated by the equation. Tm=81.5+0.41 (% G+C), when a nucleic acid is in aqueous solution at 1 M NaCl. Methods for calculating Tm based on more complete models of duplex formation and dissociation are found in Breslauer et al. *Proc. Natl. Acad. Sci.,* 83:3746-3750 (1986); and Wetmur, *Crit. Rev. Biochem. Mol. Biol.,* 26:227-259 (1991).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al. pages. 21-76, in *Flow Cytometry: Instrumentation and Data Analysis* (Academic Press, New York, 1985).

DETAILED DESCRIPTION OF THE INVENTION

The practice of the present invention may employ, unless otherwise indicated, conventional techniques and descriptions of organic chemistry, polymer technology, molecular biology (including recombinant techniques), cell biology, biochemistry, and analytical instrumentation, which are within the skill of the art. Such conventional techniques include fluorescence measurement, optical signal collection, instrumentation control, data analysis, electronics, mechanical engineering, fluid handling, and the like. Specific illustrations of suitable techniques can be had by reference to the examples herein below. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), as well as other treatises and guides cited below.

The invention is directed to systems, methods and apparatus for carrying out multiple reactions, usually amplification reactions, such as PCRs, in a single reaction chamber, especially under fluidly closed conditions. In one aspect, a sequence of reactions is employed to amplify and detect different target polynucleotides from the same biological sample. Such reactions are usually amplification reactions, but may also include other reaction types, such as sample processing reactions, including, for example, reverse transcription reactions to convert RNA sequences into cDNA sequences, or the like. In another aspect, such methods are carried out in a fluidly closed reaction system by the following steps: (i) mixing a portion of a sample with amplification reagents to form a reaction mixture; (ii) amplifying in the reaction chamber one or more target polynucleotides to form one or more amplicons in the reaction mixture; (iii) detecting the one or more amplicons to determine the presence or absence of the one or more target polynucleotides in the sample; (iv) removing the reaction mixture from the reaction chamber after detection; and (v) repeating steps (i) through (iv) until the presence or absence of the plurality of target polynucleotides is determined. In the step of mixing, the sample portion and the amplification reagents may be combined and mixed in a reagent reservoir after which they are fluidly transferred to the reaction chamber for amplification. Alternatively, the sample portion and the amplification reagents may be combined and mixed in the reaction chamber directly.

In one aspect, the plurality of amplification reactions of a method of the invention is in the range of from 2 to 20, inclusive; in another aspect, the plurality is in the range of from 2 to 10, inclusive; and in another aspect, the plurality is in the range of from 2 to 3, inclusive. In a preferred embodiment, two amplification reactions are implemented by methods of the invention. As exemplified further below, typically a fluidly closed reaction system is prepared with, or provided with (in case of commercial reactors), amplification reagents pre-loaded, usually in lyophilized form, in distinct reservoirs, e.g. one for each amplification reaction performed. The one or more target polynucleotides sought to be amplified in each reaction can include one or more reference sequences, or internal standards, as positive controls. Preferably, amplicons are detected and monitored in real time using one or more indicators, as described below. In particular, in embodiments with feedback control of the timing of reaction termination and initiation, real-time amplification reactions are employed. In a preferred embodiment, at the termination of a reaction, the reaction mixture is removed from the reaction chamber and transferred to a waste reservoir. Usually, the same waste reservoir can be used for each amplification reaction. In one embodiment, the waste reservoir contains, or can be loaded with, reagents to neutralize, secure, or otherwise render the amplification waste and/or reaction chamber rinses safe for handling and transport. Such reagents include, but are not limited to, disinfectants, fungicides, bactericides, neutralizing buffers, liquid absorbing compounds, and the like. Exemplary compounds for absorbing aqueous compounds include, but are not limited to, hydrolyzed starch, polyacrylonitrile, and sodium polyacrylate (e.g. —[CH2-CH(C(=O)ONa)]n-).

In another aspect, the invention provides a method for automated control of a sequence of amplification reactions that is implemented with the following steps: (i) amplifying one or more target polynucleotides from a portion of a sample in the presence of an indicator in a reaction mixture, the indicator being capable of generating an optical signal related to a quantity of an amplicon of the target polynucleotide in the amplification reaction, and the reaction mixture being disposed in a reaction chamber; (ii) monitoring the optical signal of the indicator in the reaction mixture; (iii) automatically removing the reaction mixture from the reaction chamber and transferring to the reaction chamber with a subsequent reaction mixture whenever the optical signal reaches or exceeds a predetermined level; and (iv) repeating steps (i) through (iii) until the sequence of amplification reactions has been carried out. This aspect further contemplates the automatic termination of a sequence of reactions based on current reaction results. Such embodiments are particularly useful where rapid production of test results, especially negative test results, is highly desirable. For example, related microorganisms frequently exist in both benign as well as pathogenic strains, wherein the pathogenic strains may be identified by a particular genetic element, e.g. a plasmid containing a gene that confers pathogenicity.

Consequently, tests for a pathogenic strain of a microorganism frequently involve two or more steps, where a first step of the test determines the presence or absence of any member of a genus or species of the microorganism, followed by one or more successive tests that identify a particular pathogenic form. In such sequential tests, it is advantageous to terminate the test whenever the result of a particular step indicates the absence of the pathogenic strain. For example, a sequential test may be conducted for *Staphylococcus aureus* (SA) methicillin-resistant strain that comprises a first step of amplifying and detecting a conserved SA gene sequence and a second step of amplifying and detecting a segment of the mecA gene, which is largely responsible for methicillin resistance. Accordingly, an embodiment of the above form of the invention provides a method for identifying an organism by a plurality of amplification reactions carried out in sequence, wherein at least the first amplification reaction determines the presence or absence of a genus or species and subsequent reaction(s) determine a specific strain. After each amplification reaction a decision is made automatically as to whether to terminate or to continue on to the next test. Such an embodiment is implemented with the following steps: (i) amplifying one or more target polynucleotides from a portion of a sample in the presence of an indicator in a reaction mixture, the indicator being capable of generating an optical signal related to a quantity of an amplicon of the target polynucleotide in the amplification reaction, the reaction mixture being disposed in a reaction chamber; (ii) monitoring the optical signal of the indicator in the reaction mixture; (iii) automatically removing the reaction mixture from the reaction chamber and transferring to the reaction chamber with a subsequent reaction mixture whenever the optical signal reaches or exceeds a predetermined level, otherwise automatically terminating the sequence of amplification reactions; and (iv) repeating steps (i) through (iii) until the sequence of amplification reactions has been carried out or the sequence of amplification reactions has been terminated. In both of the above aspects of the invention, the step of removing a reaction mixture from the reaction chamber includes a step of rinsing the reaction chamber with a wash solution. The used wash solution, i.e. the "rinsate," may be fluidly transferred to a waste reservoir prior to a subsequent reaction.

In another aspect of the inventions, problems are addressed which are associated with foaming and bubble formation caused by transferring reaction mixtures into and out of a reaction chamber. It is highly desirable to avoid the formation of bubbles or foams in analytical instruments as their presence can frequently degrade sensitivity and lead to the generation of spurious signals, particularly in the detection or quantification of fluorescent analytes or probes in a liquid phase, e.g. Jekelis (2005), *Biomed Instrum Technol*, 39:232-236. It has been discovered that the formation of foam or bubbles is reduced or eliminated in a reaction chamber of the invention by heating the empty reaction chamber after removal of a reaction mixture and prior to the loading of a subsequent reaction mixture. Accordingly, in one aspect of the invention, between successive reactions the reaction chamber is purged of all liquid by transferring air into the chamber (either by aspiration, i.e. sucking fluid out, or by dispensing, i.e. forcing fluid in) and is heated for a period of time immediately prior to loading a successive reaction mixture. The purging and heating steps may be carried out successively or may be carried out such that they overlap in time. In a preferred aspect, the steps are carried out successively wherein the reaction chamber is first purged by transferring air into it, after which it is heated. In one aspect, the heating step is implemented in two phases, wherein the chamber is heated to a first temperature and held for a first interval of time followed by changing to a second temperature which is held for a second interval of time. In one aspect, the first temperature is approximately DNA denaturation temperature, which is usually in the range of from 85° C. to 100° C., or in the range of from 92° C. to 99° C., and the first interval is from 0.5 s to 10 s, or from is to 3 s; and the second temperature is approximately DNA annealing temperature, which is usually in the range of from 35° C. to 75° C., or in the range of from 45° C. to 72° C., and the second interval is from 0.5 s to 10 s, or from is to 3 s. In another aspect, the first temperature is in the range of from 94° C. to 96° C. and the first interval is from 0.5 s to 2 s; and the second temperature is in the range of from 45° C. to 70° C. and the second interval is from is to 2 s. In one aspect, all of the methods described above have embodiments wherein they further include a step of heating the empty reaction chamber to a DNA denaturation temperature for a period of time in the indicated ranges. In a further aspect, such heating step is followed by a cooling step wherein the empty reaction chamber is cooled to a DNA annealing temperature prior to fluidly transferring a subsequent reaction mixture to the reaction chamber.

In another aspect of the invention, an apparatus is provided for conducting a sequence of amplification reactions using different portions, usually aliquots, of a single sample under fluidly closed conditions. In one embodiment such an apparatus comprises: a) a body having at least first and second channels formed therein; and b) a reaction vessel extending from the body, the reaction vessel having: i) a reaction chamber for receiving liquid; ii) an inlet port connected to the reaction chamber via an inlet channel; and iii) an outlet port connected to the reaction chamber via an outlet channel, wherein the inlet port of the vessel is connected to the first channel in the body and wherein the outlet port of the vessel is connected to the second channel in the body. The apparatus of the invention further includes a vent in fluid communication with the second channel for venting gas from the second channel. The apparatus of the invention further comprises a differential pressure source for forcing fluid in the first channel in the body to flow through the inlet port of the vessel and into the reaction chamber. The vessel of the invention further includes: i) a rigid frame defining side walls of the reaction chamber; and ii) first and second polymeric films attached to opposite sides of the rigid frame to form opposing major walls of the reaction chamber. The body of the apparatus further includes a mixing chamber for mixing a fluid sample with amplification reagents, the mixing chamber being connected to the inlet port of the vessel via the first channel. The body of the apparatus further includes a waste chamber, or reservoir, for receiving the remainder of the liquid removed through the outlet channel, the waste chamber being connected to the outlet port of the vessel via the second channel. The body of the apparatus further has formed therein: i) a sample flow path; and ii) a separation region in the sample flow path for separating a desired analyte from a fluid sample, the separation region being connected to the inlet port of the vessel via the first channel. In one aspect, the separation region in the body comprises: a) a lysing chamber in the sample flow path for lysing cells or viruses in the sample to release material therefrom; and b) at least one solid support positioned in the lysing chamber for capturing the cells or viruses to be lysed. The vessel of the apparatus includes a plurality of walls defining the reaction chamber, at least one of the walls comprising a flexible sheet or film, and the apparatus further comprises: a) at least one thermal surface for contacting the sheet or film; b) means for increasing the pressure in the reaction chamber, wherein the pressure increase in the chamber is sufficient to force the sheet or film to conform to the thermal surface; and c) at least one thermal element for heating or cooling the surface to induce a temperature change within the chamber.

The vessel of the apparatus further includes two opposing major walls and sidewalls connecting the major walls to each other to form the reaction chamber, at least two of the side walls are optically transmissive and angularly offset from each other, and the apparatus further comprises an optics system having at least one light source for transmitting light to the reaction chamber through a first one of the optically transmissive side walls and having at least one detector for detecting light emitted from the chamber through a second one of the optically transmissive side walls.

As disclosed more fully in the specific example below, such apparatus is preferably operated under fluidly closed conditions wherein fluids and reagents are moved by way of one or more valves and pumps that can create differential pressures on such fluids and reagents under programmed control. Of particular interest is the use of a piston-type pump in operational association with a rotary valve that permits chambers and/or reservoirs to be selectably placed in fluid communication for transferring fluids and reagents to desired locations. As described more fully below, the operation of such pumps and valves is controlled by a microprocessor using conventional techniques. Such microprocessor may also receive data from one or more detectors that monitor optical signals from reaction products in the reaction chamber and on the basis of such data transmit control signals to the pumps and valves of the apparatus to terminate reactions, initiate reactions, initiate rinse steps, and the like.

Sequential Amplification Reactions

In one aspect, sequential amplification reactions of the invention are a plurality of separate amplifications of different target polynucleotides from the same sample, which take place in the same reaction chamber of a fluidly closed reaction system. A feature of the invention is the metering of portions of a single sample into a reaction chamber under fluidly closed reaction conditions. In one aspect, portions of a sample used in the separate amplifications may be equal in volume, or they may be unequal, and the plurality of portions used may comprise the entire sample (i.e. they may be aliquots of a sample) or it may comprise a part of the sample (i.e. they may be aliquants of a sample). There is abundant guidance in the literature, as evidenced by the citations in the Definitions section, for assisting those of ordinary skill in the art for making routine design choices for creating individual amplification reactions for the invention, including, but not limited to, the following: (i) the number of cycles or durations of each stage; (ii) where amplification cycles are under automated control, selection of predetermined signal levels for deciding to terminate a current reaction and to advance to the next reaction; (iii) the relative portions of a sample to be included with each reaction in a sequence; (iv) the number and identities of target polynucleotides to be detected in each amplification reaction; (v) lengths and sequences of primers for each amplification reaction; (vi) whether reference sequences should be amplified in each reaction; (vii) the types of indicators to be used in each amplification reaction; (viii) whether the same kind of amplification reaction should be run in each stage, e.g. for two-amplification reactions: PCR-PCR, NASBA-NASBA, PCR-NASBA, and the like. Usually amplification reactions are either successive PCRs or successive NASBA reactions and are carried out under conventional reaction conditions. Usually, the same indicators are used in each amplification reaction of a sequence.

As mentioned above, each amplification reaction occurs in a reaction mixture comprising a portion of a sample and amplification reagents. Selecting the size of a portion for a particular amplification reaction is a design choice of one of ordinary skill that depends on factors such as (i) the nature (e.g. sequence, susceptibility of forming secondary structures, etc.) of the target polynucleotides, (ii) the expected concentration or amount of target polynucleotide, (iii) the concentrations and nature of the amplification reagents, and the like. As above, there is abundant guidance for those of ordinary skill in the art for making such routine design choices, as evidenced by the public literature on the application of amplification reactions in the life sciences field. Generally, an effective portion of a sample is mixed with amplification reagents to form a reaction mixture. In one aspect, an effective portion is an amount sufficient to permit the initiation of an amplification reaction. In another aspect, an effective portion is an amount sufficient to provide in a reaction mixture a target concentration of at least 1 target polynucleotide per or in another aspect, at least 10 target polynucleotides per µL, or in another aspect, at least 50 target polynucleotides per µL, or in another aspect at least 100 target polynucleotides per µL, or in another aspect, at least 500 target polynucleotides per µL, or in another aspect, at least 1000 target polynucleotides per µL. In still another aspect, an effective portion is an amount that is from 0.5 to 50 percent of the volume of the sample, or an amount that is from 10 to 50 percent of the volume of the sample.

In a further aspect, the invention provides methods of conducting reverse transcriptase reactions in series with a multi-stage amplification reaction. In one embodiment, a plurality of RNA sequences, such as selected mRNAs extracted from a cell or tissue sample, may be amplified as follows: (i) transcribing with reverse transcription reagents RNA sequences, for example, in a fluidly closed reaction system, to form a sample of complementary single stranded target polynucleotides; (ii) transferring a portion of the sample and amplification reagents to a reaction chamber to form a reaction mixture; (iii) amplifying in the reaction mixture at least one target polynucleotide from the portion in the presence of a fluorescent indicator, the fluorescent indicator being capable of generating an optical signal related to a quantity of an amplicon in the reaction mixture; (iv) monitoring the optical signal of the fluorescent indicator; and (v) removing the reaction mixture from the reaction chamber and initiating a subsequent amplification reaction whenever the optical signal reaches or exceeds a predetermined level, and (vi) repeating steps (ii) through (v) until the absence, presence, and/or quantity of each target polynucleotide of the plurality is determined. The step of transcribing is carried out with a conventional reverse transcriptase reaction, components of which, i.e. reverse transcriptase reagents (a reverse transcriptase, nucleoside triphosphates, reaction buffer), are readily available commercially, e.g. Ambion, Inc. In one aspect, the above aspect of the invention is performed in a fluidly closed reaction system.

Control of Sequential Amplifications

In one aspect, the invention provides a method for automatically terminating and/or initiating successive amplification reactions, either under open-loop control, or closed-loop control based on real-time measurements of certain reaction parameters. In embodiments with open-loop control, an amplification reaction is carried out for a predetermined number of cycles or for a predetermined reaction time, after which the reaction is terminated, e.g. simply by removing the reaction mixture from the reaction chamber, an effective portion of the sample is mixed with appropriate amplification reagents to form a new reaction mixture, the new reaction mixture is loaded into the reaction chamber, and a timed program of temperatures is selected to carry out an amplification reaction. Optionally, after a current reaction mixture is removed from the reaction chamber and transferred to the waste reservoir, the reaction chamber can be rinsed to further remove traces of the current reaction mixture remaining in the chamber. Such rising is accomplished by carrying out one or more cycles of transferring wash solution from a wash solution reservoir to the reaction chamber and transferring the wash solution in the reaction chamber, or rinsing, to the waste reservoir. Wash solutions can be water, or it can be water mixed with other reagents such as detergents, nucleases, or the like, that are added for the purpose of reducing spurious signals generated by material left over from a previous amplification reaction.

In embodiments with closed-loop control, a reaction parameter of an amplification reaction is monitored and when it takes on a predetermined value, or crosses a predetermined threshold value, the reaction is stopped, at least an effective portion of the sample is mixed with appropriate amplification reagents, and a subsequent amplification reaction is initiated. The reaction parameter used for determining when to initiate a successive amplification may be any parameter that has a well-defined relationship with the accumulation of reaction products, or in other words, with the degree of completion of a reaction. Preferably, the reaction parameter has a monotonic relationship with the accumulation of one or more products in a reaction, so that increasing values of the parameter may be either positively or negatively correlated with the amount(s) of such products, which are usually one or more amplicons. Reaction parameters may include, but are not limited to, optical density of the reaction mixture; temperature; pH; concentration of secondary reaction products; amplicon concentration, the latter, for example, being based on one or more fluorescent signals, colorimetric signals, chemiluminescent signals, electrochemiluminescent signals, or electrochemical signals; and the like. In one aspect, a reaction parameter is monotonically related to the concentration of at least one amplicon an amplification reaction. Such an amplicon may be produced from a target polynucleotide, or a reference sequence or other internal standard. Thus, in a sequence of PCRs with closed-loop control, the amplification reactions are real-time PCRs. In one aspect of the invention, the reaction parameter is an amplicon detected by a fluorescent indicator whose signal is monotonically related to the concentration of the amplicon in the reaction mixture. Where there is variability in the amount or quality of target polynucleotide in a sample or specimen, closed-loop control of the reactions can produce more consistent and less variable readouts.

Since in some applications, a sample may or may not contain a target polynucleotide of interest. Thus, in one aspect, the amplicon of one or more reference sequences, or other internal standard, is monitored for determining when to initiate successive reactions. That is, such an internal standard serves as a positive control and reaction parameter for initiating a successive reaction. In another aspect, both amplicons of an internal standard and of a target polynucleotide must reach or exceed predetermined levels, which may be the same or different, in order to initiate a successive reaction.

In another aspect of the invention, when an amplification reaction is a PCR under open-loop control, the number of cycles carried out prior to initiation of the next reaction is in the range of between 20 and 40, or in another aspect, in the range of between 20 and 30. In another aspect, when a current amplification reaction is stopped and a subsequent amplification reaction is initiated after a predetermined time, the predetermined time may be selected empirically for the particular type of sample that is being analyzed. For example, in samples having reference sequences, a predetermined time may be selected as the average time it takes to amplify a selected reference sequence to some fraction, e.g. quarter, third, half, or the like, of its plateau value in an average sample.

In one aspect, such automatic termination of one reaction and initiation of a subsequent amplification reaction is under closed-loop control. That is, amplification reactions of the invention are preferably carried out in apparatus that permit parameters associated with multiple classes of amplicons to be monitored. Such parameters include, but are not limited to, fluorescent signals generated by different fluorescent indicators associated with each of at least two (and usually three) different target polynucleotides. Such monitoring includes collecting signals, converting them into digital form, processing the digital information in a processor to determine whether to terminate a current reaction and to initiate a subsequent reaction, and generating control signals to implement such changes. Instrumentation for carrying out such functions is well known in the art, as evidence by the following standard references: Lakowicz, *Principles of Fluorescence Spectroscopy*, 2nd edition (Springer, 1999); Johnson, *Photodetection and Measurement* (McGraw-Hill Professional, 2003); Sharma et al. *Introduction to Fluorescence Spectroscopy* (Wiley-Interscience, 1999); Sokoloff, *Applications in Labview* (Prentice Hall, 2003); and the like.

Figure 1B:
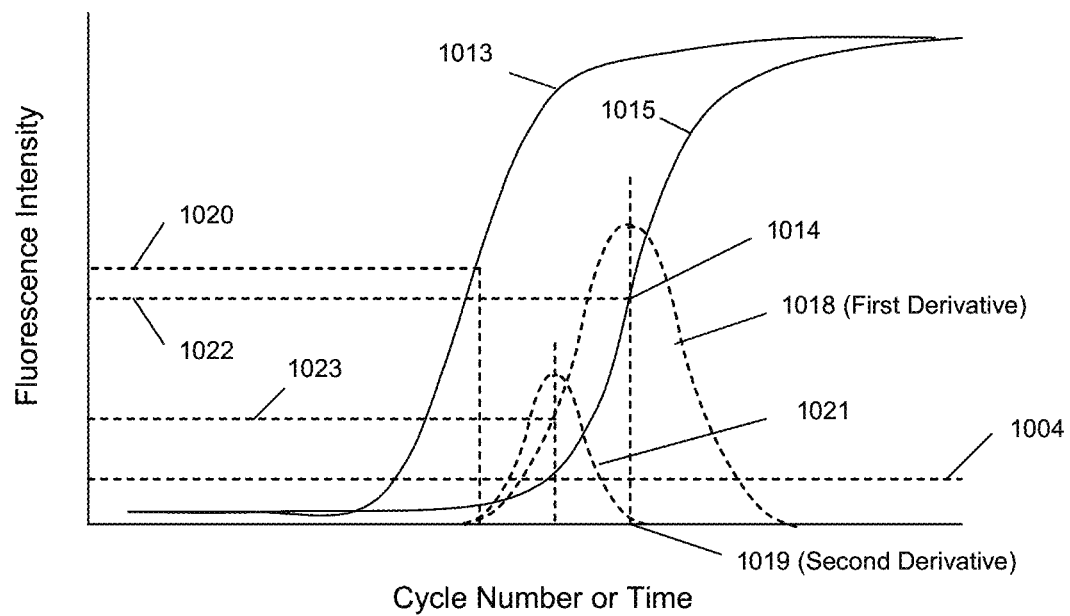

When amplification reactions are under closed-loop control, the value of the reaction parameter at which a subsequent reaction is initiated may be selected in a variety of ways. In one aspect, the value is determined as a function of a baseline signal level, or background noise, value, or as a characteristic of a function that describes the accumulation of one or more amplicons in the reaction mixture, as illustrated in FIGS. 1A and 1B. In FIG. 1A, curves (1000) and (1002) represent accumulated amplicon of, for example, a reference sequence and target polynucleotide, respectively, as determined by two different fluorescent signals generated by amplicon-specific probes, e.g. molecular beacons having fluorescent dyes that emit fluorescence at distinguishable wavelengths. Such curves are typically sigmoid as illustrated, each having a region of low positive slope below a noise level, or baseline signal, (1004), a log-linear region (1010) of high positive slope, and a plateau region (1012) of low positive slope that corresponds to the stage in the reaction where reactants become exhausted and/or interfering side products accumulate. In one aspect of the invention, a subsequent reaction is initiated when curve (1002) of the target amplicon reaches or exceeds a predetermined level (1006), which may be a function of baseline signal (1004). In another aspect, a subsequent reaction is initiated when both curve (1002) of the target amplicon and curve (1000) of a reference sequence both reach or exceed a predetermined level (1006). Selection of predetermined level (1006) is a routine design choice for one of ordinary skill in the art that may depend on a variety of factors, e.g. the likelihood of sequences closely related to the target being amplified in the reaction (i.e. lack of specificity in an assay), the quality of the sample and the extent to which it contributes to the baseline signal value, the type of amplification reaction used, the signal detection system employed, and the like. In one aspect, predetermined level (1006) is a multiple of baseline signal value (1004). By way of example, predetermined level (1006) may be selected from a range between 1.5 and 25 times a baseline signal value. In another aspect, predetermined level (1006) is 1.5 times the baseline signal value, or 2 times the baseline signal value, or 3 times the baseline signal value, or 5 times the baseline signal value, or 10 times the baseline signal value. A baseline signal value may be a function, e.g. an average, of fluorescent measurements of a predetermined number of cycles, or for a predetermined time interval, near the beginning of an amplification reaction. The fluorescent measurements may be, or include, measurements of signals from the same channel as that for the fluorescent signal generated by the amplicon being monitored. In one aspect, a baseline signal value is a function of the initial 10, or 25, or 50, or 100 optical signal values measured for at least one amplicon growth curve. In one aspect, such function is an arithmetic average of such initial optical signal values. Preferably, predetermined level (1006) intersects curve (1002) and/or curve (1000) in their respective log-linear regions (1010). Amplicons may be identified and/or measured with a variety of labels that generate optical signals, including but not limited to fluorescent indicators, colorimetric labels, chemiluminescent labels, electrochemiluminescent labels, and the like.

In another aspect, the value of a reaction parameter at which a subsequent reaction is initiated may be determined by a characteristic of a curve describing the relationship of an accumulated amplicon and cycle number or time in an amplification reaction, as illustrated in FIG. 1B (referred to herein as an "amplicon growth curve"). As in FIG. 1A, curve (1013) and curve (1015) describe the accumulation of amplicons corresponding to a reference sequence and a target polynucleotide, respectively. Both curves at each point have positive slopes, however, the magnitude of the slopes changes from early in the reaction to late in the reaction, with the slopes being flat in the beginning, steep in the log-linear region, and flat again in the plateau region. If the derivative is taken of such a curve, a roughly symmetrical function (1018) is produced that has a maximum at time or cycle value (1019). Value (1019) is a root of the first derivative of curve (1015). Value (1019) corresponds to the point (1014) at which the slope of curve (1015) stops increasing and starts decreasing, that is, it is an inflexion point, which is located in approximately the middle of the log-linear region, which makes it an attractive characteristic of curve (1015) for determining a signal value (1022) at which to initiate a subsequent reaction. In another aspect, a second derivative of curve (1015) may be determined to produce another roughly symmetrical function illustrated by curve (1021). The root of curve (1021) provides another candidate characteristic for determining a signal value, e.g. (1023), at which to initiate a subsequent reaction. Determination of signal values corresponding to such characteristics of curves (1015) describing the accumulation of amplicon is disclosed in McMillan et al. U.S. Pat. No. 6,783,934, which is incorporated herein by reference. As mentioned above, the term "amplicon growth curve" means a curve, such as curves (1000), (1002), (1013), or (1015), that describes the accumulation of amplicon in a reaction mixture as a function of cycle number or time, or as a function of a related parameter, e.g. temperature in a non-temperature regulated amplification reaction, or the like. It is understood that characteristics, such as first or second derivatives, of amplicon growth curves are repeatedly computed during an assay as data making up the curve is collected. It is also understood that because of the real-time nature of the above assays, it may only be possible to determine certain characteristics of an amplicon growth curve retrospectively; thus, such characteristics may not be suitable in every situation for determining when a subsequent amplification reaction should be initiated. Selecting an appropriate characteristic of an amplicon growth curve for determining when to initiate a subsequent amplification reaction is a routine design choice for one of ordinary skill in the art.

Figure 1C:
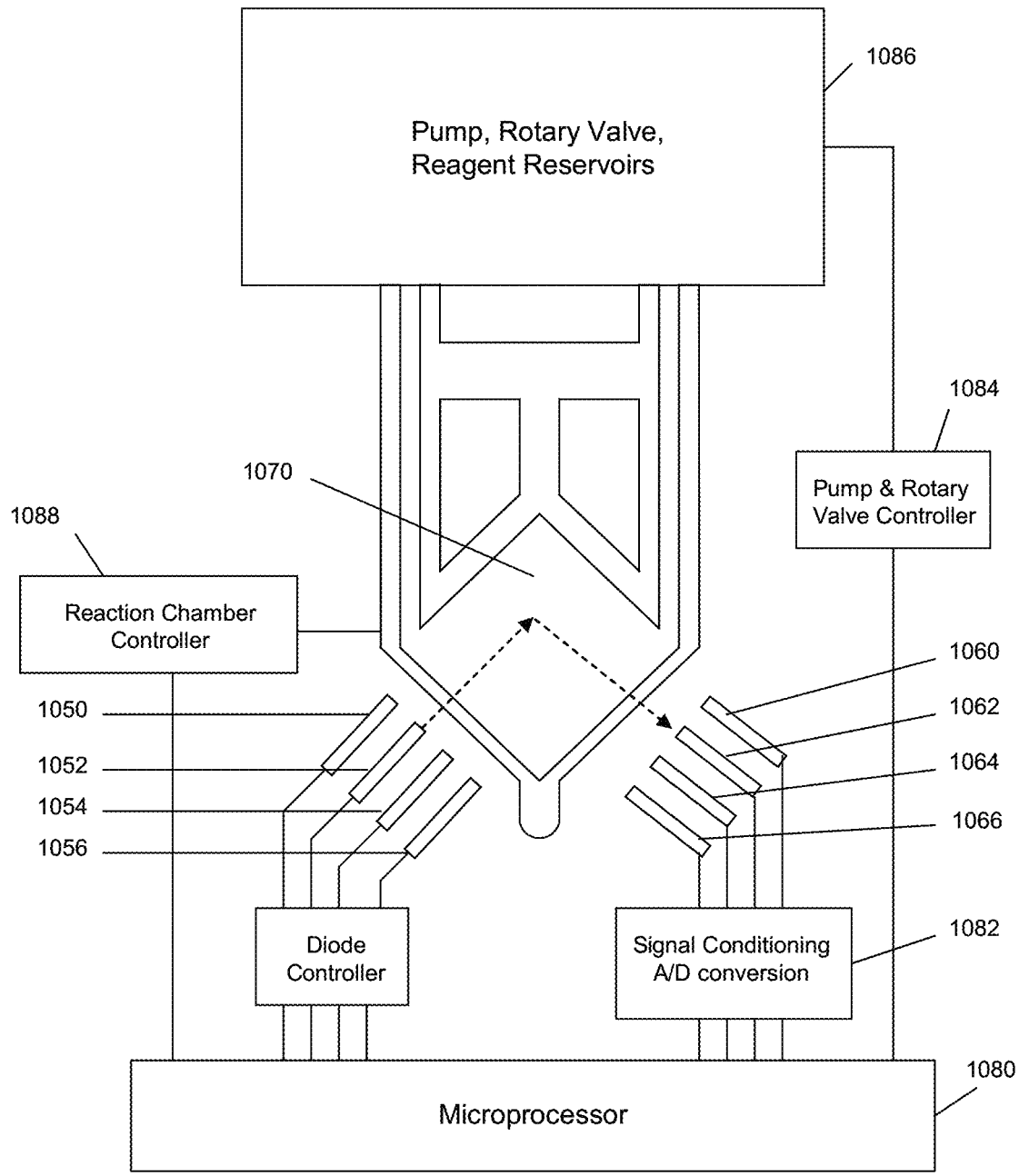
FIG. 1C is a diagram of an apparatus for implementing methods of the invention.

In one aspect of the invention, closed-loop control of initiation of a subsequent reaction is implemented by detecting an optical signal corresponding to a reaction parameter that reaches or exceeds a predetermined value. Preferably, the reaction parameter is concentration of an amplicon, usually the amplicon corresponding to a target polynucleotide. A variety of fluorescent signal generating schemes are available for producing a fluorescent signal in an amplification reaction that is monotonically related to amplicon concentration. such fluorescent signal generating schemes include, but are not limited to, molecular beacons, intercalating dyes, such as SYBR green, TAQMAN™ probes, AMPLIFLUOR primers, "scorpion" primers, and the like, which are disclosed in references cited above. A variety of instrumentation systems may be employed to carry out such closed-loop control based on an optical signal generated by a reaction parameter, such as amplicon concentration. As described more fully below, in one aspect, a multichannel optical detection system disclosed by Christel et al. U.S. Pat. No. 6,369,893 is well-suited for such measurements. A schematic of such a system applicable to the present invention is illustrated in FIG. 1C. Christel et al. provide diode lasers (1050) through (1056) for illuminating a reaction mixture in reaction chamber (1070). Fluorescence excited by laser diodes (1050) through (1056) is collected by detectors (1060) through (1066), which typically are each operationally associated with a bandpass filter that restricts the wavelength of light that is detected. The excitation beams of laser diodes (1050) through (1056) may be the same or different. In one aspect, bandpass filters are selected to selectively pass fluorescence emitted by a plurality of spectrally resolvable fluorescent dyes so that each detector (1060) through (1066) collects fluorescence primarily from only one of the plurality of fluorescent dyes. For use with the present invention, one of the laser diode-detector pairs, for example (1052) and (1062), is allocated to detecting the fluorescent signal from an amplicon corresponding to a target polynucleotide, and one of the laser diode-detector pairs, for example (1056) and (1066), is allocated to detecting fluorescent signal from an amplicon corresponding to a reference sequence.

Control of all components of the detection system and fluidly closed reaction system (1086) are controlled by microprocessor (1080). Optical signals collected by detectors (1060) through (1066) are processed by conventional optics and converted into electrical signals, which, after conventional pre-amplification and conditioning (1082), are digitized for storage and/or further processing by microprocessor (1080). In one aspect of the invention, microprocessor (1080) is programmed to continuously monitor the value of the signal collected by one of the detectors, such as detector (1062). When the value reaches or exceeds a pre-programmed level, then microprocessor (1080) initiates a subroutine that provides controllers (1084) with a series of commands to actuate components of fluidly closed reaction system (1086) to initiate a subsequent amplification reaction. Microprocessor (1080) also changes and/or regulates the temperature of reaction chamber (1070) through controller (1088). In embodiments employing closed-loop control, microprocessor (1080) may calculate values of characteristics of curves, such as (1013) or (1015) of FIG. 1B, at predetermined intervals so that they may be compared to a predetermined level. When such calculated value reaches or exceeds a predetermined level, then microprocessor (1080) initiates the subroutine to start a subsequent amplification reaction, as described above.

As mentioned above, a computer preferably performs steps of the method of initiating a subsequent reaction, as described above. In one embodiment, a computer comprises a processing unit, memory, I/O device, and associated address/data bus structures for communicating information therebetween. The processing unit may be a conventional microprocessor driven by an appropriate operating system, including RISC and CISC processors, a dedicated microprocessor using embedded firmware, or a customized digital signal processing circuit (DSP), which is dedicated to the specific processing tasks of the method. The memory may be within the microprocessor, i.e. level 1 cache, fast S-RAM, i.e. level 2 cache, D-RAM, or disk, either optical or magnetic. The I/O device may be any device capable of transmitting information between the computer and the user, e.g. a keyboard, mouse, network card, or the like. The address/data bus may be a PCI bus, NU bus, ISA, or any other like bus structure. When the computer performs the method of the invention, the above-described method steps may be embodied in a program stored in or on a computer-readable product. Such computer-readable product may also include programs for graphical user interfaces and programs to change settings on electrophoresis systems or data collection devices. In one aspect, the invention provides algorithms and computer-readable products for controlling the operations described in FIG. 1C in a selected fluidly closed reaction system.

In one aspect of the invention, a computer-readable product comprises a program for execution by a computer to control the performance of a nested amplification reaction in a fluidly closed reaction system. In one embodiment, such a program may comprise instructions for the following: (a) reading values of an optical signal from a current amplification reaction, the optical signal being monotonically related to a concentration of an amplicon in the current amplification reaction, and the values of the optical signal having a most recent value; (b) determining a baseline signal level from the values of the optical signal; (c) computing a predetermined level from the values of the optical signal; (d) comparing the predetermined value with the most recent value of the optical signal; (e) initiating a subsequent amplification reaction whenever the most recent value of the optical signal is equal to or greater than the predetermined level; and (f) repeating steps (d) and (e) until the subsequent reaction is initiated. As used herein, "a most recent value" in reference to an optical signal means the value corresponding to the most recent measurement of an optical signal by a detection system that is monitoring the amplification reaction. In other words, it is the most recent value of an amplicon growth curve as it is generated in the course of an amplification reaction. In one embodiment, the step of initiating a subsequent amplification step further includes reading a sample portion table for a value of a sample portion to be used in the subsequent reaction, the sample portion table listing values of portion sizes to be used in each reaction of a sequence, generating commands to remove the current reaction mixture from the reaction chamber, generating commands to transfer a portion of the sample to a mixing chamber, generating commands to transfer amplification reagents of the subsequent reaction to the mixing chamber to form a reaction mixture, and generating commands to transfer the reaction mixture to the reaction chamber. The step of initiating may further include the steps of reading a reaction parameter table for values of reaction parameters to be used in the subsequent reaction, the reaction parameter table listing values of reaction parameters to be employed in each reaction of the sequence.

By way of example, a fluorescent indicator that can be used with the invention is an AMPLIFLUOR™ hairpin primer is used to generate a fluorescent signal whose intensity is monotonically related to the concentration of an amplicon, e.g. Whitcombe et al. *Nature Biotechnology,* 17: 804-808 (1999). Briefly, an AMPLIFLUOR™ hairpin primer has a target-binding portion, which is selected as with a conventional primer, and a hairpin portion at the 5' end of the target-binding portion, which maintains a fluorophore-quencher pair in close proximity whenever the hairpin is present, thereby quenching any fluorescent signal from the fluorophore. During the reverse extension step of the PCR, the duplex region of the hairpin is displaced as the reverse strand is extended through it to the end of the target polynucleotide, thereby moving the quencher away from the proximity of the fluorophore so that a fluorescent signal is generated. As the double stranded DNA product accumulates, the fluorescent signal from the reaction mixture increases. When the intensity of the fluorescent signal reaches or exceeds a predetermined level, e.g. 3 times baseline, a target-sensitive parameter is automatically changed to preclude further amplification of such amplicon.

Since in some applications, a sample may or may not contain a target polynucleotide. Thus, in one aspect, the amplicon of one or more reference sequences, or other internal standard, is monitored for determining whether or when to initiate a subsequent-stage reaction. That is, such an internal standard serves as a positive control and reaction parameter for initiating a subsequent-stage reaction. In another aspect, both amplicons of an internal standard and of a target polynucleotide must reach or exceed predetermined levels, which may be the same or different, in order to initiate a subsequent-stage reaction.

Systems for Implementing Methods of the Invention

Methods of the invention may be implemented by a variety of systems and apparatus that are based on different engineering approaches for sequestering reagents, moving reagents and reaction products into and out of reactions, controlling temperature, and detecting reaction products. Selection of a system depends on many factors including, but not limited to, availability of samples or specimens, form of samples or specimens, degree of hazard or infectivity posed by samples or specimens, desirability of portability, nature of the amplification reaction employed, how many samples need to be assayed, and the like. Exemplary systems that may be used to implement methods of the invention include fluidly closed reaction systems employing a rotary valve and a piston-type fluid pump under microprocessor control, such as disclosed in Christel et al. U.S. Pat. No. 6,369,893 and Dority, U.S. Pat. No. 6,374,684; closed disposable cuvettes having flexible reagent reservoirs for mechanically driving samples, reactants and products through reaction chambers and detection stations, as disclosed in Schnipelsky et al. U.S. Pat. No. 5,229,297; and Findlay et al. *Clin. Chem.,* 39:1927-1933 (1993); and microfluidics devices, such as disclosed in the references cited under Definitions, and further disclosed in Shoji et al. *Appl. Biochem. Biotechnol.*, 41:21-34 (1993) and *J. Micromech. Microeng.*, 4:157-171 (1994); McCormick et al. *Anal. Chem.*, 69:2626-2630 (1997); Cheng et al. *Topics Curr. Chem.*, 194:215-231 (1998); Stave et al. U.S. Pat. No. 6,663,833; Neri et al. U.S. Pat. No. 5,714,380; Northrup et al. U.S. Pat. No. 5,589,136; and the like. Such systems are capable of fluidly transferring reactants, samples, and reaction products between reservoirs and reaction chambers in a controlled manner. That is, such systems move reactants, samples, reaction products, and the like, in liquid solutions under liquid-moving force in a directed manner. Liquid-moving forces include differential pressure generated by various kinds of pumps or compressed gas reservoirs, electrokinetic pumps, and the like.

In one aspect, methods of the invention may be conveniently implemented by specific designs and methods of operation of rotary valves, reactant and waste reservoirs, and reaction chambers generally disclosed in Dority (cited above). In another aspect, in which real-time monitoring of amplification products is desired, such apparatus is conveniently used with the temperature controller and fluorometer disclosed by Christel et al (cited above). As will be described more fully below, the apparatus of Christel et al may further be used to provide closed-loop control of the initiation of a second-stage reaction in the fluidly closed reaction system of Dority.

FIGS. 2A-2K show diagrammatically the operation of an apparatus that follows the general design approach disclosed in Dority (cited above) for carrying out a sequence of two amplification reactions to amplify different target polynucleotides from two portions of the same sample under fluidly closed conditions. After a sample or specimen is loaded into the reaction system and pre-conditioned, e.g. by disrupting tissue, lysing cells, and the like, the resulting solution, referred to as the "sample," is fluidly transferred to a sample reservoir from which portions are dispensed to a reaction chamber under programmed control. Thus, the reaction system performs two cycles of sample/amplification reagent mixing, reaction mixture loading, amplifying and detecting, and reaction mixture removing, all under fluidly closed conditions. In a preferred embodiment, not shown, a rinsing step is included after each amplification step for removing traces of a prior reaction mixture, thereby reducing potential background and/or interfering reaction products. The rinsing step may be repeated.

Figure 2A:
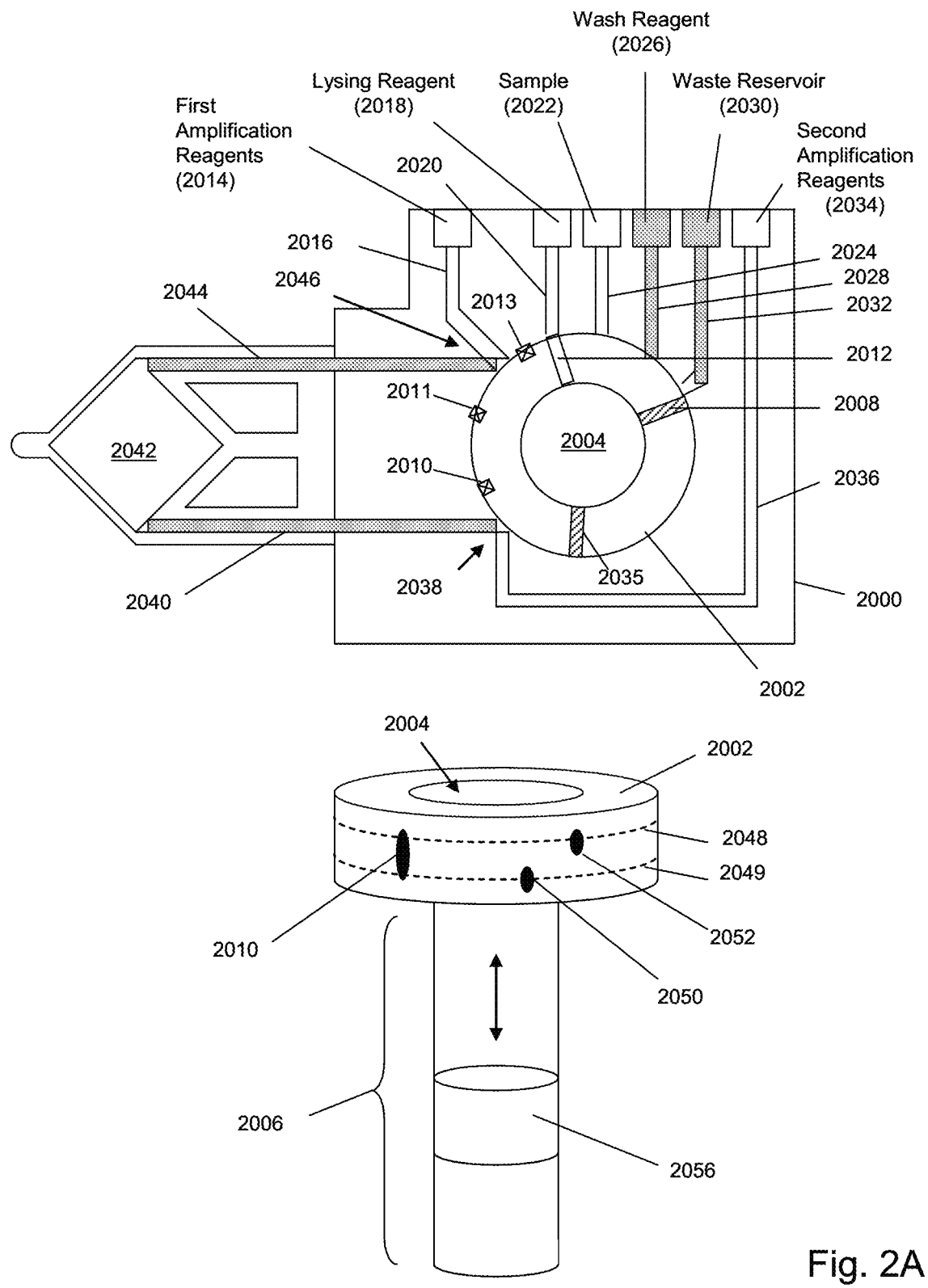
FIGS. 2A-2K diagrammatically illustrate implementation of sequential amplification reactions in a fluidly closed reaction system that employs a rotary valve and a piston-type fluid pump.

FIG. 2A shows housing (2000) that contains rotary valve (2002) having internal chamber (2004) that is operationally connected to piston-type pump (2006). Up-strokes of piston (2056) of pump (2006) pressurize chamber (2004) and force fluid contents out through whatever ports that may be in communication with reservoirs or the like; likewise, down strokes of piston (2056) of pump (2006) depressurize chamber (2004) and draw fluids in through whatever ports may be open and in communication with reservoirs or the like. Further descriptions of the operation and construction of such pump-rotary valve devices and the use of chamber (2004) for sample preparation is provided by Dority (cited above), which is incorporated by reference for this purpose. Rotary valve (2002) has various ports, for example (2050) and (2052), and associated passages, (2008) and (2012), that permit chamber (2004) to be in fluid communication with various reservoirs (described more fully below) or reaction chamber (2042) whenever such ports are aligned with corresponding ports to passages to such reservoirs or reaction chamber (2042). In the present exemplary embodiments, the longitudinal axes of such associated passages are radially disposed in rotary valve (2002) within either one of two planes perpendicular to the axis of rotary valve (2002) (shown with dashed lines (2048) and (2049)), such that chamber (2004) may be placed in fluid communication with ports of passages to reservoirs, and the like, disposed in housing (2000). Rotary valve (2002) further includes connecting passages (2010), (2011), and (2013), which permit a port in one plane of the valve to be placed in fluid communication with ports of housing (2000) that are in the other plane of rotary valve (2002). Such connection passages do not permit fluid communication with interior chamber (2004). As illustrated in FIG. 2A, when such connecting passages are aligned at (2046) with ports of passages (2044) and (2016), passages (2044) and (2016) are in fluid communication. Likewise, when such connecting passages are aligned at (2038) with ports of passages (2040) and (2036), passages (2040) and (2036) are in fluid communication. In FIGS. 2A-2I, cross-hatched passages and reservoirs in housing (2000) are in the pump-proximal plane of rotary valve (2002)(illustrated in the bottom panel of FIG. 2A by dotted line (2049)), whereas the non-hatched passages and reservoirs are in the pump-distal plane (illustrated in the bottom panel of FIG. 2A by dotted line (2048)). As mentioned above, rotary valve (2002) may place interior chamber (2004) in fluid communication with various reservoirs and reaction chamber (2042) that are connected by passages and have ports in the seat of housing (2000) that rotary valve (2002) rotates within. In the present example, such reservoirs include the following: (i) reservoir (2014) containing first amplification reagents, which may be fluidly connected to rotary valve (2002) by passage (2016); (ii) reservoir (2018) containing lysing reagents, for example, for disrupting surface membranes of cellular samples, which reservoir may be fluidly connected to rotary valve (2002) by passage (2020); (iii) sample reservoir (2022) containing sample or specimen material, which may be fluidly connected to rotary valve (2002) by passage (2024); (iv) reservoir (2026) containing wash solution, or wash reagent, which may be fluidly connected to rotary valve (2002) by passage (2028); (v) waste reservoir (2030), which may be fluidly connected to rotary valve (2002) by passage (2032); and (vi) reservoir (2034) containing second amplification reagents, which may be fluidly connected to rotary valve (2002) by passage (2036).

Figure 2B:
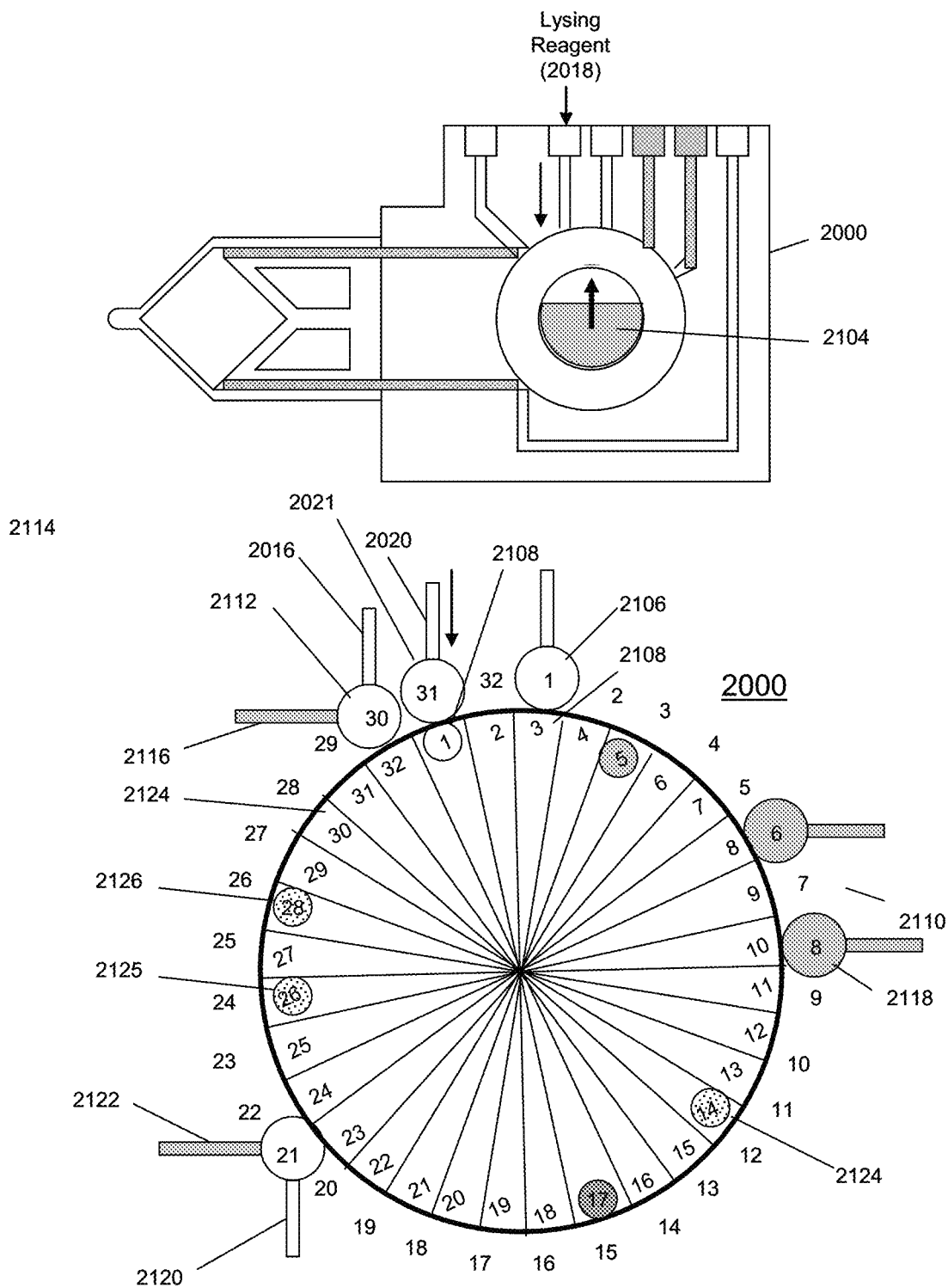

FIGS. 2B to 2I illustrate the operation of the apparatus of FIG. 2A for carrying out a sequence of two amplification reactions under fluidly closed conditions. For the purpose of teaching how particular embodiments of rotary valve (2002) operate, rotary valve (2002) is shown diagrammatically in each of FIGS. 2B to 2I divided into 32 sectors, which are numbered. Adjacent to each numbered sector of rotary valve (2002) there is a corresponding location in the seat of housing (2000) that is also numbered. The number 32 is merely a design choice that reflects, among other things, the capacity of rotary valve (2002) to provide interconnections in a complex system of reservoirs and chambers. At a starting position of rotary valve (2002), the numbers adjacent to each other at each sector for the two sets is the same, as shown in FIG. 2B. Certain of the numbers ("inner numbers") on rotary valve (2002) are circled (1, 5, 14, 17, 26, 28), and certain of the numbers ("outer numbers") adjacent and exterior to rotary valve (2002) are circled (1, 6, 8, 21, 30, 31). The circles indicate the sectors at which the ports to the various reservoirs and chambers are located. Circles with shaded interiors, e.g. 5, 6, 8, and 17 indicate ports located in the "pump-proximal" plane (2049) of rotary valve (2002) and un-shaded circles, e.g. 1, 21, 30, 31, indicate ports located in the "pump-distal" plane (2048) of rotary valve (2002). Circles (2124), (2125), and (2126) at sectors 14, 26, and 28, respectively, that have stippled interiors indicate connecting passages.

A sample or specimen, e.g. collected using an ordinary filter paper wipe, is loaded in interior chamber by an operator, after which the reaction system is fluidly closed. In FIG. 2B, rotary valve (2002) is shown at a starting position in which port 1 (2108) of the valve is aligned with port 31 (2021) of housing (2000) so that lysing reagent reservoir (2018) is in fluid communication with interior chamber (2004) where sample preparation procedures are carried out. With a down-stroke of pump (2056), lysing reagent is drawn through the path defined by passage (2020), ports (2021) and (2108), and passage (2012) to fill (2104) interior chamber (2004) where it interacts with the sample. Wash steps may be performed as shown in FIGS. 2J and 2K and described below, either before or after lysing, depending on the nature of the specimen being analyzed.

Figure 2C:
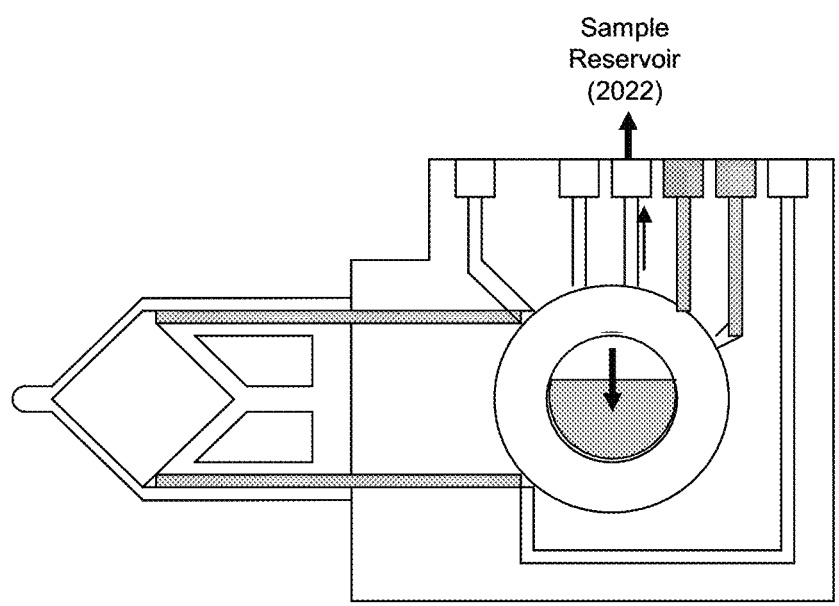
Figure 2C:
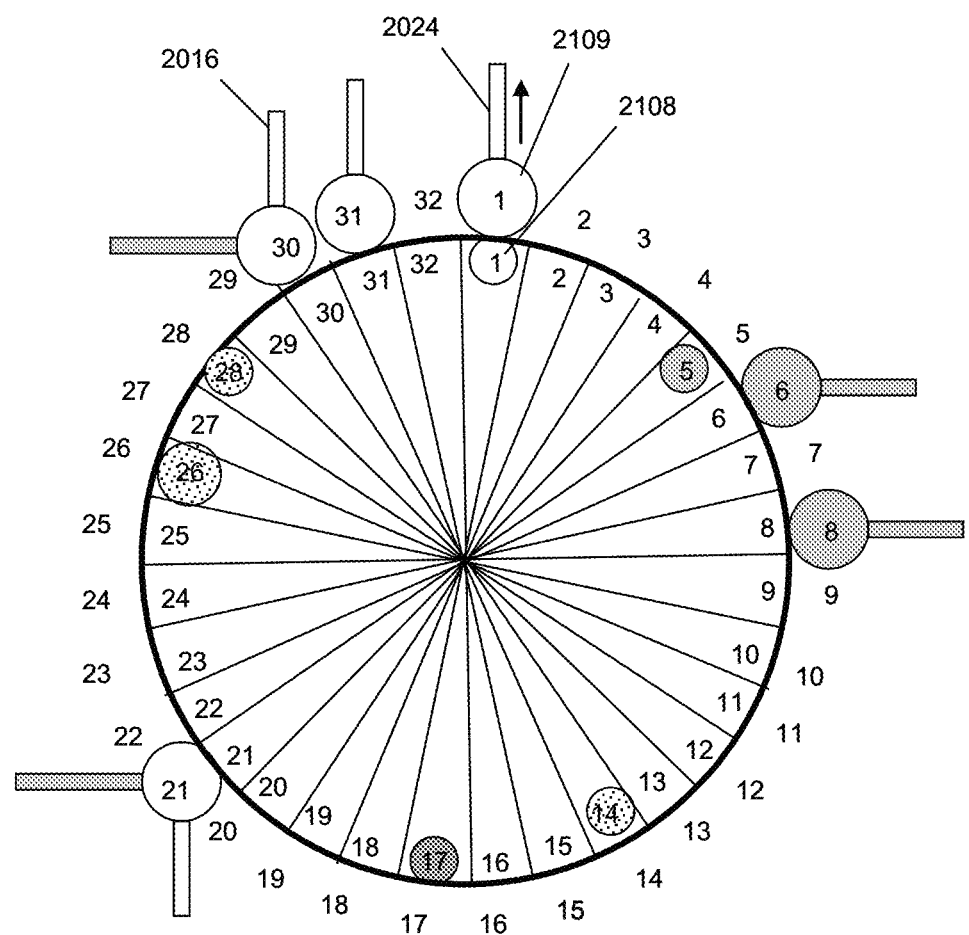
Figure 2D:
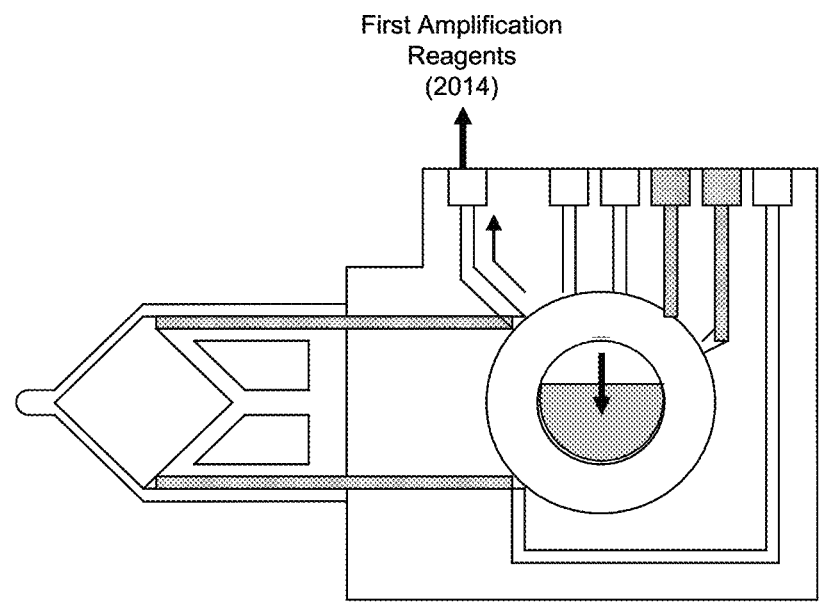
Figure 2D:
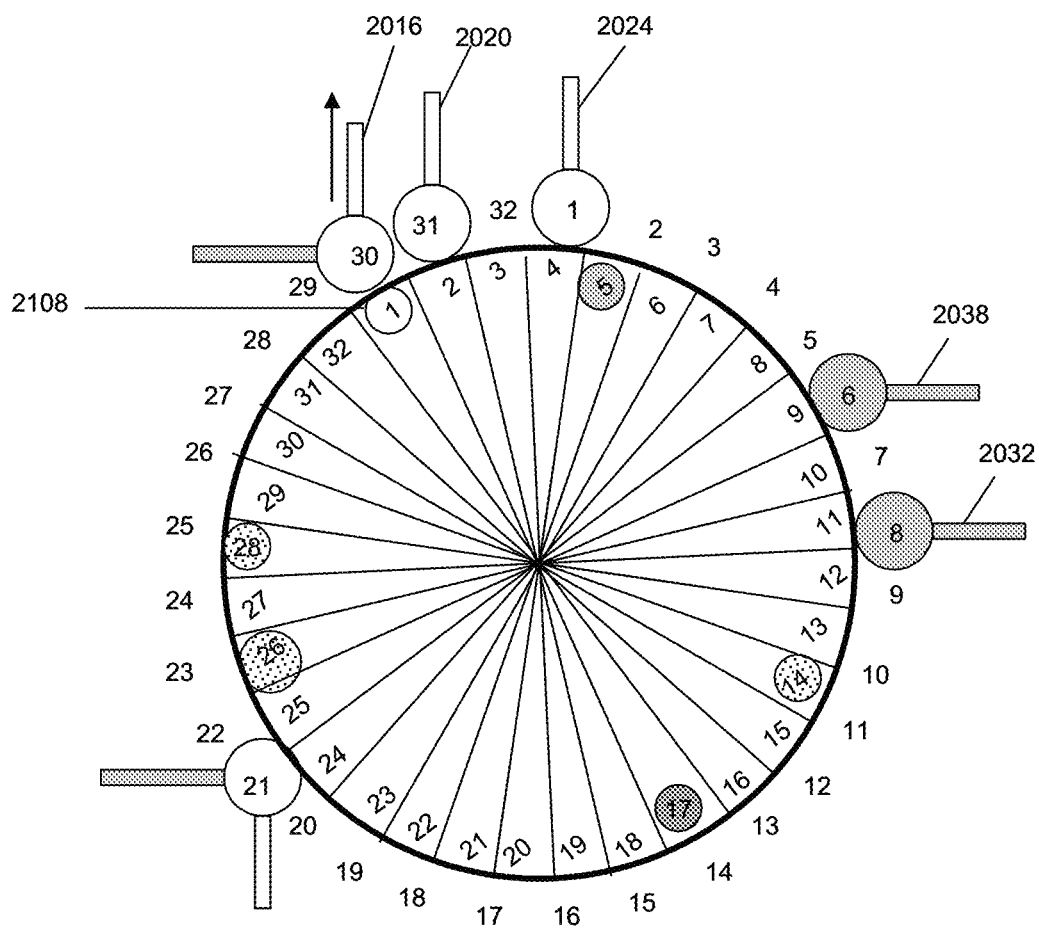
Figure 2E:
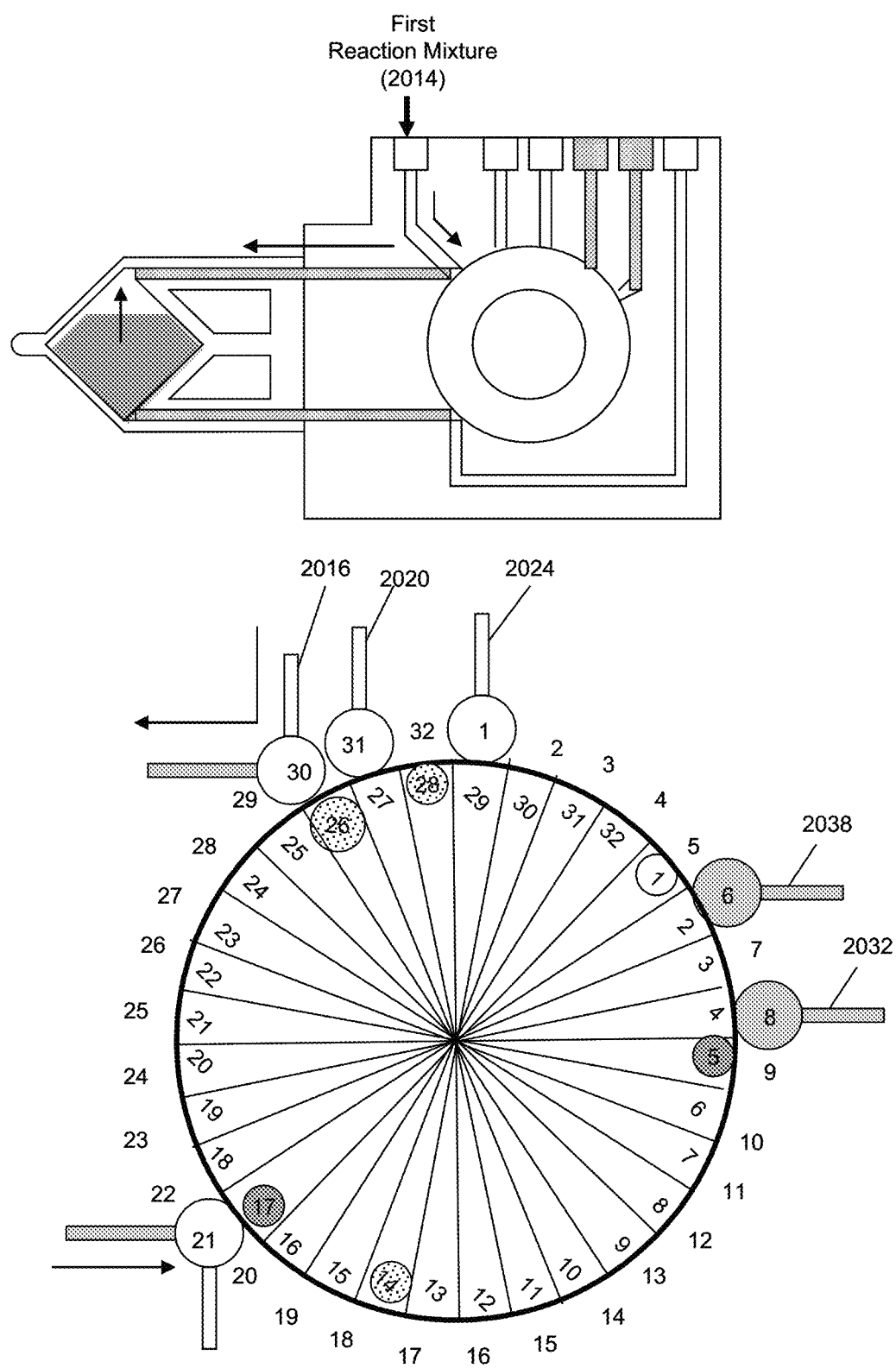
Figure 2F:
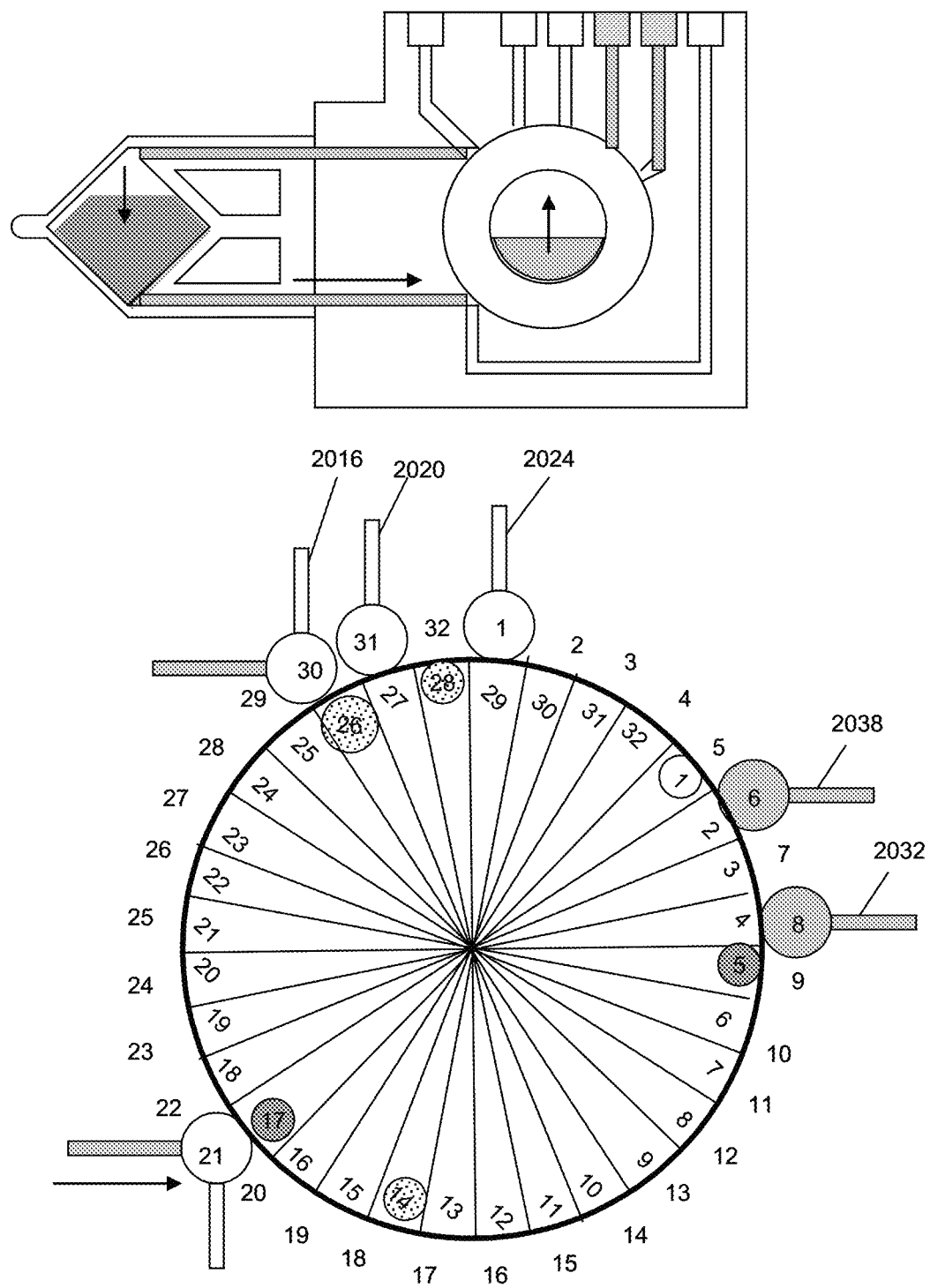
Figure 2G:
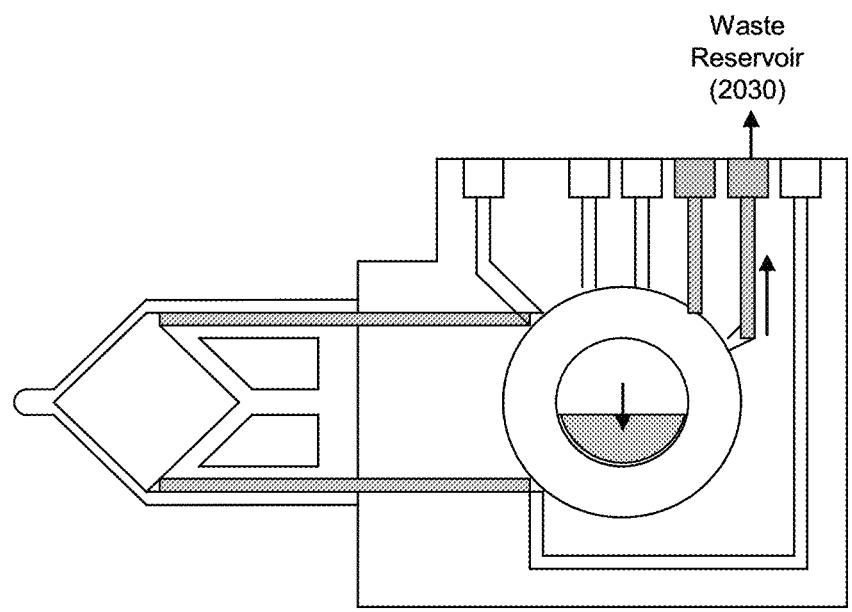
Figure 2G:
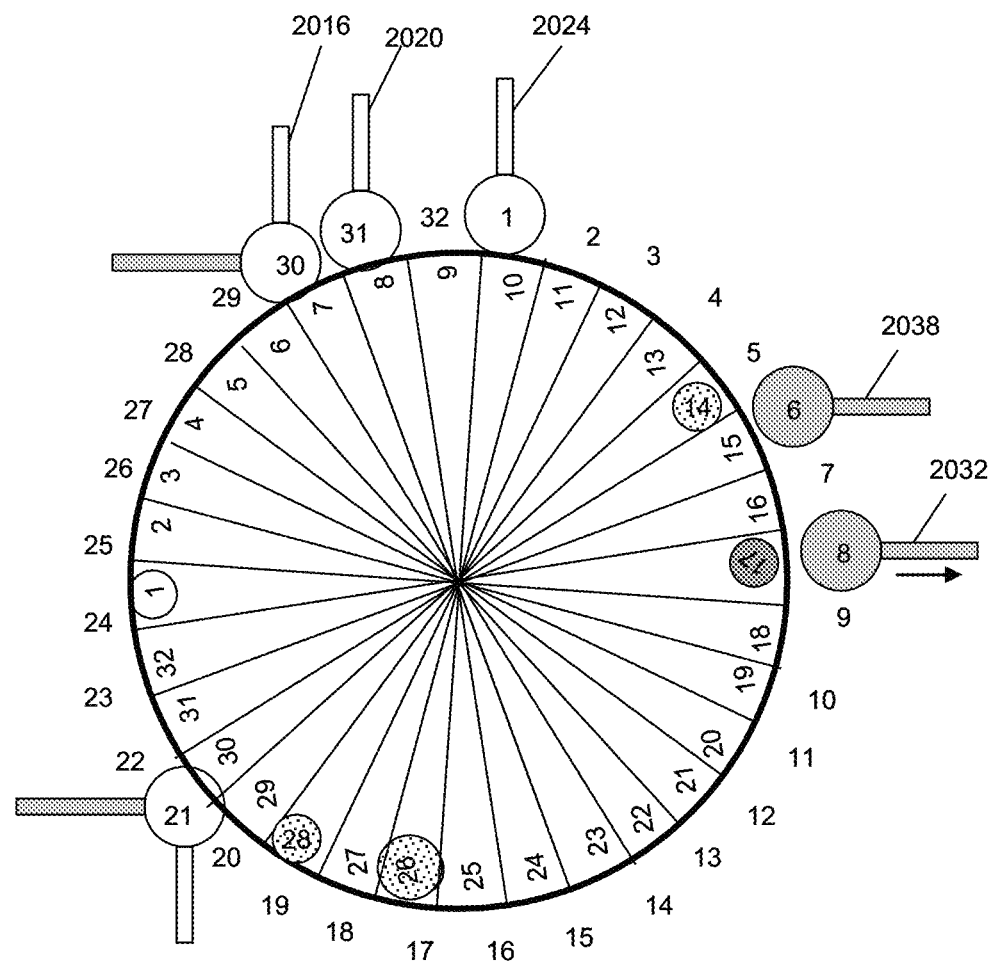
Figure 2H:
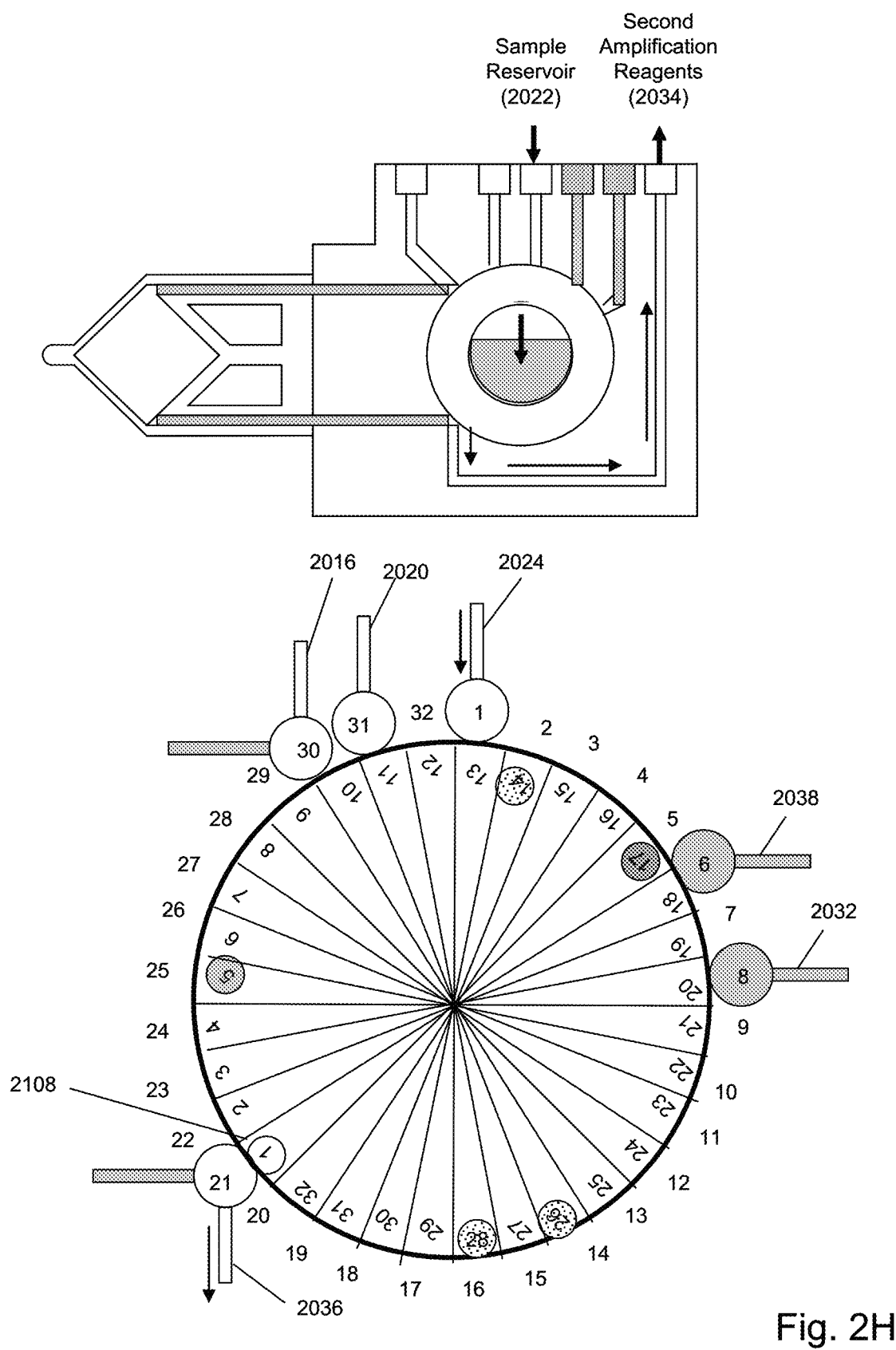
Figure 2I:
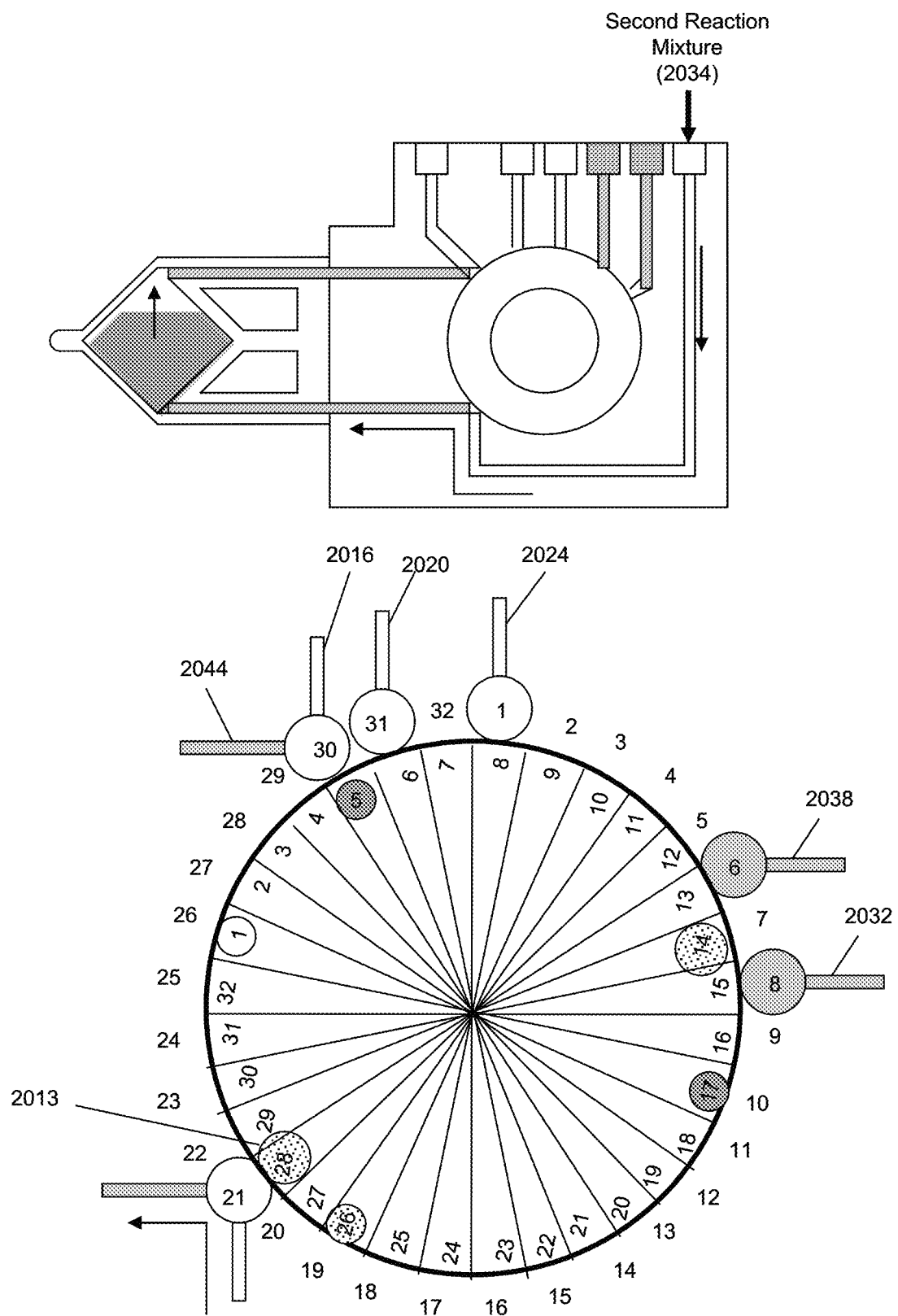

Going to FIG. 2C, after the sample is incubated in the lysing reagent, rotary valve (2002) is rotated to align port 1 (2108) of the valve with port 1 (2109) of housing (2000), thereby putting interior chamber (2004) in fluid communication with sample reservoir (2022). An up-stroke of piston (2056) drives the mixture of lysing reagent and sample, referred to as the "lysate" or simply the "sample," from interior chamber (2004) into sample reservoir (2022). A portion of the sample is then drawn out of sample reservoir (2022) and transferred into interior chamber (2004) by a partial down stroke of piston (2056), after which rotary valve (2002) is rotated to align port 1 (2108) with the port of passage (2016) (at sector 30) of housing (2000), thereby placing first amplification reagents reservoir (2014) in fluid communication with interior chamber (2004), as shown in FIG. 2D. An up-stroke of piston (2056) drives the sample from interior chamber (2004) to first amplification reagent reservoir (2014) where the first amplification reagents mix with the sample to form a first reaction mixture. As shown in FIG. 2E, rotary valve (2002) is rotated to align the connecting passage (2011) at sector 26 with ports of passage (2016) and passage (2044) so that there is fluid communication between first amplification reagent reservoir (2014) and reaction chamber (2042). Simultaneously, rotary valve passage (2035) is aligned with the port of passage (2040) (represented as a shaded circle at sector 17 of rotary valve (2002)) to provide fluid communication between reaction chamber (2042) and interior chamber (2004). Upon a down stroke of piston (2056), the first reaction mixture is drawn from first amplification reagent reservoir (2014), through passages (2016) and (2044) and into reaction chamber (2042), where a first amplification reaction takes place. Optionally, rotary valve (2002) can be rotated to close off passages (2044) and (2040) during the amplification reaction. After the first amplification reaction is completed, the first reaction mixture is removed from reaction chamber (2042) by a down stroke of piston (2056), which draws the mixture into interior chamber (2004), as illustrated in the top panel of FIG. 2F, after which rotary valve (2002) is rotated to align passage (2035) with the port of passage (2032) so that waste reservoir (2030) is in fluid communication with interior chamber (2004). Upon an up-stroke of piston (2056), the spent first reaction mixture is transferred from interior chamber (2004) through passage (2032) to waste reservoir (2030), as shown in FIG. 2G. Rotary valve (2002) is then rotated to align passage (2012) with passage (2024) (not shown in the figure) so that sample reservoir (2022) is in fluid communication with interior chamber (2004), after which a down stroke of piston (2056) draws a portion of the sample into interior chamber (2004). Rotary valve (2002) is rotated to align passage (2012) (shown as port 1 in FIG. 2H) with passage (2036) so that second amplification reagent reservoir (2034) is brought into fluid communication with interior chamber (2004). An up-stroke of piston (2056) drives the portion of sample into second amplification reagent reservoir (2034) where it mixes with second amplification reagents to form a second reaction mixture. Rotary valve (2002) rotates to align passage (2008) (port 5 in shaded circle in FIG. 2I) with passage (2044) and passage (2013)(shown as stippled circle in sector 28 of rotary valve (2002)) so that second amplification reagent reservoir (2034) is in fluid communication with reaction chamber (2042) which, in turn, is in fluid communication with interior chamber (2004). Upon down stroke of piston (2056) second reaction mixture is drawn from second amplification reagent reservoir (2034) through passage (2036), through passage (2040), and into reaction chamber (2042), where a second amplification reaction takes place.

Figure 2J:
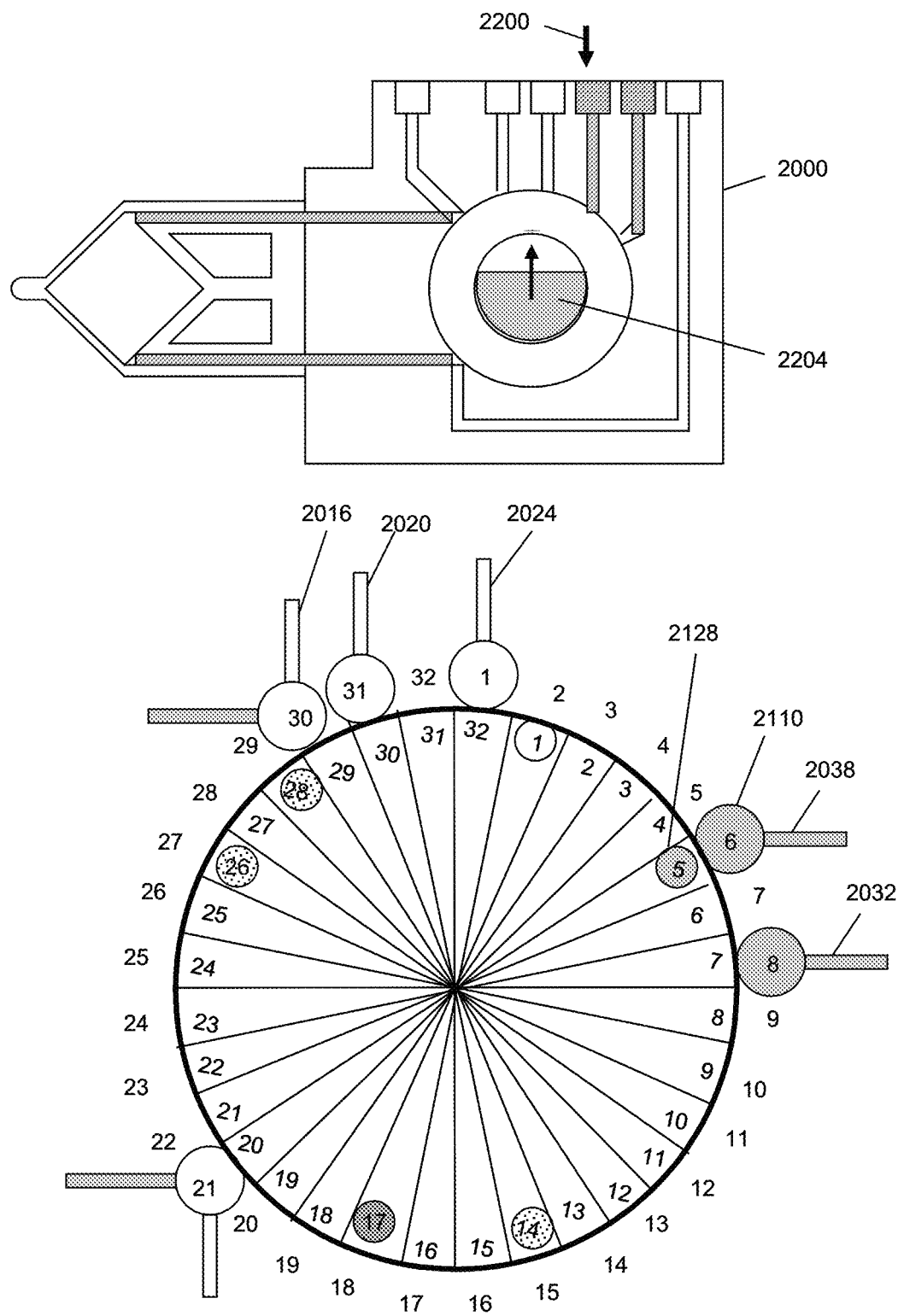
Figure 2K:
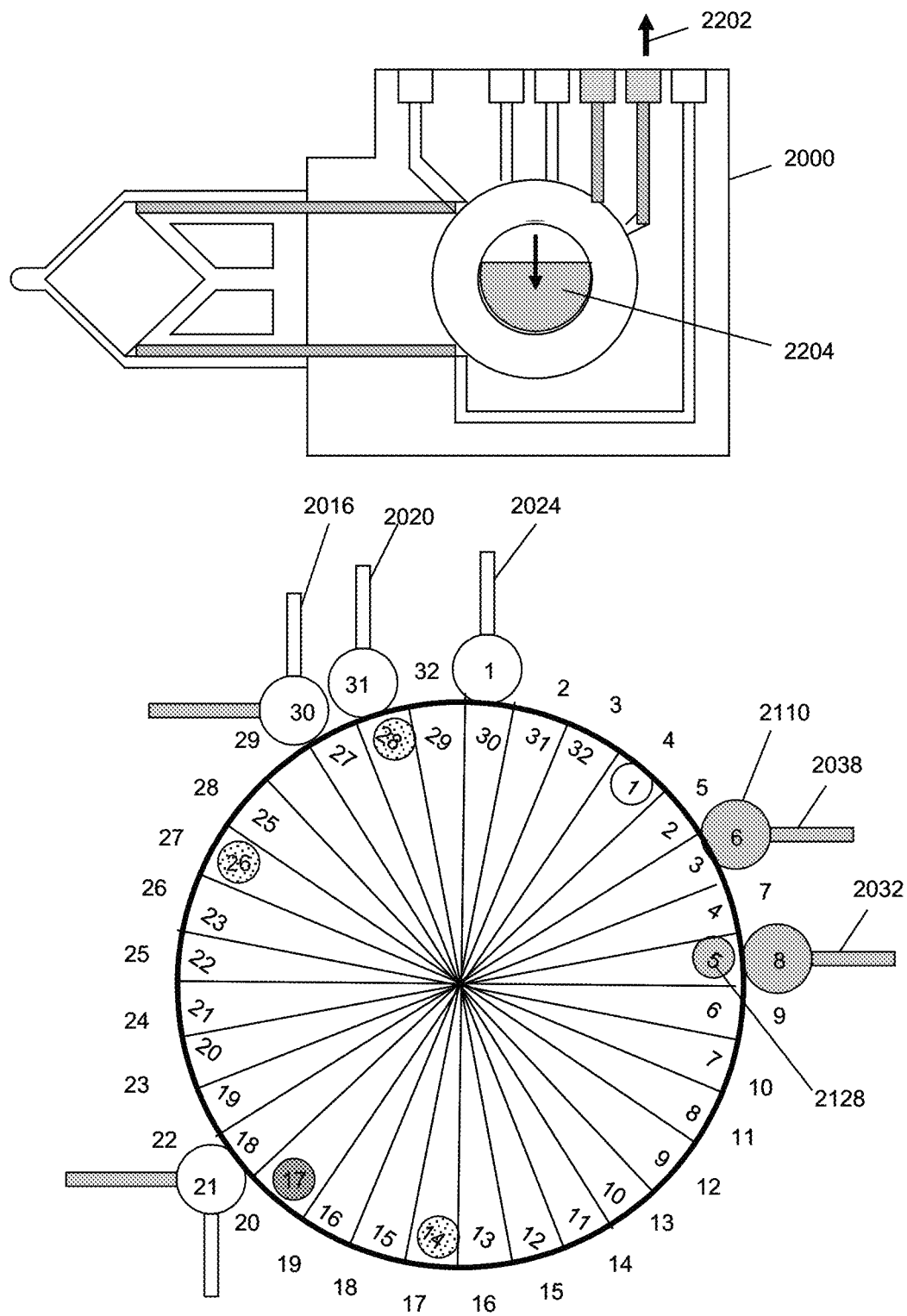

As mentioned above, after incubation in the lysing reagent, the sample may optionally be washed as shown in FIGS. 2J and 2K. Briefly, in FIG. 2J, rotary valve (2002) is rotated so that port (2128) in sector 5 aligns with port 6 (2110) of housing (2000) so that with an down-stroke of piston (2056) wash solution in reservoir (2026) is drawn (2200) (and (2204)) into interior chamber (2004). As shown in FIG. 2K, by rotating rotary valve (2002) so that port 5 (2128) aligns with port 8 of housing (2000) permitting fluid communication between interior chamber (2004) and waste reservoir (2030), wash solution in interior chamber (2004) may be expelled (2202) into waste reservoir (2030) upon an up-stroke of piston (2056). This process may be repeated as needed.

It should be clear from the above example that design of rotary valve (2002), e.g. selection of the number and kind of passages, and the selection of the number and type of reagent reservoirs in housing (2000) is a matter of routine design choice of one of ordinary skill in the art.

Internal Standards

Often times it is desirable to compare readouts from different assays, for example, when attempting to determine whether measured expression levels of a target gene in a patient specimen are within normal ranges. In medical applications in particular, it is often desired to compare assay results from a patient sample to those of reference samples. Such comparisons are readily made by determining ratios of a signal associated with the target polynucleotide to a signal associated with a reference sequence, or internal standard, from the same sample. This permits values for a target polynucleotide to be compared to those from other samples or specimens. Use and selection of internal standards, and in particular, reference sequences, are well-known to those of ordinary skill in the art, as reflected in the following references that are incorporated by reference: Radonic et al. *Biochem. Biophys. Res. Comm.* 313:856-862 (2004); Bustin, *J. Mol. Endoccrinol.*, 29:23-39 (2002); Hoorfar et al. *J. Clin. Microbiol.*, 42:1863-1868 (2004); and the like. It is understood that the signal or a value associated with a reference sequence may also be a function, for example, an average, of signals or values measured from multiple reference sequences.

The type of internal standard or reference sequence selected depend on the nature of the samples being analyzed. For samples comprising mammalian cells or tissues exemplary references sequences are listed in Table I.

TABLE I

Exemplary Reference Sequences

| Reference Gene | Gene Product Name | NCBI Accession No. |
|---|---|---|
| GAPDH | glyceraldehydes 3-phosphate dehydrogenase | J02642 |
| G6PDH | glucose 6-phosphate dehydrogenase | X03674 |
| HPRT | hypoxanthine-guanine phosphoribosyltransferase | L29382 |
| PBGD | porphobilinogen deaminase | X04808 |
| Alb | | L00132 |
| Act | β-actin | M10277 |
| Tub | α-tubulin | X01703 |
| TBP | TATA-box binding protein | M55654 |
| L13 | ribosomal protein L13 | X56923 |
| β2M | β2-microglobulin | J00115 |
| PPIA | peptidyl prolyl isomerase A | Y00052 |
| PLA | phospholipase A2 18S and 28S ribosomal RNA | M86400 |

In some applications where the presence or absence of a target polynucleotide in a sample is to be determined, an internal sample that is known to be present can be amplified as a positive control along with the target polynucleotide, so that if the target polynucleotide is absent a positive signal is still generated. In such applications, an internal standard can be an endogenous polynucleotide or it can be an exogenous polynucleotide added to the reaction mixture for such purpose.

Sample or Specimen Preparation

Samples or specimens containing target polynucleotides may come from a wide variety of sources for use with the present invention, including cell cultures, animal or plant tissues, patient biopsies, environmental samples, or the like. Samples are prepared for assays of the invention using conventional techniques, which typically depend on the source from which a sample or specimen is taken.

Samples or specimens are collected so as to minimize the chance of contamination of the sample or specimen by external elements, or the environment by the sample or specimen if it contains hazardous components. Generally, this is carried out by introducing a sample for analysis, e.g. tissue, blood, saliva, etc., directly into a sample collection chamber within a fluidly closed system. Typically, the prevention of cross-contamination of the sample may be accomplished by directly injecting the sample into the sample collection chamber through a sealable opening, e.g. an injection valve, or a septum. Generally, sealable valves are preferred to reduce any potential threat of leakage during or after sample injection. In addition to the foregoing, the sample collection portion of the device may also include reagents and/or treatments for neutralization of infectious agents, stabilization of the specimen or sample, pH adjustments, and the like. Stabilization and pH adjustment treatments may include, e.g. introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Prior to carrying out amplification reactions on a sample, it will often be desirable to perform one or more sample preparation operations upon the sample. Typically, these sample preparation operations will include such manipulations as extraction of intracellular material, e.g. nucleic acids from whole cell samples, viruses and the like. One or more of these various operations may be readily incorporated into the fluidly closed systems contemplated by the present invention.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g. denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Physical methods may be used to extract the nucleic acids and denature DNA binding proteins. Wilding et al. U.S. Pat. No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g. employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to perform cell lysis/extraction, including, e.g. subjecting cells to ultrasonic agitation, or forcing cells through small apertures, thereby subjecting the cells to high shear stress resulting in rupture.

Following extraction, it will often be desirable to separate the nucleic acids from other elements of the crude extract, e.g. denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g. by binding the nucleic acids to a solid phase and washing away the contaminating salts or performing gel filtration chromatography on the sample, passing salts through dialysis membranes, and the like. Suitable solid supports for nucleic acid binding include, e.g. diatomaceous earth, silica (i.e., glass wool), or the like. Suitable gel exclusion media, also well known in the art, may also be readily incorporated into the devices of the present invention, and is commercially available from, e.g. Pharmacia and Sigma Chemical Co.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g. charged groups, affinity binding groups and the like, i.e. poly-T oligonucleotides for mRNA purification. Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g. platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g. acting as a salt junction). Such barriers may include, e.g. dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use. In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. As such, a system of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself.

In some applications, such as measuring target polynucleotides in rare metastatic cells from a patient's blood, an enrichment step may be carried out prior to conducting an assay, such as by immunomagnetic isolation. Such isolation or enrichment may be carried out using a variety of techniques and materials known in the art, as disclosed in the following representative references that are incorporated by reference: Terstappen et al. U.S. Pat. No. 6,365,362; Terstappen et al. U.S. Pat. No. 5,646,001; Rohr et al. U.S. Pat. No. 5,998,224; Kausch et al. U.S. Pat. No. 5,665,582; Kresse et al. U.S. Pat. No. 6,048,515; Kausch et al. U.S. Pat. No. 5,508,164; Miltenyi et al. U.S. Pat. No. 5,691,208; Molday, U.S. Pat. No. 4,452,773; Kronick, U.S. Pat. No. 4,375,407; Radbruch et al. chapter 23, in *Methods in Cell Biology*, Vol, 42 (Academic Press, New York, 1994); Uhlen et al. *Advances in Biomagnetic Separation* (Eaton Publishing, Natick, 1994); Safarik et al. *J. Chromatography B*, 722:33-53 (1999); Miltenyi et al. *Cytometry*, 11:231-238 (1990); Nakamura et al. *Biotechnol. Prog.*, 17:1145-1155 (2001); Moreno et al. *Urology*, 58:386-392 (2001); Racila et al. *Proc. Natl. Acad. Sci.*, 95:4589-4594 (1998); Zigeuner et al. *J. Urology*, 169:701-705 (2003); Ghossein et al. *Seminars in Surgical Oncology*, 20:304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g. physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

EXAMPLES

Example 1

Successive Amplification Reactions in the Same Reaction Chamber for Detection of Methicillin-Resistant *Staphylococcus aureus* (MRSA)

In this example, two tests using a standard PCR assay for MRSA (e.g. see, Warren et al. *J. Clinical Microbiology*, 42:5578-5581 (2004), which is incorporated herein by reference) were carried out. Both tests were performed in a Cepheid GENEXPERT™ amplification system (disclosed in various U.S. patents, including U.S. Pat. Nos. 6,713,297; 6,403,037; 6,374,684; 6,369,893, which are incorporated herein by reference). In the first test, a series of two PCR cycles were carried out in the same reaction chamber with a rinsing step in between. In the first cycle, all the reagents were present for a PCR that generated a predictable signal and in the second cycle only buffer was loaded into the reaction chamber. In the second test, the same procedure was carried out as in the first test, except that in the second cycle all the reagents were present, as in the first cycle. In both tests, the system was programmed to carry out the following steps: (i) filling the reaction chamber with a first reaction mixture, (ii) performing a first PCR in the reaction chamber, (iii) emptying the reaction chamber of the reaction mixture, (iv) rinsing the reaction chamber with a wash solution [implemented by steps (iva) filling the reaction chamber with TET buffer and (ivb) emptying the reaction chamber of TET buffer], (v) purging the reaction chamber with air and heating the reaction chamber; (vi) filling the reaction chamber with a second reaction mixture [which in the first test was simply TET buffer]; and (vii) performing a second PCR in the reaction chamber. The reaction mixtures (first in the first test, and first and second in the second test) had identical compositions.

Figure 3B:
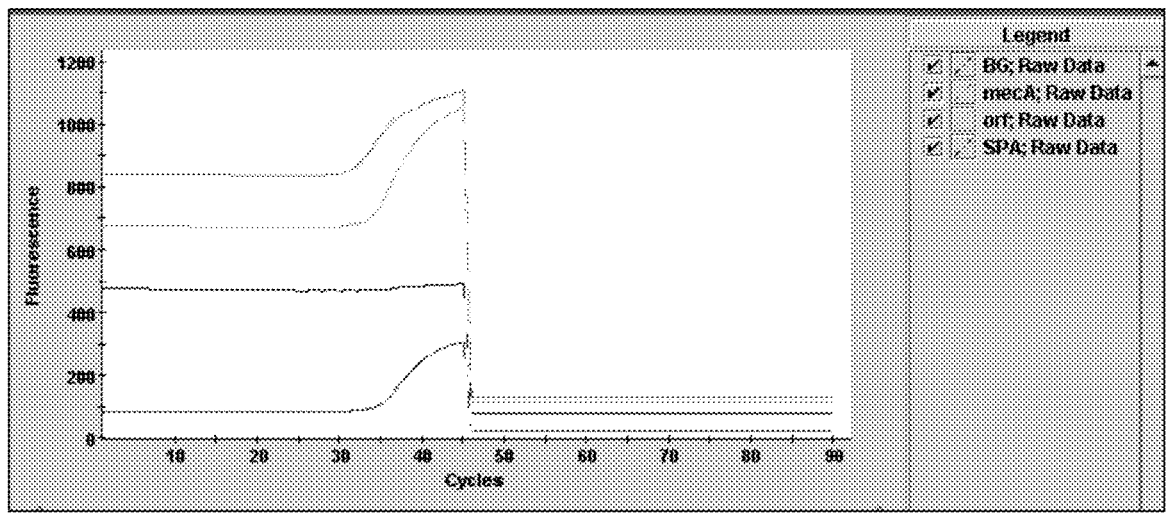
Figure 3C:
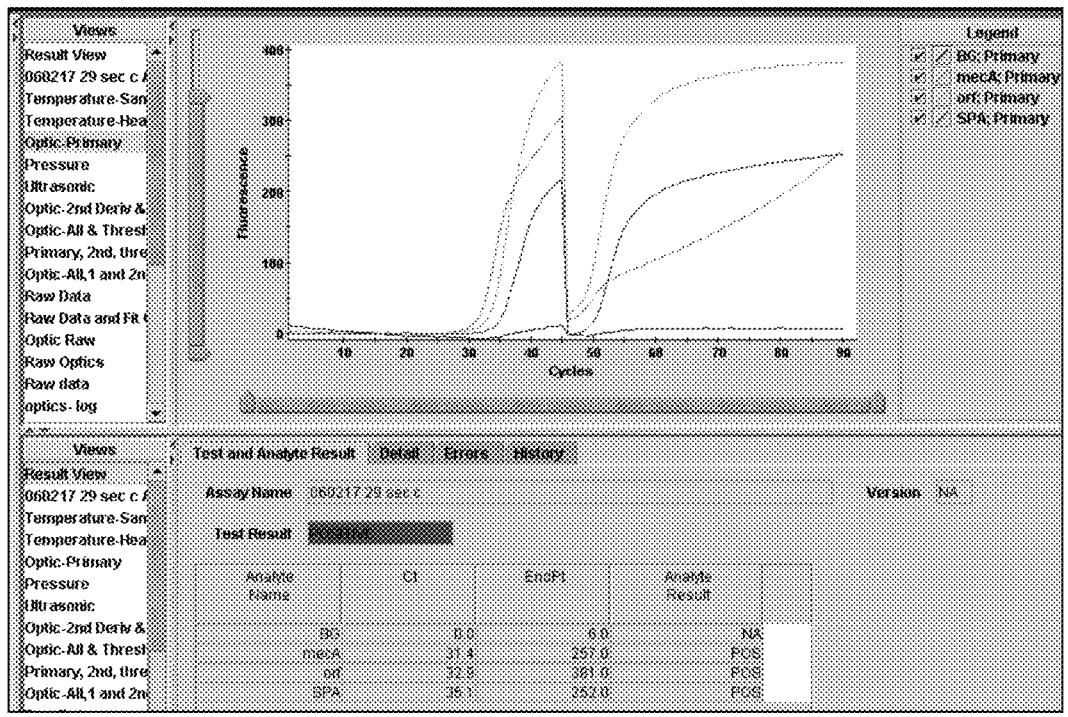

GENEXPERT™ amplification system cartridges were prepared as follows: (1) a sample was made by mixing 0.8 µL of MRSA DNA (ATCC) at 1000 copies/µL with 199.2 µL TET buffer for a final concentration of 4 copies/4, or 100 copies per reaction (TET buffer is a conventional Tris-based buffer containing a divalent chelator and mild detergent, e.g. Tris-HCl, EDTA, and Tween-20), (2) for test 2, chambers 9 and 11 of a GENEXPERT™ amplification system cartridge were each loaded with both a TSR reagent bead and an EZR reagent bead; for test 1, only one chamber was loaded with TSR and EZR beads, the other chamber was loaded with TET buffer (TSR is a lyophilized aliquot of MRSA target-specific reagents and EZR is a lyophilized aliquot of PCR enzymes, described in U.S. Patent Publication Nos. 2006/0068398 and 2006/0068399, which are incorporated herein by reference), (3) 200 µL of sample was place into chamber 10 of the GENEXPERT™ amplification system cartridge, (4) 500 µL of TET buffer (used as a wash solution) was placed into chamber 5 of the GENEXPERT™ amplification system cartridge. A detailed listing of GENEXPERT™ amplification system programming instructions for tests 1 and 2 is shown in FIG. 3A. The step 26 temperature protocol (first PCR) was hold for 30 s at 95° C. followed by 45 cycles of is at 92° C., 6 s at 62° C., and 6 s at 68° C. The step 43 temperature protocol (purging step) was hold for is at 95° C. and hold for 30 s at 45° C. The step 65 temperature protocol (second PCR) was the same as that for step 26. Results for test 1 are shown in FIG. 3B, where curve 1 (BG) is a control amplicon (from *bacillus globigii*), curve 2 is a mecA gene amplicon from MRSA, curve 3 is a orfH gene amplicon from MRSA, and curve 4 is an SPA amplicon from MRSA. The data indicate that no further reaction occurs in the second PCR when the reaction chamber is rinsed and loaded with buffer. Results for test 2 are shown in FIG. 3C (curve numbers being the same as those for FIG. 3B). The data show similar amplification of MRSA targets in both the first and second PCRs.

Example 2

Detection of MRSA by Two Amplification Reactions Conducted Successively in the Same Reaction Chamber: Non-Lyophilized Reagents In this example, two tests were carried out in which two PCRs amplifying different target sequences were run in series in the same reaction chamber. The only parameter changed in the two tests was the order in which the reactions were run. Two replicates of each test were run. As in Example 1, here MRSA target sequences were used. For this example, two reaction mixtures were prepared: a first reaction mixture (MM1) containing the MRSA genes, mecA (labeled with an Alexa 647 probe (A647)) and SPA (labeled with a tetramethylrhodamine probe (TxR)) and the internal control BG (labeled with an Alexa 532 probe (A532)); and second reaction mixture (MM2) containing the MRSA gene, orfH, (labeled with a fluorescein probe (FAM)) and the internal control BG (in this case labeled with a tetramethylrhodamine probe (TxR)). Further details of the first and second reaction mixtures is given in Tables 2 and 3, respectively.

TABLE 2

Number of Reactions = 15

| Component | Stock Conc. | Final Conc. | Amt for 1 Rxn (25 µL) | Amt for X Rxns | Vendor | Cat# | Lot# |
|---|---|---|---|---|---|---|---|
| TET | n/a | n/a | 2.70 | 40.50 | Anu Mokkapati | n/a | Feb. 6, 2006 |
| 5X Lyo Buffer | 5X | 1X | 5.0 | 75.00 | Dave Swenson | nb 330 p. 124 | 051209DDS |
| MgCl2 | 1M | 4 mM | 0.10 | 1.50 | Ambion | 9530G | 023R34A |
| KCl | 2M | 20 mM | 0.25 | 3.75 | Ambion | 9640G | 064R37A |
| dNTP | 25 mM | 400 µM | 0.4 | 6.00 | Inventory | 001-0135 | B2001A |
| bigC-spa Forward Primer - M216 | 25 µM | 225 nM | 0.225 | 3.38 | Bothell | n/a | see log sheet |
| bigC-spa Reverse Primer - M271 | 25 µM | 225 nM | 0.225 | 3.38 | Bothell | n/a | see log sheet |
| SPA probe - TxR - M316 | 25 µM | 200 nM | 0.2 | 3.00 | Bothell | n/a | see log sheet |
| F-MecA406-53 - M398 | 25 µM | 500 nM | 0.5 | 7.50 | Bothell | n/a | see log sheet |
| R-MecA522-53 - M399 | 25 µM | 500 nM | 0.5 | 7.50 | Bothell | n/a | see log sheet |
| P-MecA2-465Alx - Alx647 - M350 | 25 µM | 200 nM | 0.2 | 3.00 | Trilink | n/a | see log sheet |
| BG096U - M274 | 25 µM | 400 nM | 0.4 | 6.00 | Bothel | n/a | see log sheet |
| BG-R - M275 | 25 µM | 400 nM | 0.4 | 6.00 | Bothel | n/a | see log sheet |
| BGCEPH1 - A532 - M254 | 25 µM | 200 nM | 0.2 | 3.00 | Bothel | n/a | see log sheet |
| Taq + 7.5 uM HM | 5 units/µL | 6 units | 1.2 | 18.00 | Eppendorf | HM | 060210CL |
| | | | 12.50 | 187.50 | | | |

TABLE 3

| | | | Amt for 1 Rxn | Amt for | |
| Component | Stock Conc. | Final Conc. | (25 µL) | X Rxns | Vendor |
| --- | --- | --- | --- | --- | --- |
| \multicolumn{6}{c}{Number of Reactions = 15} | | | | | |
| TET | n/a | n/a | 2.55 | 38.25 | Anu Mokkapati |
| 5X Lyo Buffer | 5X | 1X | 5.0 | 75.00 | Dave Swenson |
| MgCl2 | 1M | 4 mM | 0.10 | 1.50 | Ambion |
| KCl | 2M | 20 mM | 0.25 | 3.75 | Ambion |
| dNTP | 25 mM | 400 µM | 0.4 | 6.00 | Inventory |
| Type-I-Primer-a M358 | 25 µM | 400 nM | 0.4 | 6.00 | Bothel |
| Type-II&IV-Primer-b M359 | 25 µM | 400 nM | 0.4 | 6.00 | Bothel |
| Type-III-Primer-a M362 - 100 µM | 25 µM | 400 nM | 0.4 | 6.00 | Bothel |
| orfX-For-C-GCA29 M363 | 25 µM | 600 nM | 0.6 | 9.00 | Bothel |
| orfX-Probe-ATC30 -FAM - M361 | 25 µM | 200 nM | 0.2 | 3.00 | Bothel |
| BGf2 - M159 | 25 µM | 400 nM | 0.4 | 6.00 | MWG |
| BGr2 - M160 | 25 µM | 400 nM | 0.4 | 6.00 | MWG |
| Bg-Probe1 - TxR - M314 | 25 µM | 200 nM | 0.2 | 3.00 | Bothel |
| Taq + 7.5 uM HM | 5 units/µL | 6 units | 1.2 | 18.00 | Eppendorf |

Figure 4B:
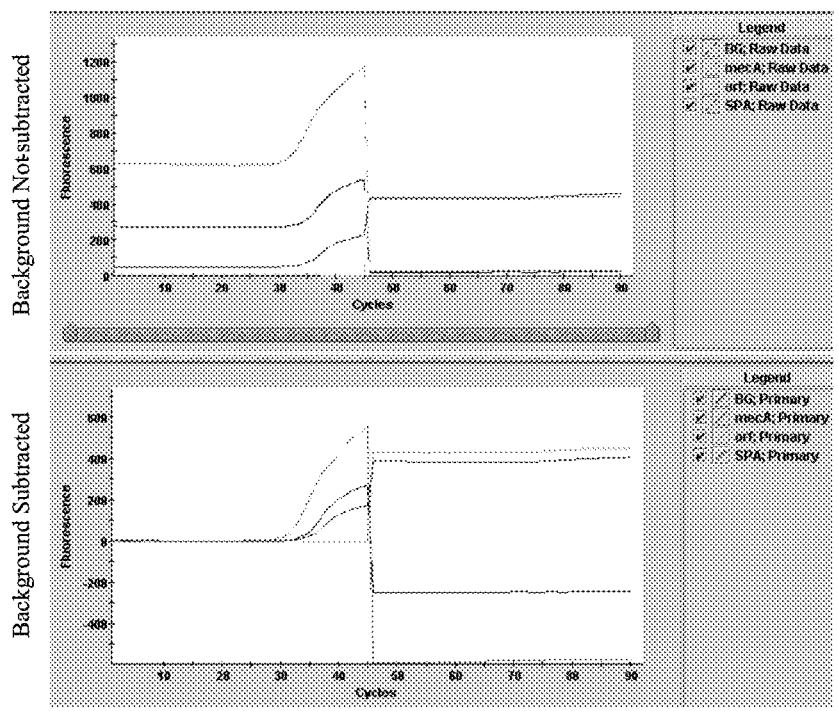
Figure 4C:
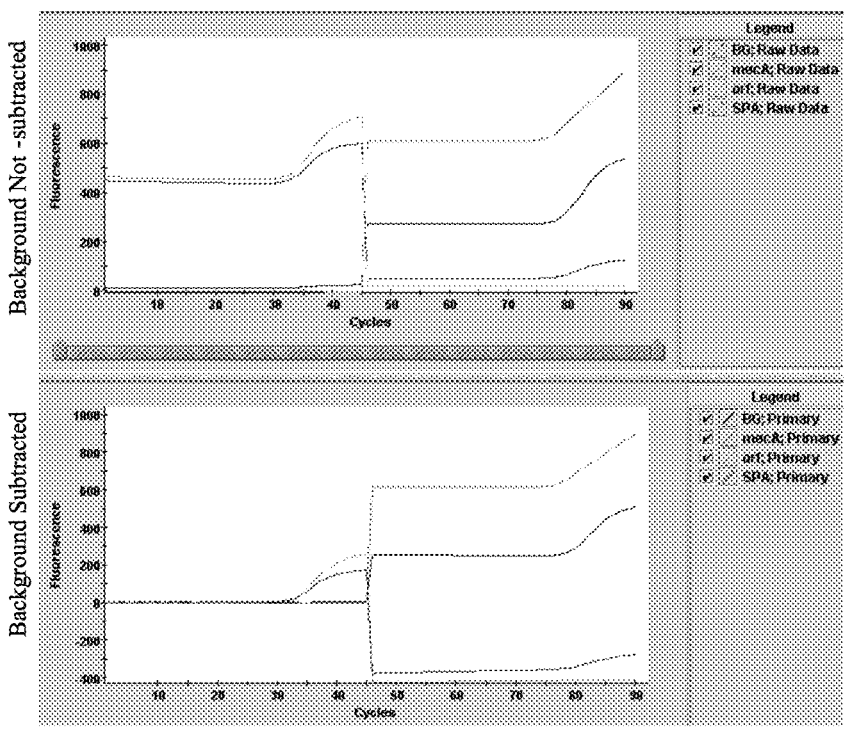
Figure 4D:
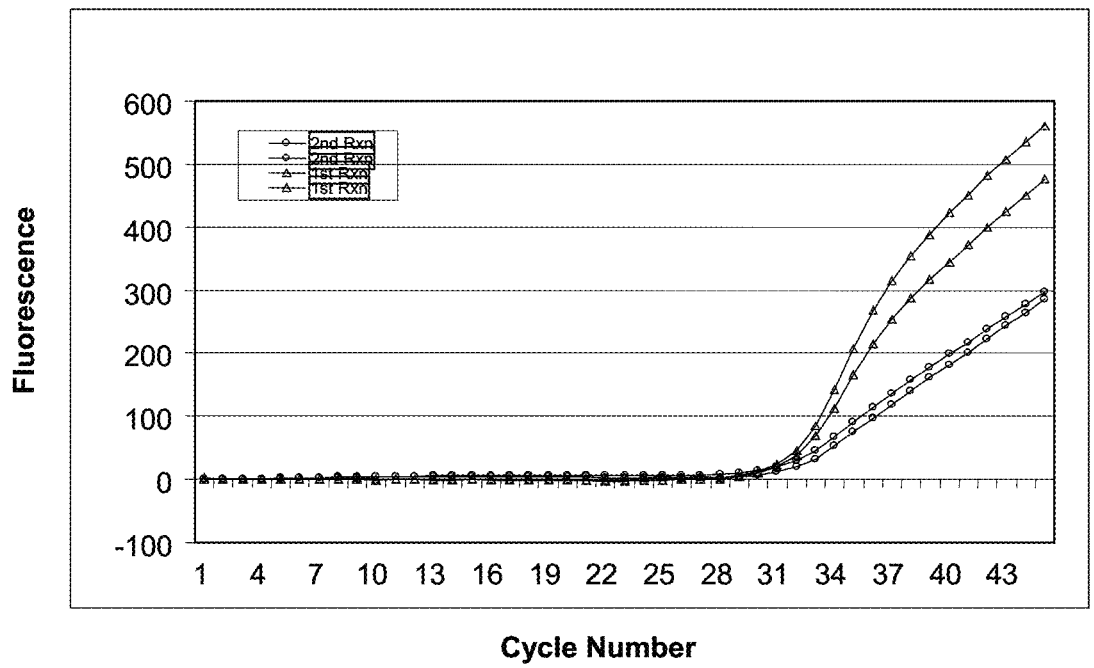
Figure 4E:
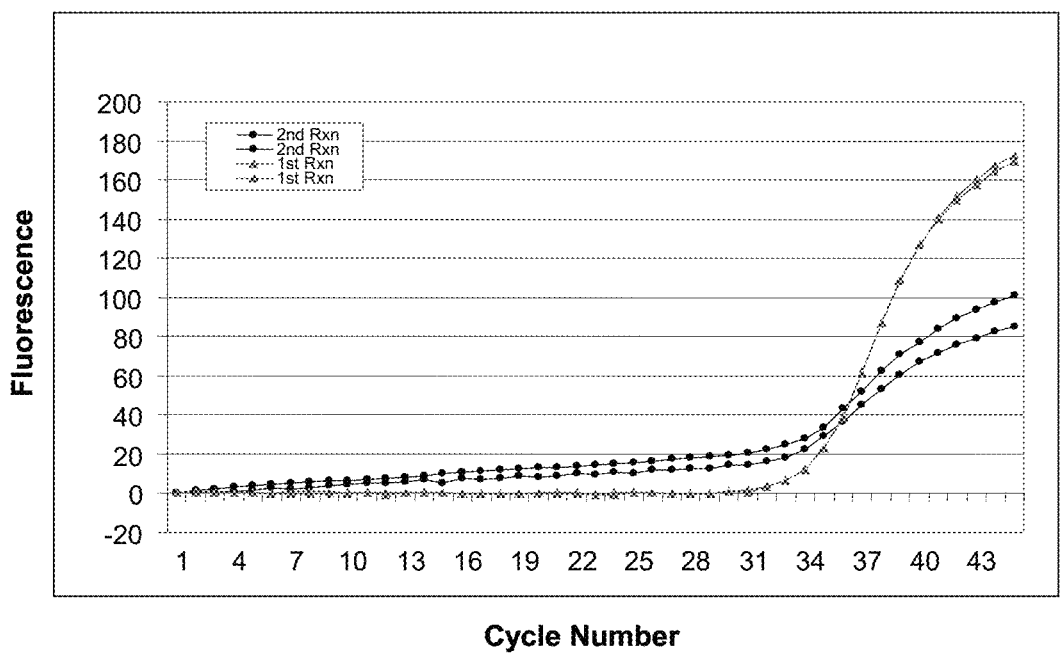
Figure 4F:
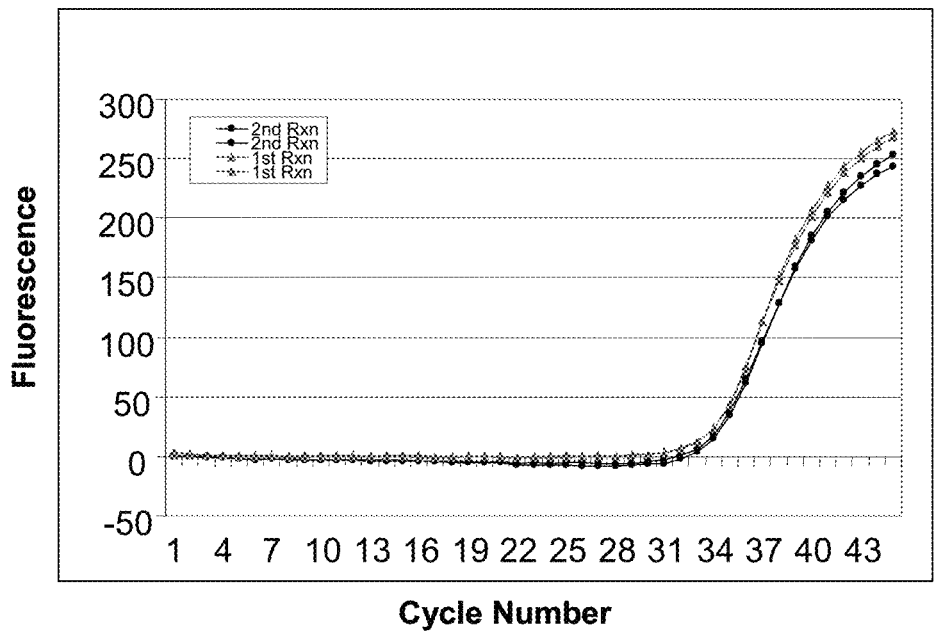
Figure 4G:
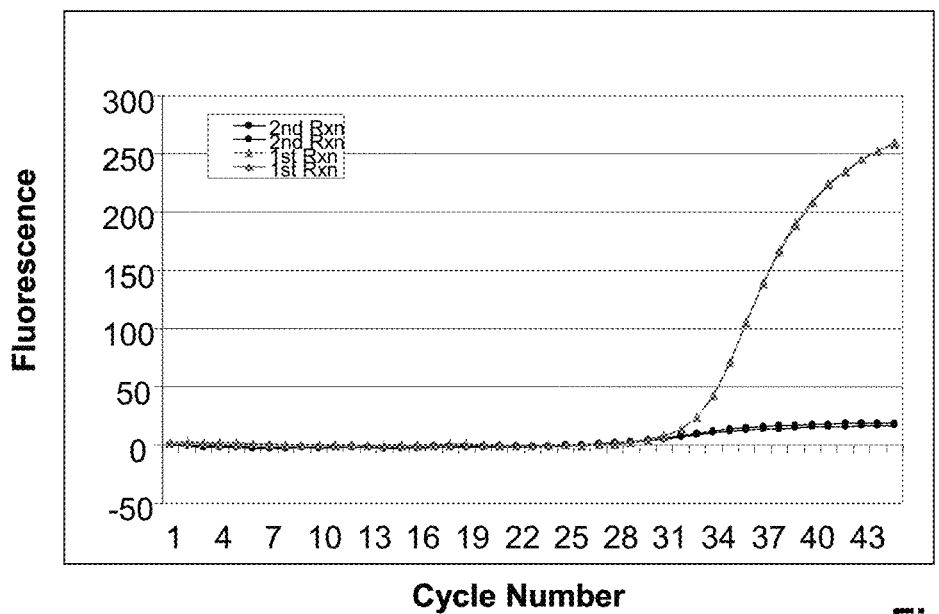
Figure 4H:
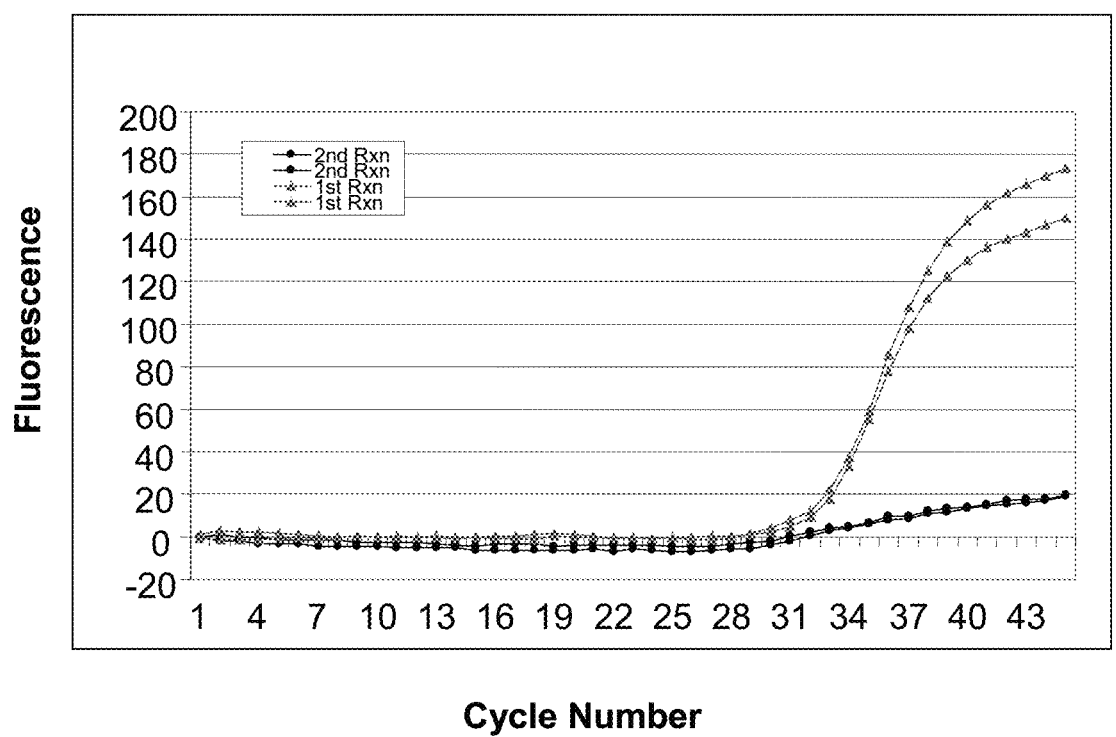

For both tests, sample was prepared by combining MRSA DNA and BG DNA in a TET buffer for a final concentration of 100 MRSA DNA copies per 25 µL reaction volume and 1000 BG DNA copies per 25 µL reaction volume. For the first test, reservoirs of two GENEXPERT™ amplification system cartridges were loaded as follows: 40 µL of MM1 was loaded into chamber 9, 40 µL of MM2 was loaded into chamber 11, 180 µL of sample was loaded into chamber 10, and 500 µL of TET buffer was loaded into chamber 2. The GENEXPERT™ amplification system was programmed substantially the same as in Example 1, a detailed listing of programming steps being set forth in FIG. 4A. Results are shown in FIGS. 4B-4H. Data from the first test (MM1 followed by MM2) is shown in FIG. 4B and data from the second test (MM2 followed by MM1) is shown in FIG. 4C. Signals for amplicons of BG, mecA, orf, and SPA are given in curves 1, 2, 3, and 4, respectively in both figures. The data indicate that the second reaction in each case only produced a low degree of amplification of the target sequences. Since the reaction mixtures were prepared beforehand, it is speculated that the second reaction reagent degraded prior to initiation of the reaction. FIGS. 4D-4H gives a direct comparison of the same target sequences amplified in the first reaction and the second reaction. The only target sequence that amplified equivalently in both reactions was orf.

Example 3

Figure 5A:
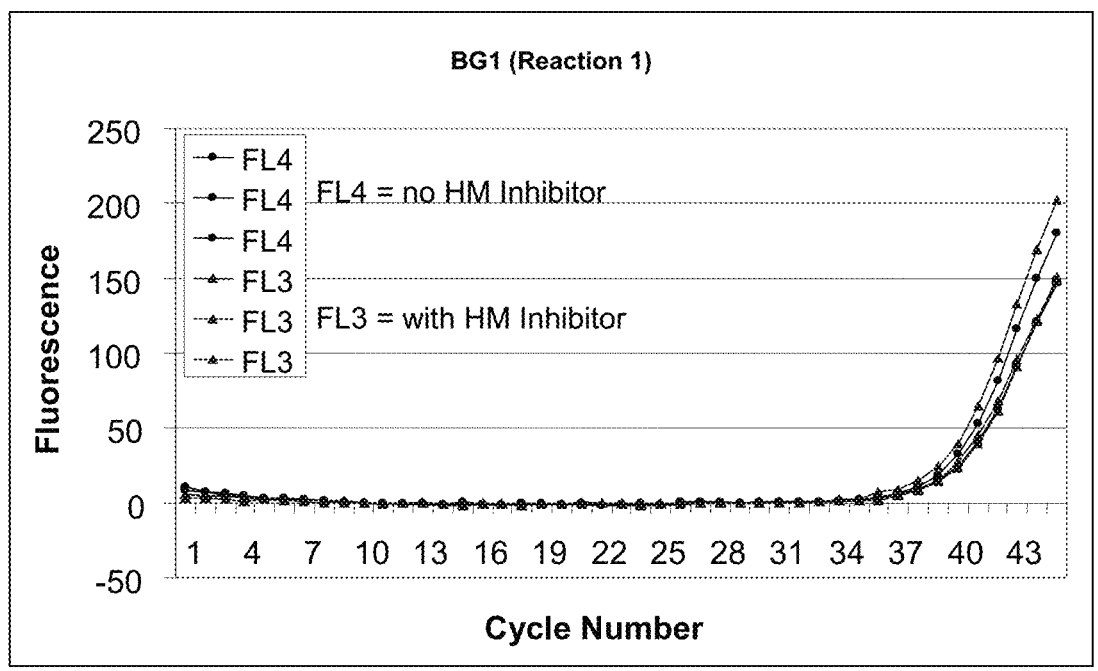
FIGS. 5A and 5B show results from replicate experiments for amplification of an internal control sequence.
Figure 5B:
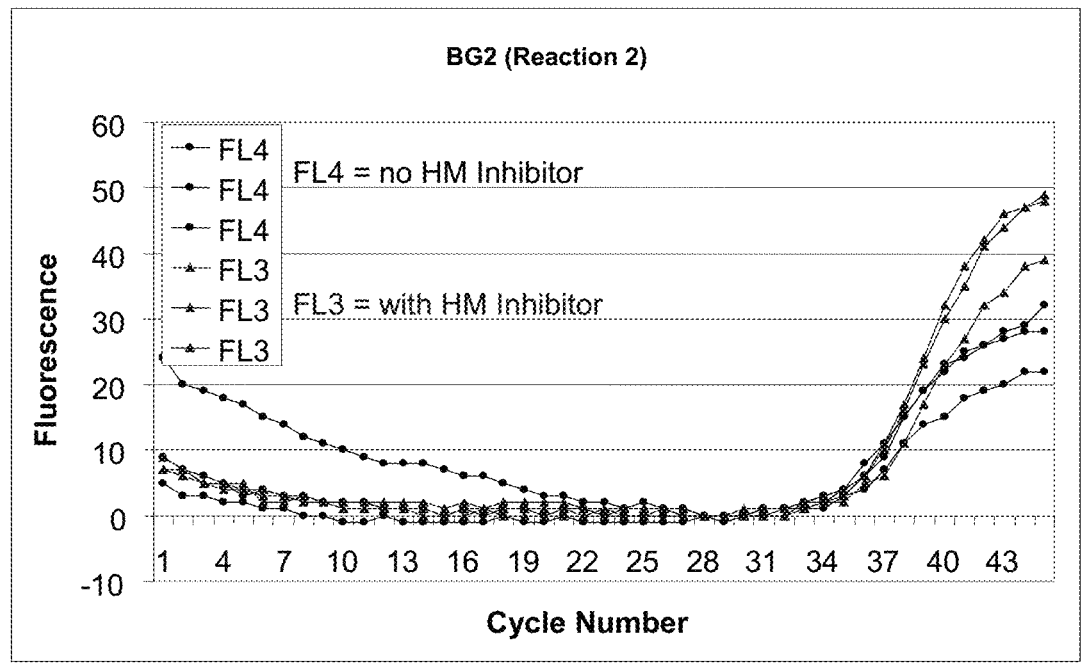

Detection of MRSA by Two Amplification Reactions Conducted Successively in the Same Reaction Chamber: Lyophilized Reagents In this example, the substantially the same tests were carried out as in Example 2, except that lyophilized reagents were used for both PCRs in each sequence of reaction and the concentrations of MRSA DNA and BG DNA were 10-fold lower. In parallel with these tests, the affects of including or leaving out a HOTMASTER™ polymerase inhibitor (Eppendorf AG, Hamburg, Germany) was also tested. (The HOTMASTER™ inhibitor inhibits polymerase binding in a temperature depending manner so that extensions are prevented at low temperatures). Results of replicate experiments for the internal control sequence, BG, are shown in FIGS. 5A (reaction 1) and 5B (reaction 2). Both reactions produce clearly detectable signals with the relative amplification of BG greatly improved with the use of lyophilized reagents.

Example 4

Removal of Reaction Chamber Bubbles by Purging with Air and Heating

Figure 6F:
Figure 6G:
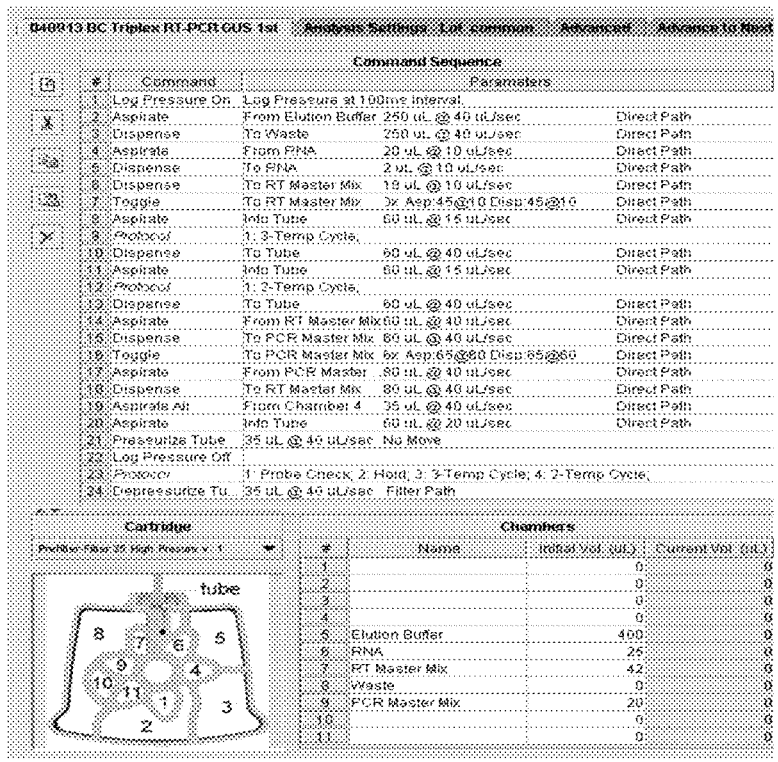
Figure 6H:
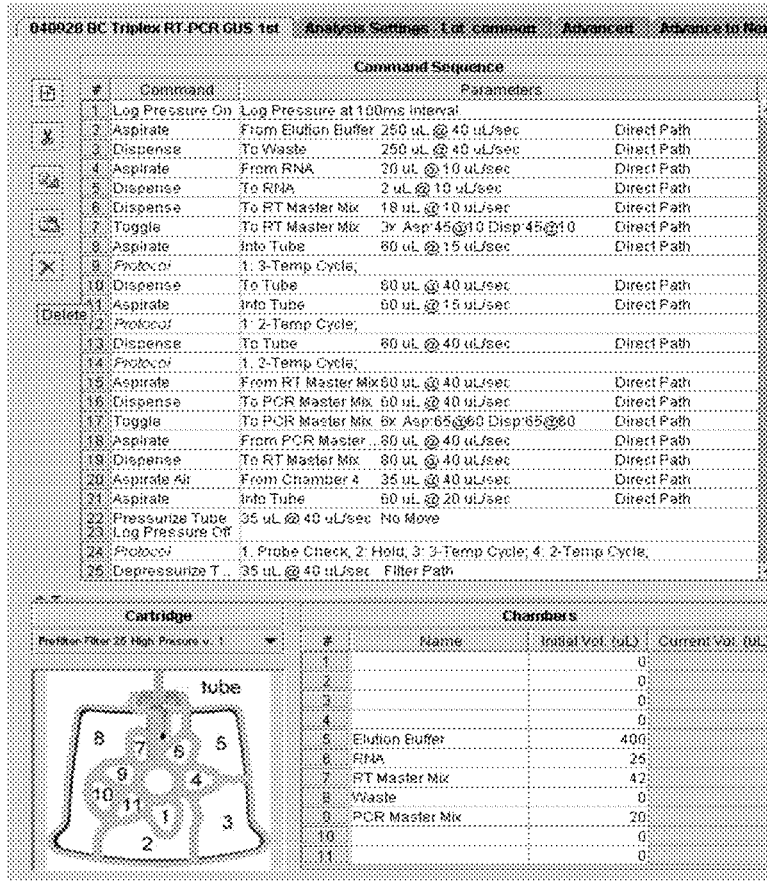

As noted above, the formation of bubbles in a reaction chamber between successive amplification reactions can degrade the performance of a system, particularly when amplification products are detected by optical signals. It is believed that bubbles form due to a film of reaction mixture that remains in the reaction chamber after a first (or prior) reaction. In this example, purging and/or heating steps were implemented to eliminate the formation of bubbles in the reaction chamber after a reaction mixture is removed, but before the reaction chamber is refilled with a subsequent reaction mixture. Such steps were implemented for successive mock reverse transcriptase reactions and PCRs, i.e. RT-PCRs, and actual RT-PCRs using a Cepheid GENEXPERT™ amplification system, under the programs listed in FIGS. 6A-6F (mock) and FIGS. 6G-6H (actual). The reactions were "mock" in the sense that the reagents did not contain probe, primers, or enzymes.

In the protocol implemented by the program steps of FIG. 6A, 600 µL of air was aspirated out of the reaction chamber after removal of a mock (RT) reaction mixture and before refilling with a mock PCR mixture. The result was that bubbles were observed in 2 out of 8 reaction chambers. In the protocol implemented by the program steps of FIG. 6B, the reaction chamber was heated to 100° C. for 5 seconds after removal of a mock (RT) reaction mixture and before refilling with a mock PCR mixture. The result was that bubbles were observed in 4 out of 4 reaction chambers. In the protocol implemented by the program steps of FIG. 6C, after removal of a mock (RT) reaction mixture, the reaction chamber was heated to 95° C. for 5 sec followed by cooling at 48° C. for 2 sec before refilling with a mock PCR mixture. The result was that bubbles were observed in 0 out of 4 reaction chambers. In the protocol implemented by the program steps of FIG. 6D, 600 µL of air was dispensed through (rather than aspirated out of) the reaction chamber after removal of a mock (RT) reaction mixture and before refilling with a mock PCR mixture. The result was that bubbles were observed in 1 out of 4 reaction chambers. In the protocol implemented by the program steps of FIG. 6E, after removal of a mock (RT) reaction mixture, the reaction chamber was heated to 100° C. for 3 sec followed by cooling at 48° C. for 2 sec before refilling with a mock PCR mixture.

The result was that bubbles were observed in 0 out of 8 reaction chambers. In the protocol implemented by the program steps of FIG. 6F, after removal of a mock (RT) reaction mixture, the reaction chamber was heated to 95° C. for 1 sec followed by cooling at 70° C. for 1 sec before refilling with a mock PCR mixture. The result was that bubbles were observed in 0 out of 8 reaction chambers.

As mentioned above, two actual RT-PCRs were performed using an RT reaction mixture and a PCR mixture described in Tables 4 and 5, respectively. Briefly, the assays were designed to generate amplicons from the GUS, PIP, and TAC gene in the RNA mix. An RNA mix was made by adding 1.76 µL of human lymph node total RNA and 0.44 µL of human breast total RNA to 107.8 µL of DEPC H2O. Three GENEXPERT™ amplification system cartridges were loaded as follows: 400 µL of water was added to chamber 5; 25 µL of RNA mix was added to chamber 6; 42 µL of RT Master Mix was added to chamber 7; and 20 µL of PCR Master Mix was added. In one RT-PCR, the reaction chamber was emptied between the RT reaction and PCR, but not heated (protocol shown in FIG. 6G). In the other RT-PCR, the reaction chamber was emptied, heated to 95° C. for 1 sec, followed by cooling to 70° C. for 1 sec, between the RT reaction and the PCR (protocol shown in FIG. 6H). There was no significant difference in the detection of amplicons between the two protocols.

The tests of this example indicate that heating the empty reaction chamber to 95° C., following by cooling, e.g. to 70° C., between reactions stopped bubble formation in the reaction chamber, even though the single replicate test with actual RT-PCR reagents was inconclusive. Solely aspirating or dispensing air through the empty reaction chamber between reactions was ineffective at removing bubbles.

TABLE 4

Number of Reactions = 4.5

| RT (Reverse Transcription) | Amt/60 µL | Amount/X rxns | Final Conc. | Vendor |
|---|---|---|---|---|
| DEPC-Treated Water | 4.45 | 20.025 | n/a | Ambion |
| 10X PCR Buffer (Plat Taq Buffer) | 6 | 27 | 1X | Invitrogen |
| MgCl2 (50 mM) | 6.4 | 28.8 | 5.3 & 4 mM | Invitrogen |
| dNTPs (2.5 mM) | 7.2 | 32.4 | 300 & 225 µM | Takara |
| GUS RT Primer (3 µM) BC65 | 1.6 | 7.2 | 80 nM/60 µL | Trilink |
| PIP RT Primer (3 µM) BC67 | 1.6 | 7.2 | 80 nM/60 µL | Trilink |
| TAC RT Primer (3 µM) BC66 | 1.6 | 7.2 | 80 nM/60 µL | Trilink |
| Protector (40 Units/µL) | 0.5 | 2.25 | 20 units/60 µL | Roche |
| Omniscript (4 U/µL) | 0.65 | 2.925 | 2.6 units/60 µL | Invitrogen |
| Total | 30 | 135 | | |

TABLE 5

Number of Reactions = 4.5

| PCR | Amt/80 µL | Amount/X rxns | Final Conc. | Vendor |
|---|---|---|---|---|
| DEPC-Treated Water | 0.4 | 1.8 | n/a | Ambion |
| 10X PCR buffer | 2 | 9 | 1x | Invitrogen |
| 20 µM GUS81fC (BC78) | 2.4 | 10.8 | 600 nM | TriLink |
| 20 µM GUSCp81r (BC77) | 2.4 | 10.8 | 600 nM | TriLink |
| 10 µM A647-GUS81P (BC57) | 1.6 | 7.2 | 200 µM | TriLink |
| 20 µM PIP-2F (BC38) | 1.6 | 7.2 | 400 nM | TriLink |
| 20 µM PIP-2rA (BC76) | 1.6 | 7.2 | 400 nM | TriLink |
| 10 µM FAM-PIP2 (BC83) | 1.6 | 7.2 | 200 nM | TriLink |
| 20 µM TACCpF (BC73) | 1.6 | 7.2 | 400 nM | TriLink |
| 20 µM TACCpR (BC74) | 1.6 | 7.2 | 400 nM | TriLink |
| 10 µM A532-TAC (BC51) | 1.6 | 7.2 | 200 nM | TriLink |
| Platinum Taq | 1.6 | 7.2 | .1 units/1 µL rxn | Invitrogen |
| Total | 20 | 90 | | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirely for all purposes.

What is claimed is:

1. A method of determining the presence or absence of a plurality target polynucleotides in a sample, the method comprising the steps of:
   (a) providing a reaction chamber in a reaction system;
   (b) mixing a portion of the sample with amplification reagents to form a first reaction mixture;
   (c) amplifying in the reaction chamber a first target polynucleotide in the reaction mixture to form a first amplicon whenever the first target polynucleotide is present, wherein an amplification indicator is present in the reaction mixture and is capable of generating an optical signal related to the first amplicon's quantity;
   (d) removing the entire reaction mixture from the reaction chamber upon the optical signal reaching or exceeding a predetermined value or upon the termination of the amplification reaction when the optical signal fails to reach the predetermined value;
   (e) repeating steps (b) through (d) to amplify in the reaction chamber a second target polynucleotide; and (f) determining the presence of the target polynucleotide in the sample when the optical signal reaches or exceeds the predetermined level and determining the absence of the target polynucleotide in the sample when the optical signal fails to reach the predetermined level.

2. The method of claim 1 further including, after the step of detecting, a step of fluidly transferring the reaction mixture from the reaction chamber to a waste reservoir.

3. The method of claim 2 further including, after the step of fluidly transferring, a step of washing the reaction chamber with a wash solution and transferring the wash solution to a waste reservoir.

4. The method of claim 1, wherein the step of mixing includes forming the reaction mixture in a reactant reservoir and fluidly transferring the reaction mixture to the reaction chamber.

5. The method of claim 1, wherein the step of amplifying is carried out with a polymerase chain reaction.

6. The method of claim 1, wherein the portion of the sample is mixed with the amplification reagents to form the reaction mixture in the reaction chamber.

7. The method of claim 1, wherein the step of repeating includes the steps of:
  (i) monitoring an optical signal of an indicator in the reaction mixture, the optical signal being related to a quantity of an amplicon of at least one of the target polynucleotides or of an internal standard in the reaction mixture; and
  (ii) automatically removing the reaction mixture from the reaction chamber and loading the reaction chamber with a subsequent reaction mixture whenever the optical signal reaches or exceeds a predetermined level.

8. The method of claim 7 further comprising, after the step of removing the reaction mixture from the reaction chamber and prior to the step of loading the subsequent reaction mixture, the steps of transferring air into the reaction chamber and heating the reaction chamber to a temperature at or above a DNA denaturation temperature.

9. The method of claim 8 further comprising the step of cooling the reaction chamber to a DNA annealing temperature after the step of heating the reaction chamber to a temperature at or above a DNA denaturation temperature.

10. A method of determining the presence or absence of a plurality of target polynucleotides in a sample, the method comprising the steps of:
  providing a reaction chamber selectably in fluid communication with a waste reservoir, a sample reservoir containing a sample, a first reactant reservoir containing first amplification reagents, and a second reactant reservoir containing second amplification reagents;
  combining a first portion of the sample and the first amplification reagents to form a first reaction mixture;
  subjecting the first reaction mixture to amplification reaction conditions in the reaction chamber to produce a first amplicon of one or more first target polynucleotides whenever such polynucleotides are present in the sample, wherein a first amplification indicator is present in the reaction chamber and is capable of generating a first optical signal related to the first amplicon's quantity;
  fluidly transferring the entire first reaction mixture to the waste reservoir whenever the first optical signal reaches or exceeds a predetermined level or whenever the first optical signal fails to reach the predetermined level and the amplification reaction is terminated;
  combining a second portion of the sample and the second amplification reagents to form a second reaction mixture;
  subjecting the second reaction mixture to amplification reaction conditions in the reaction chamber to produce a second amplicon of one or more second target polynucleotides whenever such polynucleotides are present in the sample, wherein a second amplification indicator is present in the reaction chamber and is capable of generating a second optical signal related to the second amplicon's quantity; and
  determining the presence of the first or second target polynucleotides in the sample when the first or second optical signal reaches or exceeds the predetermined level and determining the absence of the first or second target polynucleotides in the sample when the first or second optical signal reaches or exceeds the predetermined level.

11. The method of claim 10, further including a step of rinsing the reaction chamber after the step of fluidly transferring the first reaction mixture to the waste reservoir.

12. The method of claim 10, wherein the step of fluidly transferring the first reaction mixture to the waste reservoir includes the steps of:
  (i) monitoring an optical signal of an indicator in the first reaction mixture, the optical signal being related to a quantity of an amplicon of at least one of the target polynucleotides or of an internal standard in the first reaction mixture; and
  (ii) automatically fluidly transferring the first reaction mixture from the reaction chamber to the waste reservoir whenever the optical signal reaches or exceeds a predetermined level.

13. The method of claim 12, further comprising the steps of transferring air into the reaction chamber and heating the reaction chamber to a DNA denaturation temperature after the step of fluidly transferring the first reaction mixture to the waste reservoir.

14. The method of claim 13, wherein said DNA denaturation temperature is in the range of from about 90° C. to 99° C. and wherein after the step of heating, the reaction chamber is cooled to a DNA annealing temperature.

15. The method of claim 10, wherein the step of combining the first portion of the sample and the first amplification reagents includes fluidly transferring the first portion of the sample to the first reactant reservoir to form the first reaction mixture and fluidly transferring the first reaction mixture from the first reactant reservoir to the reaction chamber.

16. The method of claim 15, wherein the step of combining the second portion of the sample and the second amplification reagents includes fluidly transferring the second portion of the sample to the second reactant reservoir to form the second reaction mixture and fluidly transferring the second reaction mixture from the second reactant reservoir to the reaction chamber.

17. The method of claim 10, wherein each of the amplification reactions is a polymerase chain reaction.

18. A method of determining the presence or absence of a microorganism by a plurality of amplification reactions carried out in sequence, the method comprising the steps of:
  (a) amplifying one or more target polynucleotides characteristic of the microorganism from a portion of a sample in the presence of an indicator in a reaction mixture, the indicator being capable of generating an optical signal related to a quantity of an amplicon of the target polynucleotide in the amplification reaction, the reaction mixture being disposed in a reaction chamber;

(b) monitoring the optical signal of the indicator in the reaction mixture;

(c) automatically removing the entire reaction mixture from the reaction chamber and transferring to the reaction chamber with a subsequent reaction mixture when the optical signal reaches or exceeds a predetermined level, otherwise automatically terminating the sequence of amplification reactions;

(d) repeating steps (a) through (c) until the sequence of amplification reactions has been carried out or the sequence of amplification reactions has been terminated; and (e) determining the presence of the microorganism in the sample when an amplicon of the one or more target polynucleotides characteristic of the microorganism is detected, and determining the absence of the microorganism in the sample when no amplicon of the one or more target polynucleotides characteristic of the microorganism is detected.

* * * * *